us010710081B2

(12) United States Patent
Liu

(10) Patent No.: US 10,710,081 B2
(45) Date of Patent: Jul. 14, 2020

(54) INTEGRATED SYSTEM FOR NUCLEIC ACID AMPLIFICATION AND DETECTION

(71) Applicant: LIFE TECHNOLOGIES CORPORATION, Carlsbad, CA (US)

(72) Inventor: Jason Yingjie Liu, Foster City, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 384 days.

(21) Appl. No.: 15/125,205

(22) PCT Filed: Mar. 16, 2015

(86) PCT No.: PCT/US2015/020812
§ 371 (c)(1),
(2) Date: Sep. 12, 2016

(87) PCT Pub. No.: WO2015/139054
PCT Pub. Date: Sep. 17, 2015

(65) Prior Publication Data
US 2017/0182492 A1 Jun. 29, 2017

Related U.S. Application Data

(60) Provisional application No. 61/953,316, filed on Mar. 14, 2014.

(51) Int. Cl.
B01L 3/00 (2006.01)
(52) U.S. Cl.
CPC .......... B01L 3/50851 (2013.01); B01L 3/508 (2013.01); B01L 3/5088 (2013.01);
(Continued)

(58) Field of Classification Search
CPC .. B01L 3/50851; B01L 3/508; B01L 3/50853; B01L 3/5088; B01L 2300/047; B01L 2200/0689; B01L 2300/168; B01L 2300/161; B01L 2300/0654; B01L 2300/041; B01L 2300/0822; B01L 2300/021; B01L 2200/10; C12Q 1/686; C12Q 1/6806
See application file for complete search history.

(56) References Cited

U.S. PATENT DOCUMENTS 8,009,882 B2    8/2011  Fenrich et al.
2003/0197853 A1* 10/2003 Fenrich .............. G06K 9/00013
                                                        356/71

(Continued)

FOREIGN PATENT DOCUMENTS

EP    2604688      6/2013
WO   2007/022045   2/2007
(Continued)

OTHER PUBLICATIONS

EBI, "MMLV RT Mutant Protein", Accession No. AEX83173, Jun. 14, 2007, 1-4.
(Continued)

Primary Examiner — Joseph G. Dauner

(57) ABSTRACT

Devices, systems, methods, and kits are disclosed for amplifying small quantities of nucleic acid and identifying the nucleic acid sequences of the amplified nucleic acid products.

9 Claims, 21 Drawing Sheets

(52) U.S. Cl.
CPC ... *B01L 3/50853* (2013.01); *B01L 2200/0689* (2013.01); *B01L 2200/10* (2013.01); *B01L 2300/021* (2013.01); *B01L 2300/041* (2013.01); *B01L 2300/047* (2013.01); *B01L 2300/0654* (2013.01); *B01L 2300/0822* (2013.01); *B01L 2300/161* (2013.01); *B01L 2300/168* (2013.01)

(56) References Cited

U.S. PATENT DOCUMENTS

| | | | |
|---|---|---|---|
| 2011/0081704 A1 | 4/2011 | Smith et al. | |
| 2013/0101184 A1* | 4/2013 | Harrold | G06T 7/0012 382/124 |
| 2013/0202182 A1* | 8/2013 | Rowe | A61B 10/02 382/133 |
| 2013/0295572 A1* | 11/2013 | Liu | G01N 1/30 435/6.12 |
| 2016/0154990 A1* | 6/2016 | Harrold | A61B 5/1172 382/116 |

FOREIGN PATENT DOCUMENTS

| | | |
|---|---|---|
| WO | 2009/125006 | 10/2009 |
| WO | 2013/063230 | 5/2013 |

OTHER PUBLICATIONS

EBI, "Reverse Transcriptase Mutant", Accession No. AZT62682, Apr. 12, 2012, 1-2.

Ng et al., "Targeted Capture and Massively Parallel Sequencing of Twelve Human Exomes", Nature, vol. 461, No. 7261, Sep. 10, 2009, 272-276.

PCT/US2015/020812, International Preliminary Report dated Sep. 14, 2016, 1-18.

PCT/US2015/020812, International Search Report Written Opinion dated Aug. 24, 2015, 1-25.

* cited by examiner

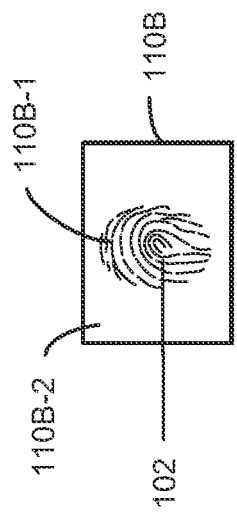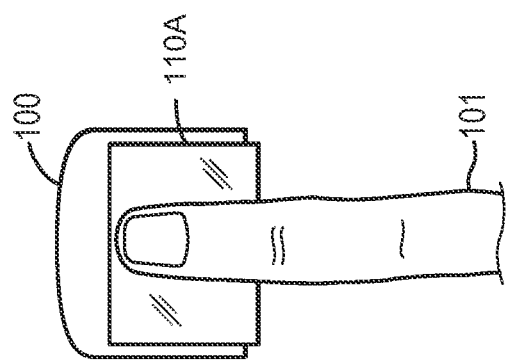

INTEGRATED SYSTEM FOR NUCLEIC ACID AMPLIFICATION AND DETECTION

CROSS-REFERENCE TO RELATED APPLICATIONS

This application claims priority to U.S. Provisional Patent Application No. 61/953,316 filed Mar. 14, 2014.

FIELD

The present teachings relate to devises and methods for obtaining biometric data and nucleic acids for use in human identification and forensic science.

INTRODUCTION

Forensic evidence and biometric data are often used together to identify perpetrators of criminal activities as well as for the identification of missing persons, victims of mass disasters, paternity testing and to exonerate the innocent. The ability to simultaneously collect biometric data such as fingerprints, an iris or retinal scan, an image or photo of an individual can, with a biological sample(s) such as forensic evidence including but not limited to blood, tissue, hair, body fluid or a buccal sample, provide a system for expediting identification, access control, and screening of individuals. Furthermore, maintaining identification of related data points and correlating the data with the respective biological samples can be complicated and susceptible to errors which compromise the chain of custody. Therefore, there remains a need to accurately collect, associate correctly, and process biometric data and biological samples from a single individual in one collection step or workflow.

SUMMARY

In a first aspect, a device for collection of a biological sample containing nucleic acid from an individual is provided, including a base substrate component having at least a first surface area, where the at least first surface area is transparent or translucent to an energy wave capable of imaging at least one ridge and valley signature of an appendage of the individual; configured to collect the biological sample from the appendage; and made of one or more materials compatible with reaction conditions of a nucleic acid amplification reaction. In some embodiments, the base substrate component may be polymeric film or glass. In various embodiments, all surface areas of the substrate component may be transparent or translucent to the energy wave. In various embodiments, all surface areas of the base substrate component may be configured to be compatible with the nucleic acid amplification reaction conditions. In various embodiments, the at least first surface area may be hydrophilic. In some embodiments, the base substrate component further includes a second surface area surrounding the at least first surface area where the second surface area is hydrophobic.

The device may further include a frame component to support the substrate component. In some embodiments, the frame component may be formed from a material selected from a polymer, a metal, a metal alloy, a glass, a silicon material or combination thereof.

The device may further include a mask component, wherein the mask component is configured to: attach to the base substrate component; surround the at least first surface area of the base substrate component; and is made of one or more materials compatible with reaction conditions of a nucleic acid amplification reaction. In some embodiments, the mask component may permit addition of nucleic acid amplification reagents to the at least first surface area of the base substrate component. In various embodiments, the mask component may be placed in position surrounding the at least first surface area of the base substrate component after the biological sample from the appendage of the individual has been collected. In some embodiments, the mask component may be attached to the base substrate component by a hinged attachment. In other embodiments, the mask component may be attached to the base substrate component by adhesion. In various embodiments, the mask component may be made of a polymeric material.

The device may further include a cover component. In some embodiments, the cover component may include material compatible with reaction conditions of a nucleic acid amplification reaction.

In various embodiments, the base substrate component may be chemically modified with a chemical functional group selected from an amino group, a chloromethyl group, a hydroxyl group, a carboxyl group and a quaternary amino group. In some embodiments, the chemical functional group modifying the base substrate component may include linkers selected from amino-functionalized linkers, sulfhydryl linkers, homobifunctional linkers and heterobifunctional linkers. In some embodiments, the base substrate component may be modified chemically to attach, covalently or noncovalently, a reagent, including but not limited to an enzyme, a binding partner, a surfactant, an anionic polymer or a zwitterionic species. In some embodiments, the base substrate component may be configured to permit the release of the at least one nucleic acid from the biological sample. The base substrate component may be compatible with nucleic acid sequencing reaction conditions.

The device may further have a base substrate component which incorporates an identifier to associate the biological sample of the individual with the at least one ridge and valley signature of the individual, wherein the identifier is alphanumeric, graphical, magnetic, or electromagnetic. In other embodiments, when the mask component is present, the mask component may further include an identifier to associate the biological sample of the individual with the at least one ridge and valley signature of the individual, wherein the identifier is alphanumeric, graphical, magnetic, or electromagnetic. In some embodiments, the identifier may be a barcode.

The device may further be configured for archiving the biological sample or for shipping the sample to another location for testing.

In another aspect, a system for collection of a biological sample comprising nucleic acid and at least one ridge and valley signature of an individual is provided, including: at least a first imaging component comprising a scanning surface configured to permit an energy wave to penetrate the scanning surface, wherein the energy wave is configured to image the at least one ridge and valley signature of an appendage of the individual; and a device for collection of a biological sample containing nucleic acid from an individual is provided, including a base substrate component having at least a first surface area, where the at least first surface area is transparent or translucent to an energy wave capable of imaging at least one ridge and valley signature of an appendage of the individual; configured to collect the biological sample from the appendage; and made of one or more materials compatible with reaction conditions of a nucleic acid amplification reaction. In some embodiments, the base substrate component may be polymeric film or glass. In some embodiments, the system is configured to collect at least one ridge and valley signature by imaging the appendage through the scanning surface and a base substrate component of the device while the appendage is positioned upon at least a first surface area of the base substrate component. In some embodiments, the base substrate component of the device of the system may be polymeric film or glass. In various embodiments, all surface areas of the substrate component may be transparent or translucent to the energy wave. In various embodiments, all surface areas of the base substrate component may be configured to be compatible with the nucleic acid amplification reaction conditions. In various embodiments, the at least first surface area may be hydrophilic. In some embodiments, the base substrate component further includes a second surface area surrounding the at least first surface area where the second surface area is hydrophobic.

The device of the system may further include a frame component to support the substrate component. In some embodiments, the frame component may be formed from a material selected from a polymer, a metal, a metal alloy, a glass, a silicon material or combination thereof.

The device of the system may further include a mask component, wherein the mask component is configured to: attach to the base substrate component; surround the at least first surface area of the base substrate component; and is made of one or more materials compatible with reaction conditions of a nucleic acid amplification reaction. In some embodiments, the mask component may permit addition of nucleic acid amplification reagents to the at least first surface area of the base substrate component. In various embodiments, the mask component may be placed in position surrounding the at least first surface area of the base substrate component after the biological sample from the appendage of the individual has been collected. In some embodiments, the mask component may be attached to the base substrate component by a hinged attachment. In other embodiments, the mask component may be attached to the base substrate component by adhesion. In various embodiments, the mask component may be made of a polymeric material.

The device of the system may further include a cover component. In some embodiments, the cover component may include material compatible with reaction conditions of a nucleic acid amplification reaction.

In various embodiments, the base substrate component of the device of the system may be chemically modified with a chemical functional group selected from an amino group, a chloromethyl group, a hydroxyl group, a carboxyl group and a quaternary amino group. In some embodiments, the chemical functional group modifying the base substrate component may include linkers selected from amino-functionalized linkers, sulfhydryl linkers, homobifunctional linkers and heterobifunctional linkers. In some embodiments, the base substrate component may be modified chemically to attach, covalently or noncovalently, a reagent, including but not limited to an enzyme, a binding partner, a surfactant, an anionic polymer or a zwitterionic species. In some embodiments, the base substrate component may be configured to permit the release of the at least one nucleic acid from the biological sample. The base substrate component may be compatible with nucleic acid sequencing reaction conditions.

The device of the system may further have a base substrate component which incorporates an identifier to associate the biological sample of the individual with the at least one ridge and valley signature of the individual, wherein the identifier is alphanumeric, graphical, magnetic, or electromagnetic. In other embodiments, when the mask component is present, the mask component may further include an identifier to associate the biological sample of the individual with the at least one ridge and valley signature of the individual, wherein the identifier is alphanumeric, graphical, magnetic, or electromagnetic. In some embodiments, the identifier may be a barcode.

The device of the system may further be configured for archiving the biological sample or for shipping the sample to another location for testing.

In some embodiments, the scanning surface may be formed from a material selected from a plastic, a polyolefin, a polystyrene, a metal, a metal alloy, a glass, a silicon or combinations thereof. In some embodiments, the material of the scanning surface may be transparent or translucent. In various embodiments, the system may be configured to collect the biological sample and the at least one ridge and valley signature simultaneously.

The system may further include a processor configured to transmit the ridge and valley signature of the individual to at least one database comprising ridge and valley signatures selected from the group consisting of a forensic, criminal, identity, child identity, missing persons, immigration, department of motor vehicles, terrorist, paternity, arrestee, convict database, access control and any combination thereof.

The system may further include a nucleic acid amplification reaction component, where the reaction component may be configured to subject the device containing the biological sample on the base substrate component to a nucleic acid amplification reaction. In some embodiments, the reaction component may be configured to subject the device to thermocycling conditions. In various embodiments, the nucleic acid amplification reaction on the device may be sealed with a sealing solution. In some embodiments, the nucleic acid amplification reaction may be a part of an INDEL, SNP or STR analysis. In some embodiments, the reaction component may be further configured to subject more than one device to nucleic amplification reactions at the same time. In various embodiments, the reaction component may be further configured to subject the device to a nucleic acid sequencing reaction.

The system may further include a detection component, wherein the detection component may be configured to detect at least one product of the nucleic acid amplification, thereby identifying a corresponding sequence of the at least one nucleic acid amplification product. In some embodiments, the identification of the at least one nucleic acid amplification product sequence may provide a nucleic acid sequence identification of the individual.

The system may further include a processor configured to transmit the nucleic acid sequence identity of the individual to at least one database comprising nucleic acid sequence identities selected from the group consisting of a forensic, criminal, identity, child identity, missing persons, immigration, department of motor vehicles, terrorist, paternity, arrestee, convict database, access control and any combination thereof.

In yet another aspect, a kit is provided, including a device for collection of a biological sample containing nucleic acid from an individual is provided, including a base substrate component having at least a first surface area, where the at least first surface area is transparent or translucent to an energy wave capable of imaging at least one ridge and valley signature of an appendage of the individual; configured to collect the biological sample from the appendage; and made of one or more materials compatible with reaction conditions of a nucleic acid amplification reaction, and optionally, instructions for its use.

In some embodiments, the base substrate component of the device of the kit may be polymeric film or glass. In various embodiments, all surface areas of the substrate component may be transparent or translucent to the energy wave. In various embodiments, all surface areas of the base substrate component may be configured to be compatible with the nucleic acid amplification reaction conditions. In various embodiments, the at least first surface area may be hydrophilic. In some embodiments, the base substrate component further includes a second surface area surrounding the at least first surface area where the second surface area is hydrophobic.

The device of the kit may further include a frame component to support the substrate component. In some embodiments, the frame component may be formed from a material selected from a polymer, a metal, a metal alloy, a glass, a silicon material or combination thereof.

The device of the kit may further include a mask component, wherein the mask component is configured to: attach to the base substrate component; surround the at least first surface area of the base substrate component; and is made of one or more materials compatible with reaction conditions of a nucleic acid amplification reaction. In some embodiments, the mask component may permit addition of nucleic acid amplification reagents to the at least first surface area of the base substrate component. In various embodiments, the mask component may be placed in position surrounding the at least first surface area of the base substrate component after the biological sample from the appendage of the individual has been collected. In some embodiments, the mask component may be attached to the base substrate component by a hinged attachment. In other embodiments, the mask component may be attached to the base substrate component by adhesion. In various embodiments, the mask component may be made of a polymeric material.

The device of the kit may further include a cover component. In some embodiments, the cover component may include material compatible with reaction conditions of a nucleic acid amplification reaction.

In various embodiments, the base substrate component of the device of the kit may be chemically modified with a chemical functional group selected from an amino group, a chloromethyl group, a hydroxyl group, a carboxyl group and a quaternary amino group. In some embodiments, the chemical functional group modifying the base substrate component may include linkers selected from amino-functionalized linkers, sulfhydryl linkers, homobifunctional linkers and heterobifunctional linkers. In some embodiments, the base substrate component may be modified chemically to attach, covalently or noncovalently, a reagent, including but not limited to an enzyme, a binding partner, a surfactant, an anionic polymer or a zwitterionic species. In some embodiments, the base substrate component may be configured to permit the release of the at least one nucleic acid from the biological sample. The base substrate component may be compatible with nucleic acid sequencing reaction conditions.

The device of the kit may further have a base substrate component which incorporates an identifier to associate the biological sample of the individual with the at least one ridge and valley signature of the individual, wherein the identifier is alphanumeric, graphical, magnetic, or electromagnetic. In other embodiments, when the mask component is present, the mask component may further include an identifier to associate the biological sample of the individual with the at least one ridge and valley signature of the individual, wherein the identifier is alphanumeric, graphical, magnetic, or electromagnetic. In some embodiments, the identifier may be a barcode.

The device of the kit may further be configured for archiving the biological sample or for shipping the sample to another location for testing.

The kit may further include reagents for stabilizing the biological sample on the substrate component for archiving or shipping. The kit may further include reagents for amplification of the nucleic acid of the biological sample. The kit may further include a sealing solution. In some embodiments, the reagents may be suitable for performing at least one of a STR analysis, a SNP analysis, and an Indel analysis.

The kit may further include at least one enclosure to protect the device from contamination prior to use. The kit may further include at least one enclosure to protect the device from contamination while archiving or shipping after the nucleic acid has been deposited on the base substrate component. In some embodiments, the at least one enclosure may include an identifier to associate the device containing the biological sample with at least one of the ridge and valley signature of the individual and the identity of the individual providing the biological sample.

In another aspect, a method is provided to collect a biological sample containing at least one nucleic acid and collection of at least one ridge and valley signature of an appendage of an individual, including the steps of providing at least a first imaging component. The at least first imaging component is configured to provide an energy wave capable of imaging the at least one ridge and valley signature; and have a scanning surface configured to permit the energy wave to penetrate the scanning surface. The method also includes the step of providing a device having a base substrate component having at least a first surface area, where the base substrate component is configured to permit the energy wave to penetrate the substrate; collect the biological sample from the appendage of the individual; and be made of one or more materials configured to be compatible with reaction conditions of a nucleic acid amplification reaction. The device may be any of the embodiments of the devices described here, with any combination of components. The method also includes the step of positioning an appendage of the individual on the scanning surface and in contact with the base substrate component, thereby collecting the biological sample; and collecting the at least one ridge and valley signature from the appendage imaged by the energy wave. The appendage image may be a finger, toe, palm of a hand or sole of a foot. The steps of collecting the biological sample and collecting the at least one ridge and valley signature may be performed simultaneously.

In some embodiments, the at least first imaging component may be an optical scanner or a capacitance scanner, and the at least one ridge and valley signature may be collected electronically.

The method may further include the step of transmitting the at least one ridge and valley signature of the individual to at least one database comprising ridge and valley signatures selected from the group consisting of a forensic, criminal, identity, child identity, missing persons, immigration, department of motor vehicles, terrorist, paternity, arrestee, convict database, access control or any combination thereof.

The method may further include the step of providing an identifier on at least one component of the device to associate the biological sample of the individual with the at least one ridge and valley signature of the individual, wherein the identifier is alphanumeric, graphical, magnetic, or electromagnetic. In some embodiments, the identifier is a barcode.

The method may also include the step of archiving at least the base substrate component of the device after performing the step of collecting the biological sample.

The method may further include the step of mailing the device to another location for archiving or testing, after performing the step of collecting the biological sample.

The method may further entail the step of subjecting the biological sample collected to the base substrate component to a nucleic acid amplification reaction. In some embodiments, the nucleic acid amplification reaction is a polymerase chain reaction. The method may further entail the step of performing a nucleic acid sequencing reaction while still present on the base substrate component. In some embodiments, the nucleic acid amplification reaction and the nucleic acid sequencing reaction may be performed in the same reaction well, without transfer or stoppage between processes. In some embodiments, the amplification reaction may be one component of a STR analysis, a SNP analysis, or an Indel analysis.

The method may further entail the step of placing a mask component of the device upon the base substrate component, thereby surrounding the at least first surface area of the base substrate component. The mask component may be made of one or more materials compatible with reaction conditions of a nucleic acid amplification reaction. In some embodiments, the step of placing the mask component upon the base substrate component is performed before the step of collecting the biological sample. In other embodiments, the step of placing the mask component upon the base substrate component is performed after the step of collecting the biological sample and before the step of subjecting the biological sample on the base substrate component to a nucleic acid amplification reaction. The method may further include the step of sealing the nucleic acid amplification reaction with a sealing solution. The reaction well may have no other upper closure besides the sealing solution. Alternatively, the method may include the step of placing a cover component of the device over the biological sample collected to the base substrate component during the nucleic acid amplification reaction. In some embodiments, the step of placing the cover component over the biological sample on the base substrate component is performed after reagents for the nucleic acid amplification reaction have been added to the biological sample on the base substrate component, and before the reaction commences. The method may also include the step of placing a cover component over the biological sample collected to the base substrate component for shipping or archiving prior to a nucleic acid amplification. The method may further include the step of detecting a sequence of the nucleic acid, thereby identifying the individual. The method may further include the step of transmitting the nucleic acid sequence identity of the individual to at least one database comprising nucleic acid sequence identities selected from the group consisting of a forensic, criminal, identity, child identity, missing persons, immigration, department of motor vehicles, terrorist, paternity, arrestee, convict database, access control and any combination thereof.

In yet another aspect, a method is provided to identify an individual, including the step of providing at least a first imaging component configured to provide an energy wave capable of imaging at least one ridge and valley signature of an appendage of an individual; and comprise a scanning surface configured to permit the energy wave to penetrate the scanning surface. The method also includes the step of providing a device comprising a base substrate component having at least a first surface area, where the substrate component is configured to permit the energy wave to penetrate the substrate; collect a biological sample comprising nucleic acid from the appendage of the individual; and be made of one or more materials configured to be compatible with reaction conditions of a nucleic acid amplification reaction. The device may be any of the embodiments of the devices described here, with any combination of components. The method also includes the step of positioning the appendage of the individual on the scanning surface and in contact with the at least first surface areas of the base substrate component, thereby collecting the biological sample; collecting the at least one ridge and valley signature from the appendage imaged by the energy wave, thereby providing a ridge and valley signature identification of the individual; subjecting the nucleic acid of the biological sample collected to the base substrate component to a nucleic acid amplification reaction; and detecting a sequence of the nucleic acid, thereby identifying the individual. The steps of collecting the biological sample and collecting the at least one ridge and valley signature may be performed simultaneously.

In some of the embodiments, the at least first imaging component may be an optical scanner or a capacitance scanner. In various embodiments, the at least one ridge and valley signature may be collected electronically. In some embodiments, the appendage may be a finger, toe, palm of a hand or sole of a foot. In other embodiments, the nucleic acid amplification reaction may be a polymerase chain reaction. In various embodiments, the method may include the step of performing a DNA sequencing reaction while still present on the base substrate component. In some embodiments, the amplification reaction may be one component of a STR analysis, a SNP analysis, or an Indel analysis.

The method may further include the step of placing a mask component of the device upon the base substrate component, thereby surrounding the at least first surface area of the substrate, where the mask component is made of one or more materials compatible with reaction conditions of a nucleic acid amplification reaction. In some embodiments, the step of placing the mask component upon the base substrate component may be performed before the step of collecting the biological sample. In other embodiments, the step of placing the mask component upon the base substrate component may be performed after the step of collecting the biological sample and before the step of subjecting the biological sample on the substrate component to a nucleic acid amplification reaction.

The method may further include the step of sealing the nucleic acid amplification reaction with a sealing solution. The nucleic acid amplification reaction mixture may have no other upper enclosure.

The method may further include the step of placing a cover component of the device over the biological sample collected to the base substrate component. The cover may be placed over the at least first surface of the base substrate component containing the nucleic acid for shipping and archiving the device after collection of the biological sample. In some embodiments, the cover component may be placed over the biological sample on the substrate component after reagents for the nucleic acid amplification reaction have been added to the biological sample on the base substrate component, and before the reaction commences.

The method may further include the step of transmitting the at least one ridge and valley signature of the individual to at least one database comprising ridge and valley signatures selected from the group consisting of a forensic, criminal, identity, child identity, missing persons, immigration, department of motor vehicles, terrorist, paternity, arrestee, convict database, access control or any combination thereof.

The method may further include the step of providing an identifier on at least one component of the device to associate the biological sample of the individual with the at least one ridge and valley signature of the individual, where the identifier is alphanumeric, graphical, magnetic, or electromagnetic. In some embodiments, the identifier is a barcode.

The method may further include the step of archiving at least the base substrate component of the device after performing the step of collecting the biological sample.

The method may further include the step of mailing the device to another location for archiving or testing, after performing the step of collecting the biological sample.

The method may also include the step of transmitting the nucleic acid sequence identity of the individual to at least one database comprising nucleic acid sequence identities selected from the group consisting of a forensic, criminal, identity, child identity, missing persons, immigration, department of motor vehicles, terrorist, paternity, arrestee, convict database, access control and any combination thereof.

The method may also include the step of collecting at least a second image of the individual, selected from a facial image, an iris image, a retinal image or an ear image of the individual. In some embodiments, an identifier may associate the at least second image with the biological sample and the at least one ridge and valley signature of the individual.

In another aspect, a system is provided for identification of a target nucleic acid, including: a base substrate component including one or more hydrophilic sites separated by hydrophobic zones where at least one hydrophilic site is configured to contain at least one target nucleic acid and further where the base substrate component is made of one or more materials compatible with reaction conditions of a nucleic acid amplification reaction; a reaction component configured to amplify the at least one target nucleic acid at the at least one hydrophilic site to form at least one nucleic acid amplification product; and a detection component configured to identify at least one nucleic acid sequence of the at least one nucleic acid amplification product. In some embodiments, the base substrate component may be polymeric film or glass. In various embodiments, the reaction component may not require a solid upper sealing component for the substrate. The reaction component may be configured to provide an oil sealing layer for the at least one hydrophilic site for performing the nucleic acid amplification reaction. The reaction component may be configured to provide an oil sealing layer for each of the one or more hydrophilic sites. The reaction component may be configured to provide nucleic acid amplification reagents to the at least one target nucleic acid contained on the at least one hydrophilic site on the base substrate component. The reaction component may be configured to provide suitable reaction conditions to perform a nucleic acid amplification of the at least one target nucleic acid contained on the at least one hydrophilic site on the base substrate component. The system may be further configured to withdraw a volume of the at least one nucleic acid amplification reaction product from under the oil seal for identification of the at least one nucleic acid sequence by the detection component.

The detection component of the system may be selected from a fluorescent dye sequencing component, a semiconductor sequencing component, or a pyrophosphate sequencing component. In some embodiments, the detection component may be a fluorescent dye sequencing component. In some embodiments, the fluorescent dye sequencing component may be a mobility dependent fluorescent dye sequencing component. In some embodiments, the mobility dependent fluorescent dye sequencing component may be capillary electrophoresis.

In yet another aspect, the invention provides a base substrate component for nucleic acid amplification and identification, including: one or more hydrophilic sites separated by hydrophobic zones wherein at least one hydrophilic site is configured to contain at least one target nucleic acid; where the base substrate component is made of one or more materials compatible with reaction conditions of a nucleic acid amplification reaction; and further where the base substrate component is configured to permit extraction of an aliquot of an amplified target nucleic acid for detection of the nucleic acid sequence identity. The base substrate component may be polymer or glass.

In yet another aspect, a kit is provided, including a base substrate component for nucleic acid amplification and identification, including: one or more hydrophilic sites separated by hydrophobic zones wherein at least one hydrophilic site is configured to contain at least one target nucleic acid; where the base substrate component is made of one or more materials compatible with reaction conditions of a nucleic acid amplification reaction; and further where the base substrate component is configured to permit extraction of an aliquot of an amplified target nucleic acid for detection of the nucleic acid sequence identity, and optionally, instructions for its use. The kit may further include reagents for a nucleic acid amplification reaction. The kit may further include reagents for a nucleic acid sequencing reaction.

In a further aspect, a method is provided for identifying at least one target nucleic acid, encompassing the steps of: providing a base substrate component having one or more hydrophilic sites separated by hydrophobic zones wherein at least one hydrophilic site includes at least one target nucleic acid and further wherein the base substrate component is made of one or more materials compatible with reaction conditions of a nucleic acid amplification reaction; providing reagents suitable for amplification of the at least one target nucleic acid at the at least one hydrophilic site; performing a nucleic acid amplification reaction upon the at least one target nucleic acid to form at least one nucleic acid amplification product; and detecting the nucleic acid sequence of the at least one nucleic acid amplification product, thereby identifying the at least one target nucleic acid.

In some embodiments, no solid upper sealing component for the substrate may be provided. In various embodiments, the method further includes the step of providing a sealing solution layer for the at least one hydrophilic site containing the at least one nucleic acid for the nucleic acid amplification reaction. In some embodiments, the sealing solution layer may be provided for each of the one or more hydrophilic sites. In some embodiments, the method further includes the step of providing nucleic acid amplification reagents to the at least one target nucleic acid contained on the at least one hydrophilic site on the substrate. The method may further include providing suitable reaction conditions to perform a nucleic acid amplification of the at least one target nucleic acid contained on the at least one hydrophilic site on the base substrate component. In some embodiments, a volume of the at least one nucleic acid amplification reaction product is withdrawn from under the oil seal to identify the at least one nucleic acid sequence by the detection component.

In some embodiments of the method, the detection component may be selected from a fluorescent detection component, a semiconductor detection component, or a pyrophosphate detection component. In other embodiments, the detection may be a fluorescent dye sequencing component. In yet other embodiments, the fluorescent dye sequencing component may be a mobility dependent fluorescent dye sequencing component. In other embodiments, the mobility dependent fluorescent dye sequencing component may be capillary electrophoresis.

In a further aspect, the invention also provides a system for identifying a target nucleic acid, including (a) a reaction cartridge including: a lysis well configured to hold a sample substrate having a biological sample which includes the target nucleic acid and an aliquot of a lysis buffer, where the biological sample is lysed to release target nucleic acid; a PCR well configured to hold an aliquot of PCR reagents, where the released target nucleic acid is amplified to form an amplified target nucleic acid sample; a sealing solution well configured to hold an aliquot of sealing solution, where the sealing solution is transferred to the PCR well to seal the open PCR; and optionally, a transfer tip configured to transfer any of the aliquots of released target nucleic acid, sealing solution and amplified target nucleic acid sample; and optionally, a detection sample preparation well operably connected to the reaction cartridge, wherein the detection sample preparation well is configured to hold an aliquot of reagents configured to prepare the sample for identification of a nucleic acid sequence of the amplified target nucleic acid sample; and where the reaction cartridge comprises one or more materials compatible with reaction conditions of a nucleic acid amplification reaction; (b) a reaction component configured to amplify the released target nucleic acid to form the amplified target nucleic acid sample; and (c) a detection component configured to identify a nucleic acid sequence of the amplified target nucleic acid sample. In some embodiments, the reaction cartridge may be made of polymer or glass. In some embodiments, the sample substrate may be a section of a paper substrate, including but not limited to a paper punch from a paper substrate to which a biological sample has been collected, or a buccal swab. In various embodiments, the reaction cartridge may not require a solid upper closure component for the reaction cartridge. In some embodiments, the system may be configured to transfer an aliquot of the released target nucleic acid from the lysis well to the PCR well. In some embodiments, the reaction component may be configured to provide suitable reaction conditions to perform a nucleic acid amplification of the released target nucleic acid contained in the PCR well of the reaction cartridge. In various embodiments, the system may be configured to withdraw a volume of the amplified target nucleic acid sample from under the oil seal and transfer it to the detection sample preparation well to prepare the amplified target nucleic acid sample for identification of the nucleic acid sequence by the detection component. In yet other embodiments, the detection component may be selected from a fluorescent dye sequencing component, a semiconductor sequencing component, or a pyrophosphate sequencing component. In some embodiments, the detection component may be a fluorescent dye sequencing component. In some embodiments, the fluorescent dye sequencing component may be a mobility dependent fluorescent dye sequencing component. In some embodiments, the mobility dependent fluorescent dye sequencing component may be a capillary electrophoresis component. The system may further include a plurality of reaction cartridges.

In another aspect, a reaction cartridge for nucleic acid amplification and identification is provided, including (a) a lysis well configured to hold a sample substrate having a biological sample including the target nucleic acid and an aliquot of a lysis buffer, where the biological sample is lysed to release target nucleic acid; (b) a PCR well configured to hold an aliquot of PCR reagents, where the released target nucleic acid is amplified to form an amplified target nucleic acid sample; (c) a sealing solution well configured to hold an aliquot of sealing solution, where the sealing solution is transferred to the PCR well to seal the open PCR; and optionally, (d) a transfer tip configured to transfer any of the aliquots of released target nucleic acid, sealing solution and amplified target nucleic acid sample; and optionally, (e) a detection sample preparation well operably connected to the reaction cartridge, where the detection sample preparation well is configured to hold an aliquot of reagents configured to prepare the sample for identification of a nucleic acid sequence of the amplified target nucleic acid sample; and further where the reaction cartridge is made of one or more materials compatible with reaction conditions of a nucleic acid amplification reaction. In some embodiments, the reaction cartridge is made of one or more polymers, glass or a combination thereof.

In a further aspect, a kit is provided including a reaction cartridge for nucleic acid amplification and identification, including (a) a lysis well configured to hold a sample substrate having a biological sample including the target nucleic acid and an aliquot of a lysis buffer, where the biological sample is lysed to release target nucleic acid; (b) a PCR well configured to hold an aliquot of PCR reagents, where the released target nucleic acid is amplified to form an amplified target nucleic acid sample; (c) a sealing solution well configured to hold an aliquot of sealing solution, where the sealing solution is transferred to the PCR well to seal the open PCR; and optionally, (d) a transfer tip configured to transfer any of the aliquots of released target nucleic acid, sealing solution and amplified target nucleic acid sample; and optionally, (e) a detection sample preparation well operably connected to the reaction cartridge, where the detection sample preparation well is configured to hold an aliquot of reagents configured to prepare the sample for identification of a nucleic acid sequence of the amplified target nucleic acid sample; and further where the reaction cartridge is made of one or more materials compatible with reaction conditions of a nucleic acid amplification reaction, and optionally, instructions for its use. In some embodiments, the reaction cartridge of the lot is made of one or more polymers, glass or a combination thereof. In various embodiments, the kit may further include reagents for a nucleic acid amplification reaction. In various embodiments the kit may further include a sealing solution. In some other embodiments, the kit may further include reagents for a nucleic acid sequencing reaction.

In another aspect, a method of identifying a target nucleic acid is provided, including the steps of: (a) providing a reaction cartridge including: a lysis well configured to hold a sample substrate comprising a biological sample comprising the target nucleic acid and an aliquot of a lysis buffer, where the biological sample is lysed to release target nucleic acid; a PCR well configured to hold an aliquot of PCR reagents, where the released target nucleic acid is amplified to form an amplified target nucleic acid sample; a sealing solution well configured to hold an aliquot of sealing solution, where the sealing solution is transferred to the PCR well to seal the open PCR; and optionally, a transfer tip configured to transfer any of the aliquots of released target nucleic acid, sealing solution and amplified target nucleic acid sample; and optionally, a detection sample preparation well operably connected to the reaction cartridge, where the detection sample preparation well is configured to hold an aliquot of reagents configured to prepare the sample for identification of a nucleic acid sequence of the amplified target nucleic acid sample; and where the reaction cartridge includes one or more materials compatible with reaction conditions of a nucleic acid amplification reaction; (b) providing reagents suitable for amplification of the released target nucleic acid in the PCR well of the reaction cartridge; (c) sealing the PCR well with an aliquot of the sealing solution; (d) performing a nucleic acid amplification reaction upon the released target nucleic acid to form the amplified target nucleic acid sample; and (e) detecting the nucleic acid sequence of the amplified target nucleic acid sample, thereby identifying the at least one target nucleic acid. In some embodiments, the reaction cartridge may be polymeric film or glass. In some embodiments the sample substrate may be a section of a paper substrate or a buccal swab. In various embodiments, the method may further include the step of adding the sample substrate including the biological sample containing the target nucleic acid to the lysis well, and lysing the biological sample to release the target nucleic acid. In other embodiments, the method may further include the step of transferring an aliquot of the released target nucleic acid from the lysis well to the PCR well with the transfer tip after the biological sample has been lysed to release target nucleic acid. In various embodiments, no solid upper sealing component for the substrate may be provided. In some embodiments, the method may further include the step of transferring the sealing solution with the transfer tip to the PCR well of the reaction cartridge containing the released nucleic acid and the aliquot of PCR reagents. In some embodiments, the method may further include the step of providing suitable reaction conditions to amplify the released target nucleic acid contained in the PCR well of the reaction cartridge to form the amplified target nucleic acid sample. In some embodiments, a volume of the amplified target nucleic acid sample may be withdrawn from under the oil seal with the transfer tip and transferred to the detection sample preparation well. In other embodiments, the detection component may be selected from a fluorescent dye sequencing component, a semiconductor sequencing component, or a pyrophosphate sequencing component. In yet other embodiments, the detection component may be a fluorescent dye sequencing component. In some embodiments, the fluorescent dye sequencing component may be a mobility dependent fluorescent dye sequencing component. In some embodiments, the mobility dependent fluorescent dye sequencing component may be a capillary electrophoresis component. In some embodiments, the aliquot of reagents configured to prepare the sample for identification of a nucleic acid sequence of the amplified target nucleic acid sample may include a denaturant. The denaturant may be formamide. In some embodiments, the aliquot of reagents further include a size standard.

In the following description, certain aspects and embodiments will become evident. It should be understood that a given embodiment need not have all aspects and features described herein. It should be understood that these aspects and embodiments are merely exemplary and explanatory and are not restrictive of the invention.

There still exists a need for improved systems, kits, and methods for collecting fingerprint, toe print, hand palm prints or foot sole prints and biological sample data for purposes of identifying and confirming the identity of a human individual.

BRIEF DESCRIPTION OF THE DRAWINGS

FIGS. 1A and 1B illustrates a system for the simultaneous collection of the ridge and valley signature of an appendage and a biological sample from an individual, in accordance with various embodiments.

DETAILED DESCRIPTION

Figure 2:
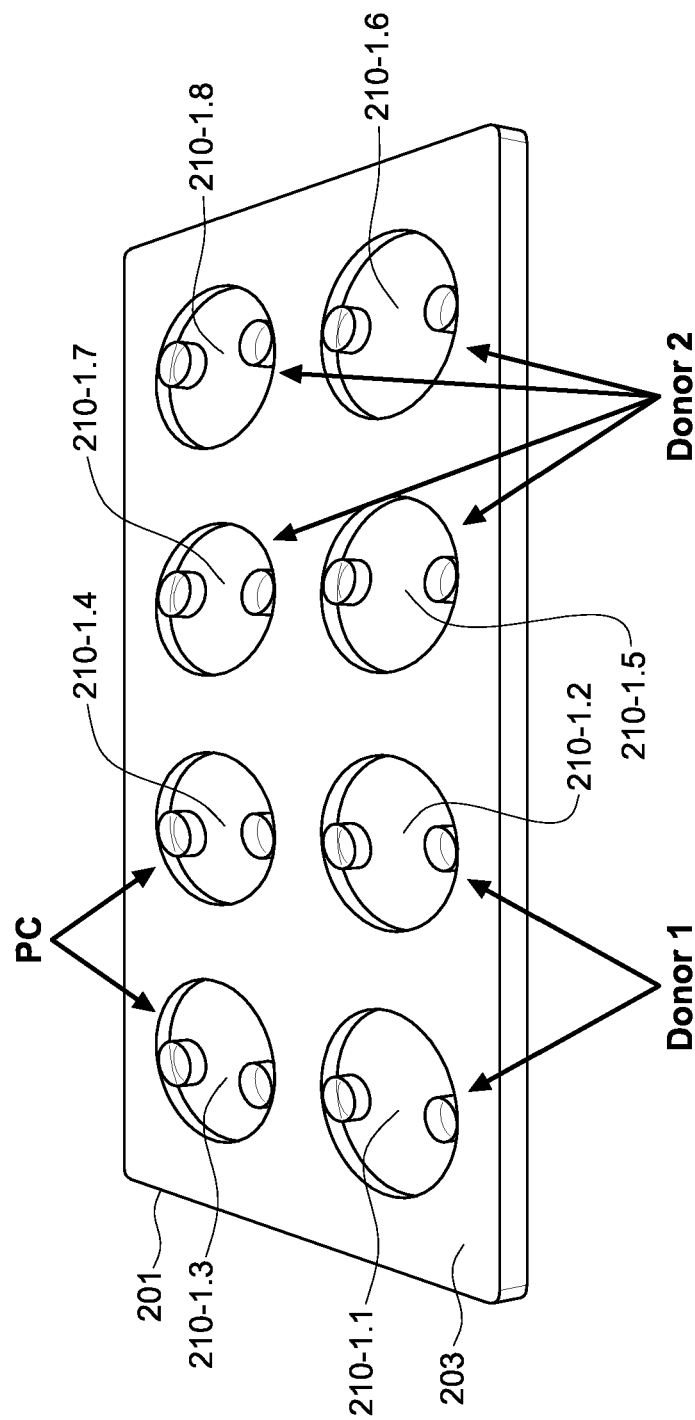
FIG. 2 illustrates a device for the simultaneous collection of the ridge and valley signature of an appendage and a biological sample from an individual, also showing its compatibility for use in nucleic acid amplification without transfer of the biological sample.

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, "DNA" and "nucleic acid" are used interchangeably.

As used herein "oligonucleotide" and "polynucleotide" are interchangeable and generally refers to a polymer of nucleotide subunits having a fragment size of about or less than 200 base pairs.

As used herein, "biological sample" refers to a component originating from either within or on the body of an individual.

As used herein, "body fluid" refers to liquids originating within the body of an individual.

As used herein, "digital imaging apparatus" refers to an apparatus capable of digitizing an image of an object.

As used herein, "DNA sequencing" refers to the determination of the sequential identity of nucleotides in a molecule of DNA.

As used herein, "filter paper" refers to a semi-permeable paper.

As used herein, "a housing" refers to a structure surrounding at least in part an apparatus capable of performing a physical movement or carrying out a physical action including but not limited to illuminating, scanning and the like.

As used herein, "identifier" refers to a label capable of use in cataloging/correlating like-labeled data or data from a single source.

As used herein, "image capturing device" refers to a type of camera or scanning device.

As used herein, "imaging component" refers to an apparatus capable of performing at least one of capturing, developing, storing, retrieving and transmitting an image.

As used herein, "Indel" refers to an insertion or deletion of a segment of nucleic acid, usually DNA, within a nucleic acid sequence.

As used herein, "isolated" refers to separation of nucleic acid from either or both naturally occurring materials or environmental chemicals/substances.

As used herein, "light emitting diodes" refers to LEDs, a semiconductor light source.

As used herein, "multispectral illuminator" refers to a plurality of frequencies/wavelengths across the electromagnetic spectrum used to capture image data.

As used herein, "open PCR" refers to a polymerase chain reaction amplification of nucleic acid performed in a reaction vessel that has no solid upper enclosure. The reaction takes place under a sealing layer isolating the reaction mixture from the environment. The sealing layer conveniently may be added over the reaction mixture of target nucleic acid and the PCR reagents or the sealing layer may be added over the target nucleic acid and the PCR reagents added through the sealing layer to the target nucleic acid. Typically, the sealing layer is a liquid, including but not limited to an oil such as mineral oil.

As used herein, "optically collecting" refers to obtaining data, such as a ridge and valley signature or an image through illuminating the data or image and capturing the result.

As used herein, "appendage" refers to one of several most distal parts of a limb, and includes a finger or toe.

As used herein, "photographic apparatus" refers to an LED camera, a digital camera, a still camera, a video camera and a virtual camera.

As used herein, "polymerase chain reaction" or PCR is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, The Polymerase Chain Reaction, BirkHauser, Boston, Mass. (1994)). Each of the above steps may be conducted at a different temperature, preferably using an automated thermocycler (Applied Biosystems LLC, a division of Life Technologies Corporation, Foster City, Calif.). If desired, RNA samples can be converted to DNA/RNA heteroduplexes or to duplex cDNA by methods known to one of skill in the art. The PCR method also includes reverse transcriptase-PCR and other reactions that follow principles of PCR.

As used herein, "ridge and valley signature" refers to the friction ridges also known as surface contours on the palmar surface of the fingers, surface of the palm and hand and plantar surface of the feet and toes. In particular, the friction ridges provided by the impressions made from imaging one or more fingers are known as fingerprints.

As used herein, "SNP analysis" refers to the evaluation of the presence or absence of a single nucleotide polymorphism (SNP) marker following amplification of the locus containing the SNP marker As used herein, "STR analysis" refers to the evaluation of the alleles of a short tandem repeat (STR) marker following amplification of the locus containing the STR marker.

As used herein, "succession" refers to a sequence of steps performed.

As used herein, "topological impression" refers to the ridge and valley topography of a finger, palm, toe or foot.

Reference will now be made to various embodiments, examples of which are illustrated in the accompanying drawings.

Improvements are needed for collection of biological samples containing nucleic acid while also obtaining biometric information such as a fingerprint. In particular, it is advantageous to obtain the biological sample non-invasively. It has been found that, under suitable conditions, when a ridge and valley signature of an appendage of an individual is imaged through a substrate and scanning surface, that sufficient nucleic acid is deposited when the appendage contacts the substrate, to provide a DNA profile having sufficient signal to identify the individual. In some embodiments, devices, systems, and methods are disclosed to analyze the biological sample, once deposited upon a substrate, by further processing such as direct amplification of the nucleic acid without transfer of the nucleic acid or the biological sample to any other receptacle or receiving surface. The processing, including nucleic acid amplification, nucleic acid sequencing reaction, and, optionally lysis, of the collected nucleic acid on the substrate itself permits direct PCR amplification in a very small volume which can provide increased sensitivity and simplified workflows. Further simplification has been demonstrated by performing amplification of the nucleic acid directly on the substrate without requiring a solid covering to the reaction well, i.e., performing open PCR, by using a sealing solution layer over the mixture of the amplification reagents and deposited nucleic acid. No additional manipulation of the collected nucleic acid may be needed, additionally preventing loss of limited amounts of the nucleic acids provided in the biological sample.

The devices, systems, kits and methods described here provide the ability to perform direct amplification of fingerprint nucleic acid on the same substrate on which the fingerprint is collected. This improvement enhances the integrity of chain of custody and reduces the likelihood of sample handling errors which may occur when fingerprint nucleic acid is transferred from a substrate having a fingerprint nucleic acid deposit to a PCR reaction vessel.

The improvement offered by the open PCR format affords adaptability of automated operation and allows simple recovery of a PCR product through a sealing solution layer by a simple pipetting operation.

Further, the small thermal cycler footprint and weight make it an ideal PCR module in a fully integrated STR typing or other identification system. The AmpliSpeed slide thermal cycler used in this study weighs only 2.9 kg with dimension of only about 126 mm×about 295 mm×about 112 mm.

System.

Systems are described here for collection of a biological sample containing nucleic acid and at least one ridge and valley signature of an individual, which include at least a first imaging component having a scanning surface configured to permit an energy wave to penetrate the scanning surface, where the energy wave is configured to image the at least one ridge and valley signature of an appendage of the individual; and a device having a base substrate component having at least a first surface area, where the at least first surface area is transparent or translucent to an energy wave capable of imaging at least one ridge and valley signature of an appendage of the individual; configured to collect the biological sample from the appendage; and made of one or more materials compatible with reaction conditions of a nucleic acid amplification reaction. The system is configured to collect at least one ridge and valley signature by imaging the appendage through the scanning surface and the base substrate component of the device while the appendage is positioned upon the at least first surface area of the base substrate component. The biological sample including at least one nucleic acid is collected from the skin of the appendage of the individual. The skin is a complicated organ and includes more than one layer of cell and tissue type. The epidermis refers to the tissues on the surface of human or animal skin and includes materials secreted therefrom or derived from the lower layers of the skin, from which DNA can be easily obtained for use in identifying the individual. The outermost layer of the skin is the stratum corneum. Below the epidermis layer of the skin is the dermis layer containing fibroblasts, macrophages and adipocytes, three cell types each having a nucleus containing nucleic acid. In addition the dermis has a vascular network of blood veins, arteries and lymph vessel containing white blood cells having a nucleus as does the erector pili muscle tissue, sebaceous glands and body fluids also present within the dermis. Additionally, sweat glands and vessels in the dermis may contain genetic materials in the form of intact cells or as free DNA, which may be released up to the epidermis for collection by the systems and methods of the invention. Any or all of these nucleic acid containing materials are encompassed by the biological sample. In various embodiments of the invention, collecting the biological sample is non-invasive.

The system may collect simultaneously at least one ridge and valley signature of an individual and a biological sample containing nucleic acid or may collect in succession the signature and biological sample or, visa versa, the biological sample and the signature with an at least first imaging component. The methods of collection provide collection of both the biological sample and the at least one ridge and valley signature while the individual may touch only one apparatus. Additional motions or steps of touching additional platens or substrates may not be required to collect the biological sample and the at least one ridge and valley signature. The ridge refers to a friction ridge, the raised part of the epidermal layer of the skin of the fingers, toes, palm of the hand or sole of the foot and the valley being the depression in the epidermis between two adjacent ridges. The ridges and valleys are commonly referred to as fingerprints, palm prints, toe prints or footprints depending on the origin of the ridge and valley signature.

The system may further include nucleic acid amplification reaction component, where the reaction component is configured to subject the device containing the biological sample on the base substrate component to a nucleic acid amplification reaction. In some embodiments, wherein the system provides a reaction component, the reaction component provides a sealing solution for the nucleic acid amplification reaction. The use of a sealing solution to isolate the reaction mixture from the environment, without using a physical cover to the reaction well may provide streamlined workflows. In some embodiments, the system includes a nucleic acid reaction component that is further configured to subject the device to a nucleic acid sequencing reaction.

The system may further include a component, where the detection component is configured to detect at least one product of the nucleic acid amplification, thereby identifying a corresponding sequence of the at least one nucleic acid amplification product. In some embodiments, the identification of the at least one nucleic acid amplification product sequence provides a nucleic acid sequence identification of the individual.

The system may further include a processor configured to transmit the ridge and valley signature of the individual to at least one database comprising ridge and valley signatures selected from the group consisting of a forensic, criminal, identity, child identity, missing persons, immigration, department of motor vehicles, terrorist, paternity, arrestee, convict database, access control and any combination thereof. The system may further include a processor configured to transmit the nucleic acid sequence identity of the individual to at least one database comprising nucleic acid sequence identities selected from the group consisting of a forensic, criminal, identity, child identity, missing persons, immigration, department of motor vehicles, terrorist, paternity, arrestee, convict database, access control and any combination thereof.

In various embodiments, the system collects at least one ridge and valley signature of an individual and a biological sample containing nucleic acid simultaneously or collects in succession the signature and biological sample or, visa versa, the biological sample and the signature with the at least first imaging system, while requiring the individual to touch an apparatus only once.

At Least a First Imaging Component.

In various embodiments, the system includes at least a first imaging component configured to obtain a ridge and valley signature of the individual. The imaging component may employ energy waves, such as light as described above, or other energy waves such as electromagnetic waves, capacitance, infra-red or sonic, e.g., ultrasound based components to provide an image of the ridge and valley signature. When the term imaging component is used in the context of capturing ridge and valley signatures, this includes any component that captures a digital or analog electronic representation of ridge and valley signatures.

Ridge and valley signatures may also be obtained using a touchless three-dimensional ridge and valley scanner using a digital processing means. (Wang, Yongchang; Q. Hao, A. Fatehpuria, D. L. Lau and L. G. Hassebrook (2009). "Data Acquisition and Quality Analysis of 3-Dimensional Fingerprints". Florida: IEEE conference on Biometrics, Identity and Security. http://vis.uky.eduhrealtime3d/Doc/3D_Fingerprint_Quality.pdf. Retrieved March 2010. Wang, Yongchang; D. L. Lau and L. G. Hassebrook (2010). "Fitsphere unwrapping and performance analysis of 3D Fingerprints". Applied Optics. pp. 592-600).

In one embodiment of the present teachings, the system may include at least a first optical imaging component. In other embodiments, the system can include at least a first solid-state ridge and valley signature reader. The optical imaging component has an illuminating means for optically collecting the ridge and valley signature using an optical scanner as is known to one of skill in the art. The optical scanner can be an array of a plurality of light emitting diodes or a multispectral illuminator. The optical scanner may be a camera, an active pixel imager, a CMOS imager, an imager that images in multiple wavelengths, a CCD camera, a photo detector array, or a TFT imager. In an optical scanner a beam of light passes through scanning surface to illuminate the topological impression made by the appendage, including a finger, hand, palm, toe, sole or foot, when positioned against the scanning surface of the at least first imaging component.

Any suitable instrumentation may be used to acquire the image of an appendage according to the methods described herein. Some instruments and techniques include but are not limited to those disclosed in U.S. Pat. Nos. 4,537,484, 6,175,407, 6,665,427, 8,014,581, 8,036,431, 5,177,353, 6,282,303, 6,188,781, 6,741,729, 6,122,394, 6,826,000, 6,496,630, 6,628,813, 6,983,062, 7,162,060, 7,164,440, 7,657,067, 8,073,209, 7,190,817, 7,558,410, 7,565,541, 7,995,808, 7,899,217, 7,890,158, 7,835,554, 7,831,072, 7,819,311, 7,804,984, 7,801,339, 7,801,338, 7,751,594, 7,735,729, 7,668,350, 7,627,151, 7,620,212, 7,613,504, 7,545,963, 7,539,330, 7,508,965, 7,460,696, 7,440,597, 7,394,919, 7,386,152, 7,347,365, 7,263,213, 7,203,345, 7,147,153, 6,816,605, 6,628,809, 6,560,352, US20110235872, US20110211055, US20110165911, US20110163163, US20110085708, US20100246902, US20100067748, US20090245591, US20090148005, US20090092290, US20090080709, US20090046903, US20080304712, US20080298649, US20080297788, US20080232653, US20080192988, US20080025580, US20080025579, US20070116331, US20070030475, US20060274921, US20060244947, US20060210120, US20060202028, US20060110015, US20060062438, US20060002598, US20060002597, US20050271258, US20050265586, US20050265585, US20050205667, US20050185847, US20050007582, US20040240712, US20040047493, US20030223621, US20030078504, US20020183624, or US20020009213.

Scanning Surface.

The at least first imaging component includes a scanning surface configured to permit the energy wave to penetrate the scanning surface, to image the at least one ridge and valley signature of an appendage of the individual positioned on at least a portion of the scanning surface. The scanning surface may be transparent or translucent to the energy wave used to image the at least one ridge and valley signature. The scanning surface may be formed from a material selected from a plastic, a polyolefin, a polystyrene, a metal, a metal alloy, a glass, a silicon or combinations thereof. In some embodiments, the surface may include derivatized plastic, derivatized polyolefin, derivatized polystyrene, derivatized metal, derivatized metal ally, derivatized glass, derivatized silicon or combination of materials.

Device.

A device is provided for collection of a biological sample comprising nucleic acid from an individual, where the device has a base substrate component having at least a first surface area, where the at least first surface area is transparent or translucent to an energy wave capable of imaging at least one ridge and valley signature of an appendage of the individual; configured to collect the biological sample from the appendage; and made of one or more materials compatible with the reaction conditions normally used in a nucleic acid amplification reaction. The materials may further be compatible with nucleic acid sequencing reaction conditions.

Base Substrate Component.

The base substrate component has at least a first surface area, where the at least first surface area is transparent or translucent to an energy wave capable of imaging at least one ridge and valley signature of an appendage of an individual; configured to collect a biological sample containing nucleic acid from the appendage; and is made of one or more materials compatible with reaction conditions of a nucleic acid amplification reaction. Once the biological sample containing nucleic acid is collected to the base substrate component, a nucleic acid amplification reaction may be performed upon the nucleic acid as deposited upon the substrate, thus requiring no transfer or additional handling of the nucleic acid. The in-situ amplification provides workflow simplification, less opportunity for sample mishandling and higher probability of obtaining robust amplification results from limited sample quantities, while obtaining the biological sample in a one step, non-invasive procedure. The base substrate component may be any suitable polymeric film or glass. In some embodiments, the at least first surface area of the base substrate component may be transparent or translucent to the energy wave imaging the ridge and valley signature. In other embodiments, all the surface areas of the base substrate component may be transparent or translucent to the energy wave. In some embodiments, the base substrate component is substantially transparent to the energy wave. In other embodiments, all of the surface areas of the base substrate component may be compatible with nucleic acid amplification reaction conditions. In various embodiments, the at least first surface area of the base substrate component may be hydrophilic. In other embodiments, the at least first surface area of the base substrate component may be treated with a PCR compatible adhesive to aid in capturing the biological sample. In various embodiments, the base substrate component may further include a second surface area surrounding the first surface area. The second surface area of the base substrate component may be hydrophobic.

Figure 16:
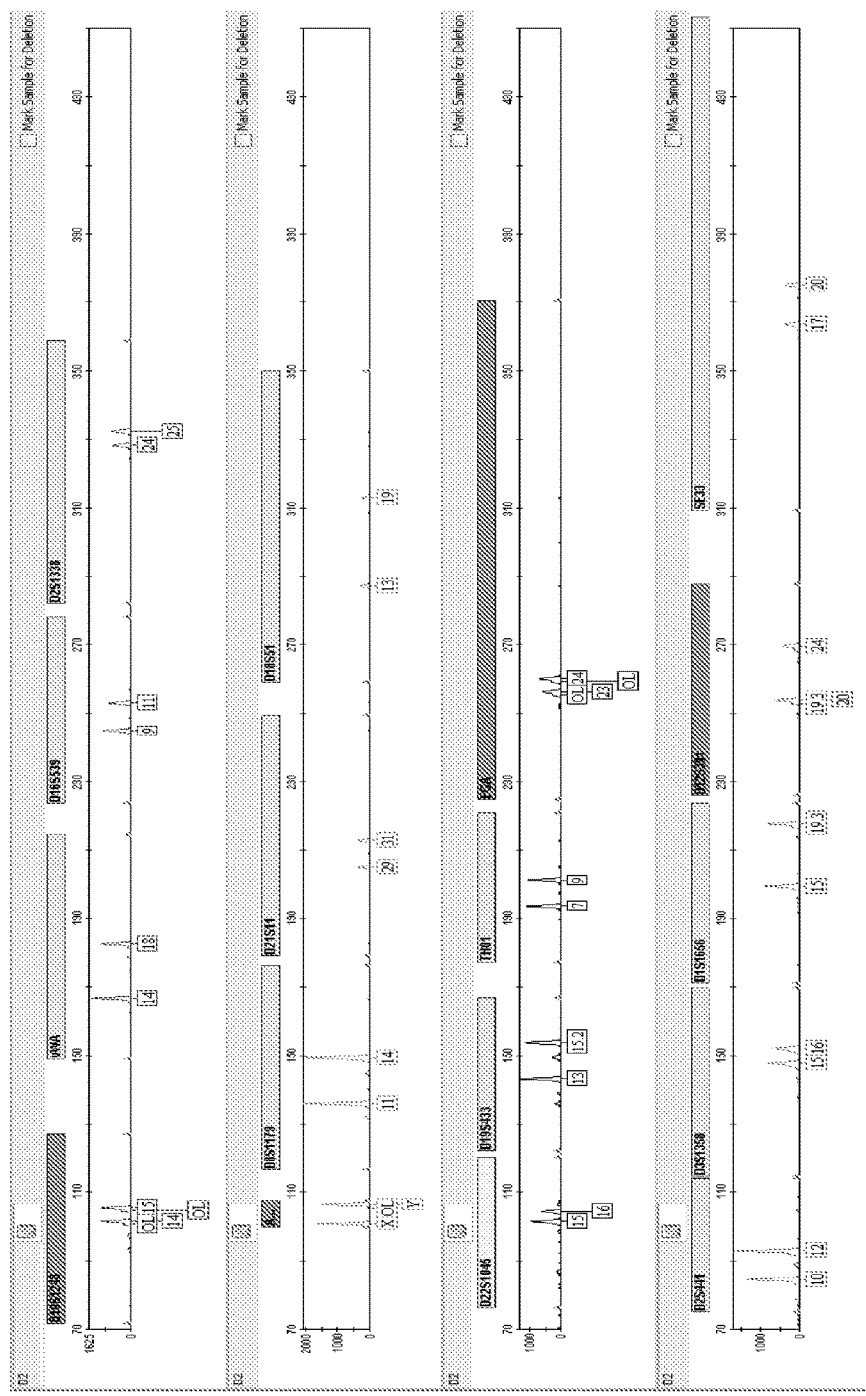
FIG. 16 is a graphical representation of a STR analysis of nucleic acid collected from an individual using another variation of the device of FIGS. 14A and 14B.

In FIG. 1A, a finger 101 rests on base substrate component 110A positioned above a scanning surface for the collection of a biological sample containing nucleic acid and a ridge and valley signature onto substrate 110A. In some embodiments, the fingerprint containing the biological sample containing nucleic acid is deposited within a first surface area 1106-1, which may be about 20 mm wide (FIG. 16). The surrounding surface area 1106-2 may have the same surface characteristics as the first surface area 110B-1 or it may be modified to have different properties.

Polymeric Film Base Substrate Component.

In various embodiments, the base substrate component may be a polymeric film. In some embodiments, the polymeric film may be dimensionally stable enough to maintain structural integrity upon the scanning surface. In other embodiments, the polymeric film may be attached upon or to a support. Useful polymeric films include natural polymeric materials, which include but are not limited to starch, agarose, alginate, carrageenan or synthetic polymer gel, or a mixture thereof.

Synthetic polymers may also be used as the base substrate component. To form the polymeric film that may be used as a base substrate component, all types of polymerization, including cationic, anionic, copolymerization, chain copolymerization, cross-linking, uncrosslinked polymerization, and the like can be employed to synthesize the polymer gels forming part or all of the base substrate component. Essentially any type of polymer or copolymer formable from a fluid precursor, including but not limited to homopolymers, random copolymers, terblock polymers, radial polymers, linear polymers, branched polymers, and graft copolymers, can be incorporated as part or all of the base substrate component. An exemplary, non-limiting list of polymers that are suitable include cellulose polymers, including but not limited to hydroxyethylcellulose (HEC), hydroxypropyl methylcellulose (HPMC), hydroxypropyl cellulose (HPC); derivatives of sugars including but not limited to dextrans, mannitols, and gluco-pyranosides; pluronic copolymer liquid crystals; polyurethane; polyacids, including but not limited to lactic acids, and acrylic acids; polyamides; polyacrylamides, including but not limited to unsubstituted, N-substituted, and N, N-disubstituted acrylamides; polycarbonates; polyacetylenes; polydiacetylenes; polyphosphazenes; polysiloxane; polyolefins; polyesters; polyethers; poly(ether ketones); poly(alkylene oxides), including but not limited to polyethyleneoxides (PEO), polyethylethylene glycols (PEG) and polypropylene oxides (PPO); poly(ethylene terephthalate); poly(methyl methacrylate); polystyrene; substituted polystyrene, including but not limited to polystyrene sulfonates (PSS) and polyanetholes (PASA); poly(vinylpyrrolidones); proteinaceous material, and/or combinations and/or copolymers of the above.

In some embodiments, the polymeric film base substrate component may be selected from commercially available films, including but not limited to 3M PP2200, 3M PP2500, 3M CG600, or 3M CG3300. Many types of commercially available film may be suitable for use as a substrate, having no interference or substantially not interfering with the fingerprinting process. Suitable films have the ability to retain DNA on the film when the appendage of the individual contacts the film to image the ridge and valley signature. Other suitable films permit direct amplification of the DNA of the collected biological sample in the presence of the film. Yet other suitable films permit the at least one nucleic acid of the biological sample to be rinsed from the surface of the film, to be amplified thereafter.

In some embodiments, the polymeric film base substrate component has no modifications made to the polymeric film.

Glass Base Substrate Component.

In other embodiments, the base substrate component may be made of glass, and may be made of any suitable glass material that will permit the energy wave to penetrate the substrate to image the ridge and valley signature of the appendage of the individual, collect the biological sample, and have compatibility with nucleic acid amplification reaction conditions. Many types of commercially available glass may be suitable for use as a base substrate component, having no interference or substantially no interference with the fingerprinting process. Suitable glass has the ability to capture DNA on the glass when the appendage of the individual contacts the glass to image the ridge and valley signature. Some suitable glasses permit transfer of the biological sample containing the DNA, once collected, to another substrate. In some embodiments, a glass substrate will permit transfer of the at least one nucleic acid of the biological sample from the base substrate component while retaining other components of the biological sample. Other suitable glasses permit direct amplification of the DNA of the collected biological sample in the presence of the glass. Yet other suitable glasses permit the collected biological sample containing the DNA to be rinsed from the surface of the glass, to be amplified thereafter.

Surface Modifications of the Polymeric or Glass Base Substrate Component.

The base substrate component may have one or more surface areas that have modifications. The at least first surface area of the base substrate component may be treated with PCR compatible adhesive to aid in collection of the biological sample, or it may be hydrophilic. A glass base substrate component may be treated with a reagent to create a hydrophobic surface area surrounding the surface area where the finger of the individual contacts and deposits the biological sample during imaging of the fingerprint. A hydrophobic second surface area may be made by treating glass with a reagent including, but not limited to a silanizing reagent. The hydrophobic second surface area of the base substrate component may assist in retaining the nucleic acid amplification reagents within the first surface area containing the deposited nucleic acid during the amplification reaction. In some embodiments, the base substrate component is modified to be adhesive. The adhesive may be PCR compatible. In other embodiments, the polymeric film is tackified, assisting in collection of the biological sample, without leading to physical handling difficulties.

In some embodiments, the base substrate component may be modified with chemically reactive groups to permit ionic, covalent or hydrogen bond interactions with species present within the biological sample. Suitable chemically reactive groups that may modify a base substrate component include but are not limited to thiols, amines, carboxylic acids or the like, as is generally known in the art. Some examples of chemical modifications include, but are not limited to, amino groups including aliphatic and aromatic amines, carboxylic acids, aldehydes, amides, chloromethyl groups, hydrazide, hydroxyl groups, sulfonates and phosphates. These functional groups can be used to add any number of modifications to the polymeric or glass base substrate component, generally using known chemistries, including, but not limited to the use of amino-functionalized linkers, sulfhydryl linkers, etc. There are a number of sulfhydryl reactive linkers known in the art such as SPDP, maleimides, alpha-haloacetyls, and pyridyl disulfides. Similarly, amino groups on the polymeric or glass base substrate component can be attached using linkers; for example, a large number of stable bifunctional groups are well known in the art, including homobifunctional and heterobifunctional linkers. In an additional embodiment, carboxyl groups on the base substrate component can be derivatized using well-known linkers. For example, carbodiimides activate carboxyl groups for attack by good nucleophiles such as amines.

In some embodiments, the chemical modification of the base substrate component is performed to attach, covalently or noncovalently, a reagent, including but not limited to an enzyme, a binding partner, a surfactant, an anionic polymer or a zwitterionic species to assist in the collection of DNA from the subject. In some embodiments, the chemical modification may introduce electrically conductive polymers to the base substrate component, to assist in collection of DNA from the subject. If conductive polymers form part of the base substrate component, the system may further provide suitable electrical flow across the base substrate component to provide ionotophoretic assistance to drive charged nucleic acids from the appendage to the base substrate component, when the appendage is in contact with the base substrate component and the electrical circuit is completed.

In yet other embodiments, when a base substrate component is modified chemically to covalently attach one or more reagents, an enzyme, including but not limited to proteinase K may be attached to the base substrate component to assist in extracting nucleic acids from the appendage or from the biological sample once collected. In other embodiments, an enzyme is covalently attached to the base substrate component, and may be a proteinase selected from the group consisting of keratinase, papain, bromelain, and proteinase K. In other embodiments, the base substrate component is modified covalently to attach a charged polymer to assist in extracting nucleic acids from the appendage or from the biological sample once collected. In yet other embodiments, a surfactant is associated with the base substrate component noncovalently to assist in extracting nucleic acids from the appendage or from the biological sample once collected. In some embodiments, a zwitterionic species may be present in the base substrate component to assist in separating nucleic acids from other components of the cells collected. In some other embodiments, the base substrate component is chemically modified to covalently attach an antibody to a target moiety present on the skin of the appendage or in the collected biological sample, thus providing a binding partner to the target moiety. In some embodiments, wherein a binding partner is immobilized on the base substrate component, cleavage of the binding partner along with or separately from its binding target moiety may be performed.

Frame Component.

The device also may include a frame for the base substrate component. In some embodiments, the device may be configured to permit the collection of the at least one ridge and valley signature through the frame and the base substrate component. The frame may be made of any material capable of forming a solid frame. A suitable material for a frame may have any of a variety of properties depending upon the particular embodiments, including for example, porous, nonporous, rigid, elastic, pliable, malleable, and/or chemically resistant to one or more solvents commonly used in the reactions set forth herein. In some embodiments, the frame is formed from a material selected from a polymer, a metal, a metal alloy, a glass, a silicon material or combinations thereof. Suitable polymers include but are not limited to, plastic; polypropylene, polyethylene, polybutylene, polyurethane, nylon, polymer such as acrylic, acrylonitrile butadiene styrene (ABS), ULTEM (Polyetherimide), acetal copolymer, PROPYLUX HS (heat stabilized polypropylene), RADEL A (polyethersulfone), RADEL R (polyarylethersulfone), UDEL (polysulfone), NORYL PPO (polyphenylene oxide & styrene), Polycarbonate, UHMW-PE (ultra high molecular weight polyethylene), Polyetheretherketone (PEEK), polyphenylene sulfide (PPS, TECHTRON or RYTON), polyolefin or polystyrene; metal such as aluminum, iron, steel or an alloy; other materials such as glass or silicon, or derivatives or combinations of these or other suitable materials. In some of the embodiments of the present teachings, the frame is made of a material that is transparent or translucent.

Mask Component.

The device may include a mask component configured to attach to the base substrate component. The attachment may be permanent, including but not limited to bonding via adhesives or hinged attachment allowing repositioning after deposition of the biological sample. The attachment of the mask component to the base substrate component may be made after the biological sample is deposited to the base substrate component. The mask component may surround the at least first surface area of the base substrate component, while leaving the at least first surface area of the base substrate component accessible for addition of nucleic acid amplification reaction reagents, sealing layers and sampling for detection, amongst other actions. The mask component may have a through hole to create the PCR reaction well, once bonded to the base substrate component, where the through hole surrounds the at least first surface area of the base substrate component where nucleic acid has been deposited. The mask component may be made of one or more materials compatible with reaction conditions of a nucleic acid amplification reaction. The mask component may be made of one or more polymeric materials or glass materials.

Polymer Mask Component.

In various embodiments, the base substrate component may be a polymer. Useful polymers include natural polymeric materials, which include but are not limited to starch, agarose, alginate, carrageenan or synthetic polymer gel, or a mixture thereof.

Synthetic polymers may also be used as the mask component. To form the polymer that may be used as a mask component, all types of polymerization, including cationic, anionic, copolymerization, chain copolymerization, cross-linking, uncrosslinked polymerization, and the like can be employed to synthesize the polymer gels forming part or all of the mask component. Essentially any type of polymer or copolymer formable from a fluid precursor, including but not limited to homopolymers, random copolymers, terblock polymers, radial polymers, linear polymers, branched polymers, and graft copolymers, can be incorporated as part or all of the mask component. An exemplary, non-limiting list of polymers that are suitable include cellulose polymers, including but not limited to hydroxyethylcellulose (HEC), hydroxypropyl methylcellulose (HPMC), hydroxypropyl cellulose (HPC); derivatives of sugars including but not limited to dextrans, mannitols, and gluco-pyranosides; pluronic copolymer liquid crystals; polyurethane; polyacids, including but not limited to lactic acids, and acrylic acids; polyamides; polyacrylamides, including but not limited to unsubstituted, N-substituted, and N, N-disubstituted acrylamides; polycarbonates; polyacetylenes; polydiacetylenes; polyphosphazenes; polysiloxane; polyolefins; polyesters; polyethers; poly(ether ketones); poly(alkylene oxides), including but not limited to polyethyleneoxides (PEO), polyethylethylene glycols (PEG) and polypropylene oxides (PPO); poly(ethylene terephthalate); poly(methyl methacrylate); polystyrene; substituted polystyrene, including but not limited to polystyrene sulfonates (PSS) and polyanetholes (PASA); poly(vinylpyrrolidones); proteinaceous material, and/or combinations and/or copolymers of the above. A mask component may be a natural or a synthetic rubber, latex, or vinyl polymer.

In some embodiments, the polymer mask component may be selected from commercially available films, including but not limited to 3M PP2200, 3M PP2500, 3M CG600, or 3M CG3300. Many types of commercially available polymers may be suitable for use as a mask component, having no interference or substantially not interfering with the fingerprinting process. Some suitable polymers have the ability to retain DNA on the polymer when the appendage of the individual contacts the polymer while imaging the ridge and valley signature. Other suitable polymers permit direct amplification of the DNA of the collected biological sample in the presence of the polymers. Yet other suitable polymers permit the at least one nucleic acid of the biological sample to be rinsed from the surface of the polymer mask component, to be amplified thereafter.

In some embodiments, the polymer mask component has no modifications made to the polymer.

Glass Mask Component.

In other embodiments, the mask component may be made of glass, and may be made of any suitable glass material that will not interfere with imaging of the ridge and valley signature of the appendage of the individual, and have compatibility with nucleic acid amplification reaction conditions. Many types of commercially available glass may be suitable for use as a mask component, having no interference or substantially no interference with the fingerprinting process. Some suitable glass has the ability to capture DNA on the glass during imaging of the ridge and valley signature. Other suitable glasses permit direct amplification of the DNA of the collected biological sample in the presence of the glass. Yet other suitable glasses permit the collected biological sample containing the DNA to be rinsed from the surface of the glass, to be amplified thereafter.

Surface Modifications of the Polymer or Glass Mask Component.

The mask component may have one or more surface areas that have modifications. The lower surface of the mask may have adhesive in order to bond to the base substrate component, where the bonding may occur prior to ridge and valley signature imaging and biological sample deposition, or after. The upper surface of the mask may have adhesive properties to collect additional amounts of biological samples, as portions of the finger contacting areas outside of the at least first surface area of the base substrate component may deposit additional nucleic acid. The upper surface of the mask may have adhesive for bonding to another layer to create combination mask/cover component. Alternatively, the mask component may have adhesive to bond to a ring component that assists in retaining the nucleic acid amplification reagents in place during open PCR. The upper surface of the mask component may be treated to be hydrophobic in order to retain the nucleic acid amplification reaction in place during open PCR of the nucleic acids in-situ on the base substrate component. When the mask component is glass, the upper surface of the glass mask component may be treated with a reagent to create a hydrophobic surface area surrounding the surface area where the nucleic acid has been deposited. The hydrophobic surface may be made by treating glass with a reagent including, but not limited to a silanizing reagent. The hydrophobic second surface area of the base substrate component may assist in retaining the nucleic acid amplification reagents within the first surface area containing the deposited nucleic acid during open PCR.

Cover Component.

The device may further include a cover component configured to protect the base substrate component, the mask component or both before and after collection of the ridge and valley signature and the biological sample. The cover component may also be present, in some embodiments, during the nucleic acid amplification reaction. In other embodiments, for example, when performing open PCR, the cover component is not present and the reaction mixture is protected from the environment by the sealing solution layer.

The cover component may be made of any suitable material, either polymeric or glass. In some embodiments, the cover component is transparent or translucent. In other embodiments, the cover component is made of materials compatible with PCR conditions. In some embodiments, the cover component has adhesive on its lower surface for bonding to a mask component to form a combination mask/cover component which may define a reaction well for the in-situ PCR on the base substrate component. When a combination mask/cover component defines a reaction well, it is aligned with the at least first surface area of the base substrate component, permitting reagents to be added to the nucleic acid deposited within the at least first surface area of the base substrate component. In some embodiments, access ports may be formed in the combination mask/cover component for delivery of reagents and withdrawal of sample aliquots for detection.

Any of the base substrate component, mask component, substrate frame or cover component may have an identifier that associates the biological sample of the individual with the at least one ridge and valley signature obtained from the individual.

Exemplary Embodiments of Devices.

Exemplary devices that allow direct amplification of fingerprint nucleic acid on the surface on which the nucleic acid is collected in an open PCR format are described. Such devices integrate the functions of fingerprint collection, nucleic acid sample collection from fingers and PCR amplification of fingerprint nucleic acid on the same device in an open PCR format without any form of nucleic acid sample transfer. The geometry, number of fingerprint nucleic acid deposition regions as well as the dimensions of the devices described here are for illustration purposes only and are not intended to limit the scope of the invention.

One device 201 having a polymeric film base substrate component is illustrated in FIG. 2. The polymeric film substrate may be made from a wide variety of polymeric films, and in this specific embodiment, the substrate is MICROAMP® clear adhesive film, wherein the adhesive is compatible with PCR conditions and reagents, and may be configured to fit within the scanning window of an optical fingerprint scanner. The base substrate component, for each fingerprint imaging/nucleic acid collection has an area of about 2.5 cm by about 5 cm. One or more fingerprints may be imaged while each finger is in contact with the substrate. Reaction chambers, which may be about 8 mm in diameter, may be formed over each fingerprint by placing a Secure-Seal™ 8-well mask (203) (Grace Bio-labs, AB8R-0.5) on top of the adhesive film as shown in FIG. 2. Each surface area containing nucleic acid (210-1.1, 210-1.2, 210-1.3, 210-1.4, 210-1.5, 210-1.6, 210-1.7, and 210-1.8) remain open and accessible for reagent addition. Each chamber formed by the mask surrounding each fingerprint may be filled with a volume of about 50 ul PCR reaction mix. The chambers may be sealed using a second section of MICRO-AMP® clear adhesive film over the top of the mask (not shown in FIG. 2). The assembled fingerprint PCR device may be placed on a flat thermal cycler block such as the GENEAMP® 9700 thermal cycler (Applied Biosystems), and may be secured to the thermal block for thermocycling.

Figure 4:
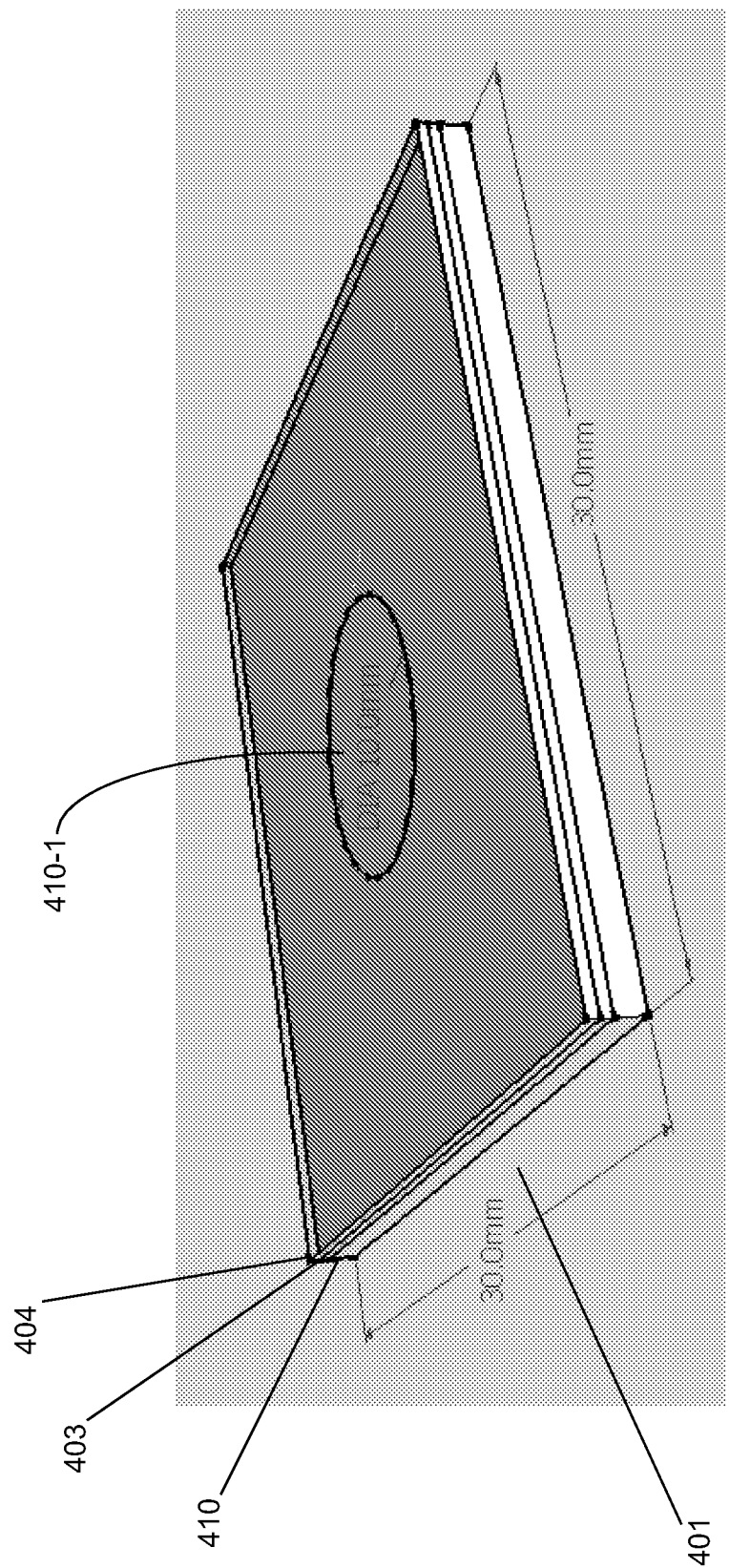
FIG. 4 illustrates another embodiment of a device for collection of a ridge and valley signature and biological sample of an individual that is compatible with nucleic acid amplification.

Another embodiment of a device 401 for collection of fingerprint image, fingerprint nucleic acid and in-situ nucleic acid amplification is shown in FIG. 4. In this embodiment, the device contains three component layers, and is shown in a closed configuration. The bottom layer is a transparent substrate 410 and is made of materials that can withhold thermal cycling of the PCR. The upper surface of the bottom layer may be hydrophobic except for a hydrophilic circle (which may be about 10 mm in diameter) which is indicated by the region 410-1. The middle layer, mask 403, has a 10 mm diameter through hole, which aligns with the hydrophilic circle 410-1 on the base substrate layer 401. The mask 403 has two functions. First, it allows fingerprint nucleic acid collection within the circular region 410-1 on the base substrate layer 410, while preventing the fingerprint DNA collection on the hydrophobic area of the upper surface of the base substrate layer 401. Second, the middle layer allows the collection of fingerprint nucleic acid from the portion of the finger that contacts the mask 403 surrounding the circular region 410-1 during fingerprint collection.

The top layer 404 serves as a protective cover layer to the middle and bottom layers, and is removable for fingerprint acquisition and for addition of reagents. The cover 404 may be put in place while handling the collected fingerprint nucleic acid, or during transit or mailing of the collected fingerprint nucleic acid to different locations for testing or archiving. The cover 404 may be present or it may be removed during the nucleic acid amplification reaction performed upon the nucleic acid collected from the contact of the finger with the substrate during the fingerprint imaging. When the cover 404 is absent during nucleic acid amplification, the nucleic acid amplification reaction mixture, resulting from addition of reagents to the nucleic acid present in the hydrophilic region 410-1, may be sealed with sealing solution layer which may be an oil.

To use the device 401, it is placed upon the scanning surface of the fingerprint imaging component, with the cover 404 removed and the hydrophilic circular region 410-1 is used to simultaneously collect the fingerprint image and nucleic acid from the finger placed in contact with the substrate for fingerprint imaging.

Many variants of this embodiment may be utilized in any combination. In another embodiment, the entire upper surface of the base substrate 410 may be hydrophobic. The upper surface of the base substrate 410 can be concave, forming a shallow depression, or any other desired shape to aid the retention of the PCR reaction mix and/or a sealing solution during PCR. The hydrophilic circle can be located at the bottom of the depression.

The mask layer 403 may be transparent. The mask layer 403 may also be translucent, so long as it does not interfere with fingerprint scanning. If the degree of transparency is different between the region within the circular region 410-1 and the remainder of the imaging area during fingerprint scanning, the fingerprint scanning software can make adjustments in order to obtain suitable quality fingerprint images. The fingerprint nucleic acid collected on the mask layer 403 may also be retained and archived for later analysis if needed. In some embodiments, the upper surface of the mask layer 403 may be covered with adhesive to enhance additional nucleic acid collection.

Figure 7:
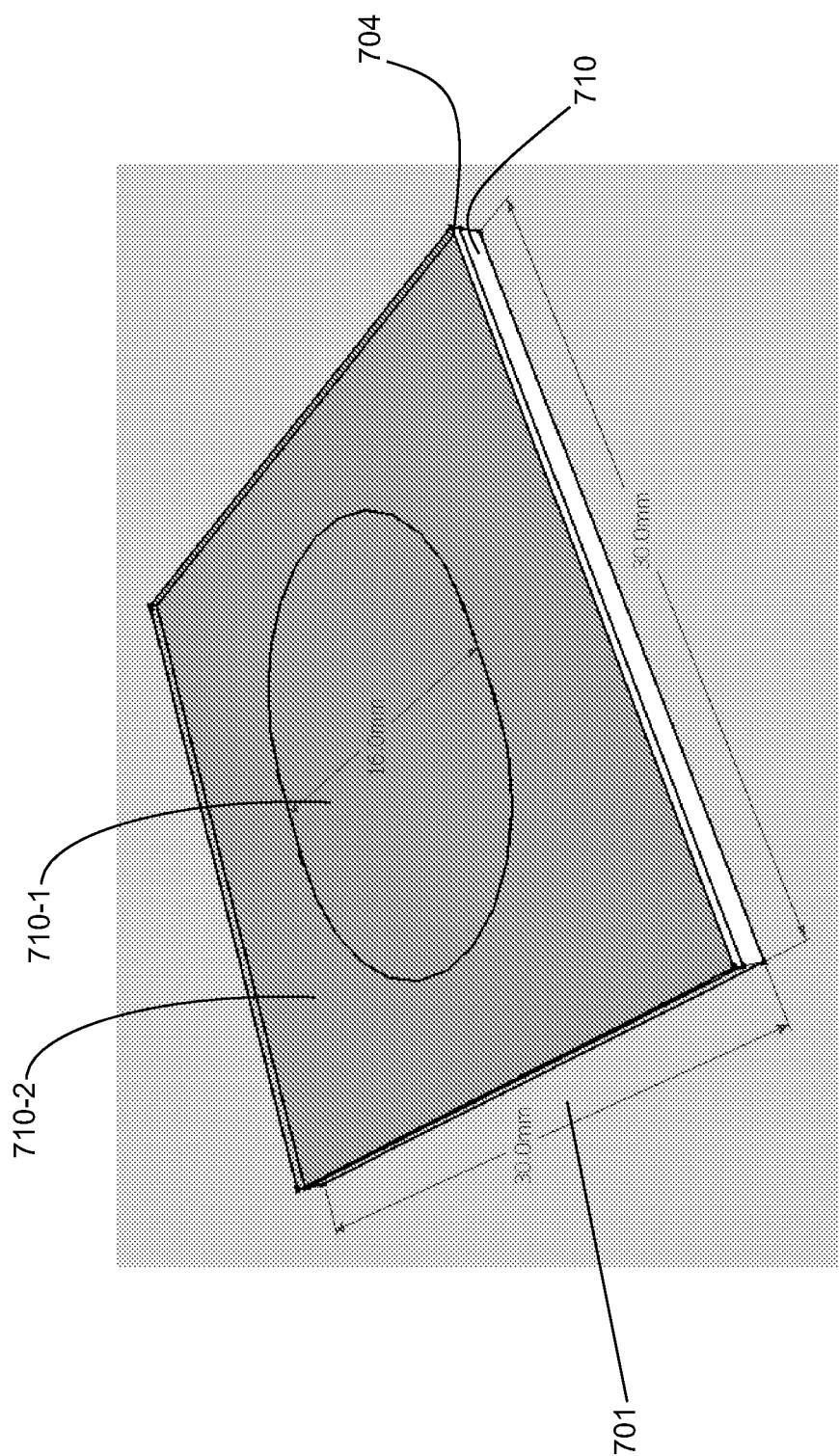
FIG. 7 illustrates another embodiment of a device for collection of a ridge and valley signature and biological sample of an individual that is compatible with nucleic acid amplification.

Yet another embodiment of the device is shown in FIG. 7. The device 701 may contain two component layers. The base substrate layer 710 may be transparent or translucent and is made of materials that can withstand thermal cycling of the PCR. Region 710-2 of the upper surface of the base substrate layer 710 is hydrophobic and surrounds a hydrophilic region 710-1 which is shaped like an oval in this particular embodiment. FIG. 7, as drawn, shows the two different regions of the upper surface of the base substrate as viewed thru a translucent upper cover layer 704. The dimensions of the hydrophilic region 710-1 may be approximately 16 mm by about 20 mm. The hydrophilic region 710-1 is used to collect fingerprint nucleic acid from the finger used for imaging a fingerprint of an individual.

The top layer 704 serves as a protective cover layer to the middle and bottom layers, and is removable for fingerprint acquisition and for amplification of the nucleic acid collected to the hydrophilic region 710-1. The cover 704 may be put in place while handling the collected fingerprint nucleic acid, or during transit or mailing of the collected fingerprint nucleic acid to different locations for testing or archiving. The cover 704 may be removed during the nucleic acid amplification reaction performed upon the nucleic acid collected from the contact of the finger with the substrate during the fingerprint imaging. The nucleic acid amplification reaction mixture at 710-1 may be sealed with a sealing solution layer which may be an oil.

To use the device 701, it is placed upon the scanning surface of the fingerprint imaging component, with the cover 704 removed and the hydrophilic region 710-1 is used to simultaneously collect the fingerprint image and nucleic acid from the finger placed in contact with the substrate for fingerprint imaging.

Many variants of this embodiment may be utilized in any combination. In another embodiment, the entire upper surface of the base substrate 710 may be hydrophobic. The upper surface of the base substrate 710 can be concave, forming a shallow depression, or any other desired shape to aid the retention of the PCR reaction mix and/or a sealing solution during PCR. The hydrophilic region 710-1 can be located at the bottom of the depression.

Figure 8:
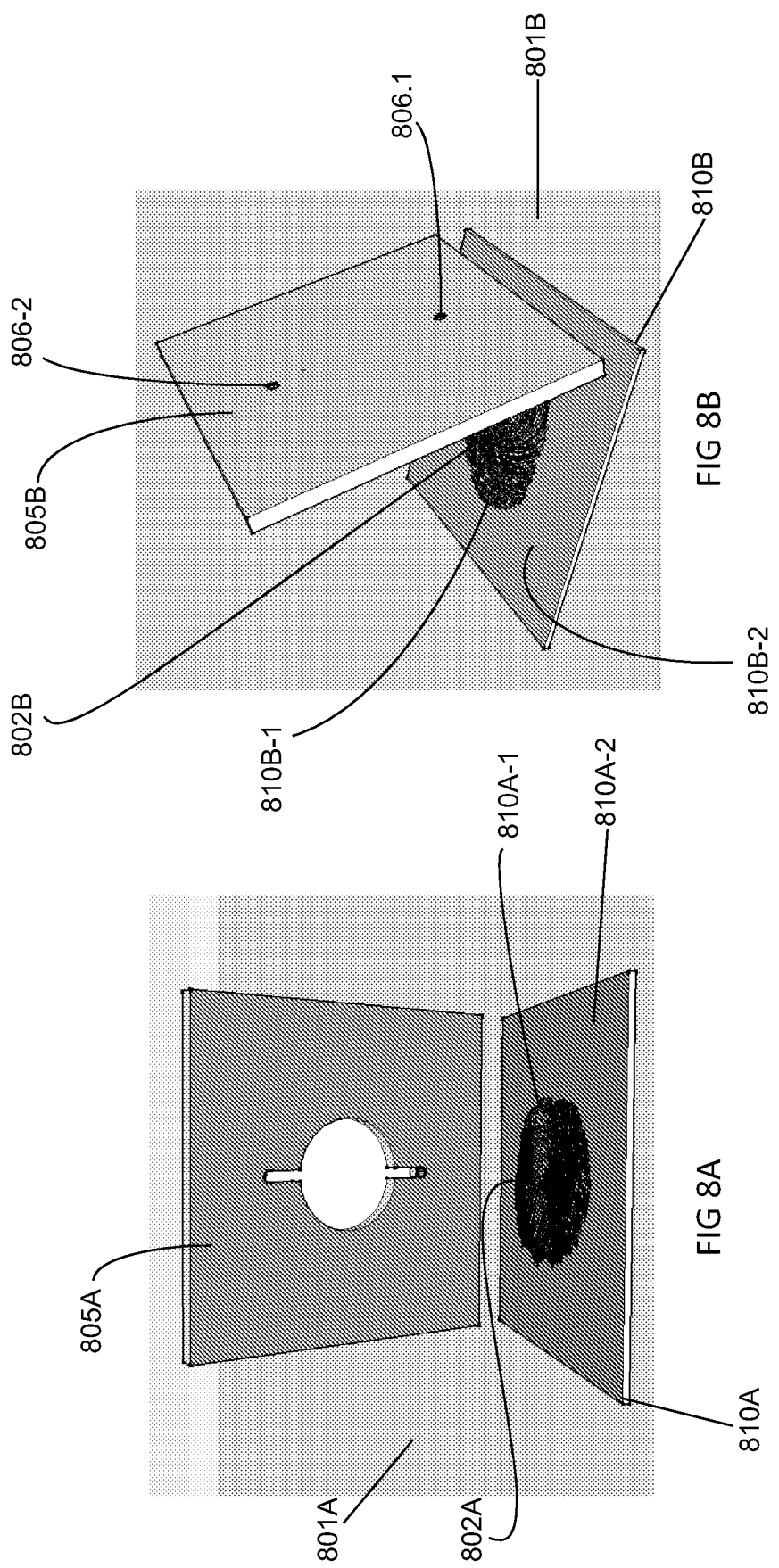
FIGS. 8A and 8B illustrate two embodiments of a device for collection of a ridge and valley signature and biological sample of an individual that is compatible with nucleic acid amplification.

Another embodiment of the device is shown in FIG. 8A. This embodiment, 801A, illustrates the feasibility of capturing DNA from a fingertip on a PCR compatible substrate and the subsequent formation of a PCR reaction chamber, using a combination mask and cover component 805A, directly over the fingerprint on the substrate, to perform direct nucleic acid amplification, and optionally a sequencing reaction. In one embodiment, nucleic acid from a finger contacting the base substrate layer 810A is collected on MICROAMP® clear adhesive film (Life Tech, 4306311) within region 810A-1. A reaction chamber, which may be about 8 mm in diameter and about 1 mm diameter deep, over the fingerprint deposit 802A was formed by placing a SECURESEAL well (Grace Bio-labs, AB8R-0.5) upon the region of the adhesive film 810A-2 surrounding the fingerprint nucleic acid deposit 802A in region 810A-1. The resulting chamber may be filled with 50 uL PCR reaction mix, and the top of the chamber may be sealed with another piece of blank MICROAMP® clear adhesive film. The assembled fingerprint PCR device may be thermal cycled on the AB 9700 flat thermal cycler block to amplify the nucleic acid and may include a sequencing reaction to provide amplicons suitable for detection, which may include fluorescent or other types of labels, for sequencing reactions requiring labels, or the amplification products may be detected by detection methods, such as semiconductor sequencing, that do not require labelling of the amplicons.

Many variations of this embodiment are possible. The base substrate layer 810A may not have any adhesive present, and the lower surface of the combination mask/cover component 805A forming the reaction well may instead have adhesive, which is compatible with PCR conditions and reagents, to attach to the base substrate layer 810A to form a leak tight reaction container surrounding the fingerprint nucleic acid deposit 802A in region 810A-1.

Another embodiment of the device is shown in FIG. 8B. Device 801B has a base substrate component 810B, where the fingerprint nucleic acid 802B is deposited within region 810B-1, surrounded by region 810B-2 where nucleic acid is not deposited. The combination cover and mask 805B forms a reaction well over the region 810B-1, and has two ports 806-1 and 806-2 extending through the cover/mask 805B, for addition of reagents and withdrawal of amplified nucleic acid for detection. Adhesive on either the lower surface of the combination cover/mask 805B outside of the well forming region, or on the base substrate layer in the region 810B-2 surrounding the fingerprint nucleic acid deposit 802B.

Figure 10:
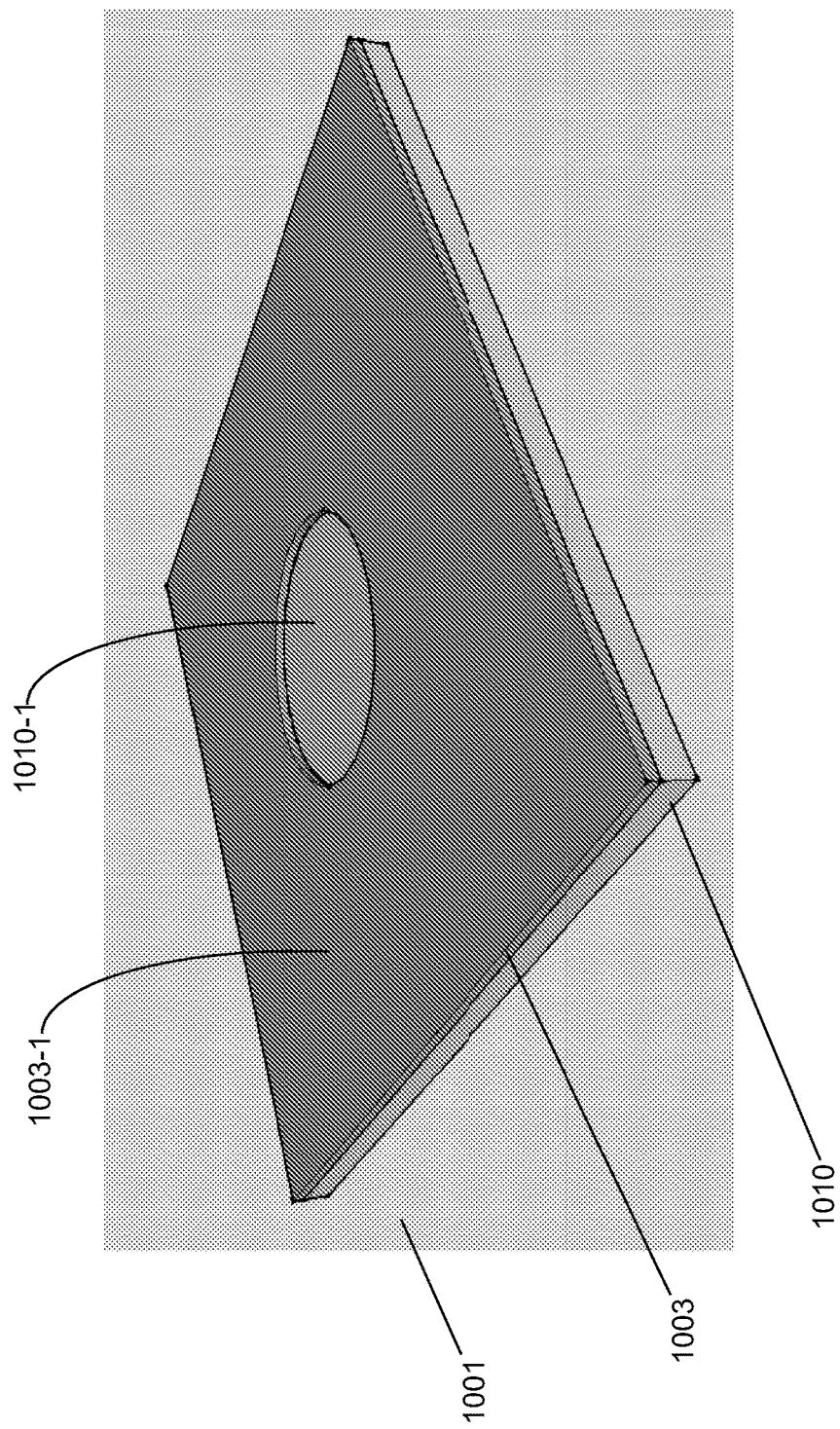
FIG. 10 illustrates another embodiment of a device for collection of a ridge and valley signature and biological sample of an individual that is compatible with nucleic acid amplification.

Another embodiment of a device configured to capture nucleic acids from a finger at the same time that imaging of the fingerprint is performed is shown in FIG. 10. The device 1001 is compatible with PCR reaction conditions and permits a nucleic acid amplification reaction, which may further include identification of the nucleic acid, including but not limited to STR analysis, in-situ, without requiring transfer of the nucleic acid acid to another reaction well or reaction surface. The PCR reaction may be an "open PCR" where the PCR is covered only by a sealing solution to prevent evaporation during PCR thermal cycling.

Device 1001 contains two component layers. The base substrate layer component 1010 is transparent and is made of materials that can withstand thermal cycling of the PCR. The upper surface of the base substrate layer component 1010 is hydrophobic except a hydrophilic region 1010-1 which may be about 10 mm in diameter, which is used to collect fingerprint DNA. The 10 mm diameter hydrophilic circular region shown for device 1001 is exemplary only and is not intended to exclude other shapes and sizes. The upper mask component layer 1003-1 has a through hole, having a diameter of about 10 mm, which aligns with the hydrophilic region 1010-1 on the base substrate layer component 1010. This region forms the reaction well for the in-situ PCR amplification of the nucleic acid deposited within region 1010-1. Open PCR may be performed on the nucleic acid deposited within the region 1010-1, and the reaction may be sealed with a sealing solution during thermocycling.

Many variants of this embodiments are possible. The region 1010-1 may be coated with PCR compatible adhesive to enhance fingerprint DNA collection. Alternately, the entire top surface of the base substrate layer component 1010 may be hydrophobic or hydrophilic. The base substrate layer component 1010 may have a concave depression or any other desired shape at region 1010-1 to aid in retaining the PCR reaction mix and/or sealing solution during PCR. The fingerprint collection area can be located at the bottom of the depression.

The mask component layer 1003-1 may allow the collection of fingerprint DNA from the part of the finger that is outside the 10 mm hole during the fingerprint collection process. The upper surface of the mask component layer 1003-1 can be coated with adhesive. The top layer may be transparent. The mask component layer 1003-1 could also be translucent, if so, the translucent mask component layer 1003-1 should not interfere with fingerprint scanning. If the degree of transparency is different between the regions within and outside of region 1010-1 during fingerprint scanning, fingerprint scanning software may be adjusted in order to obtain a high quality fingerprint image. The fingerprint DNA collected on the mask component layer 1003-1 can be archived and analyzed later if necessary. If desired, a cover layer may be added to serve as a protection layer.

Figure 13:
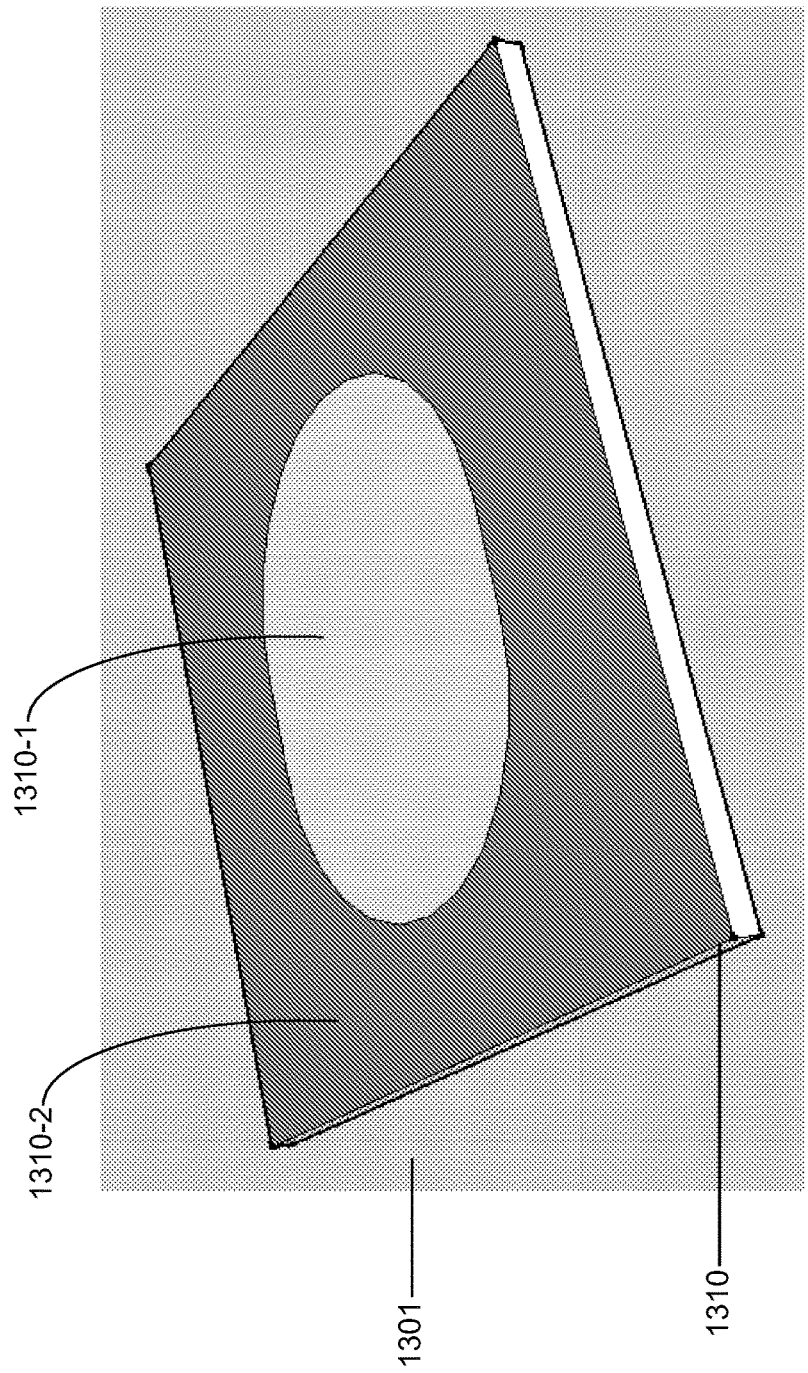
FIG. 13 illustrates another embodiment of a device for collection of a ridge and valley signature and biological sample of an individual that is compatible with nucleic acid amplification.

Another embodiment of the device is shown in FIG. 13. The device 1301 is made of materials that can withhold thermal cycling of the PCR. The upper surface of the base substrate area 1301 of the device is hydrophobic (region 1310-2) except for a hydrophilic region 1310-1, which may be configured as an oval with dimensions of about 16 mm by about 20 mm, which is used to collect fingerprint DNA. The dimensions described are just an example and is not intended to exclude other shapes and sizes. The device is placed over the scanning surface of the imaging component and an individual places a finger in contact with the hydrophilic region 1310-1 to simultaneously deposit a biological sample containing nucleic acid as well as image the fingerprint thru the base substrate layer component 1310 at region 1310-1. The collected nucleic acid may be amplified in-situ using an open PCR, where a sealing solution prevents evaporation of the PCR reagents and/or solvents.

In other variations, the 16×20 mm hydrophilic oval region 1310-1 may instead be coated with PCR compatible adhesive to enhance fingerprint DNA collection. Alternatively, the entire upper surface of the device 1301 is hydrophobic or hydrophilic. The device 1301 may have a concave depression or other desired shape to aid in retaining the PCR reaction mix and/or sealing solution during PCR. The fingerprint collection area can be located at the base of the depression.

Figure 14:
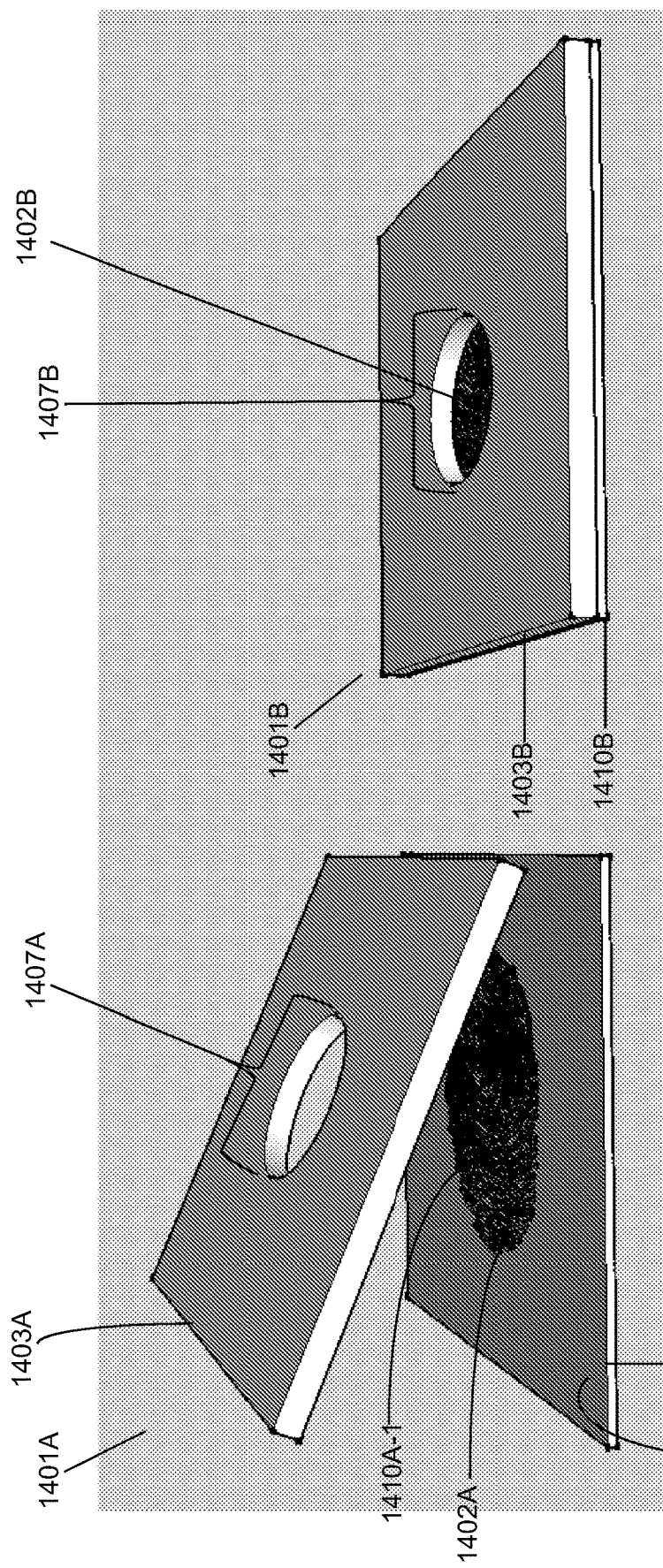
FIGS. 14A and 14B illustrates another embodiment of a device for collection of a ridge and valley signature and biological sample of an individual that is compatible with nucleic acid amplification, showing assembly of the device after collection of the ridge and valley signature and biological sample.
Figure 15:
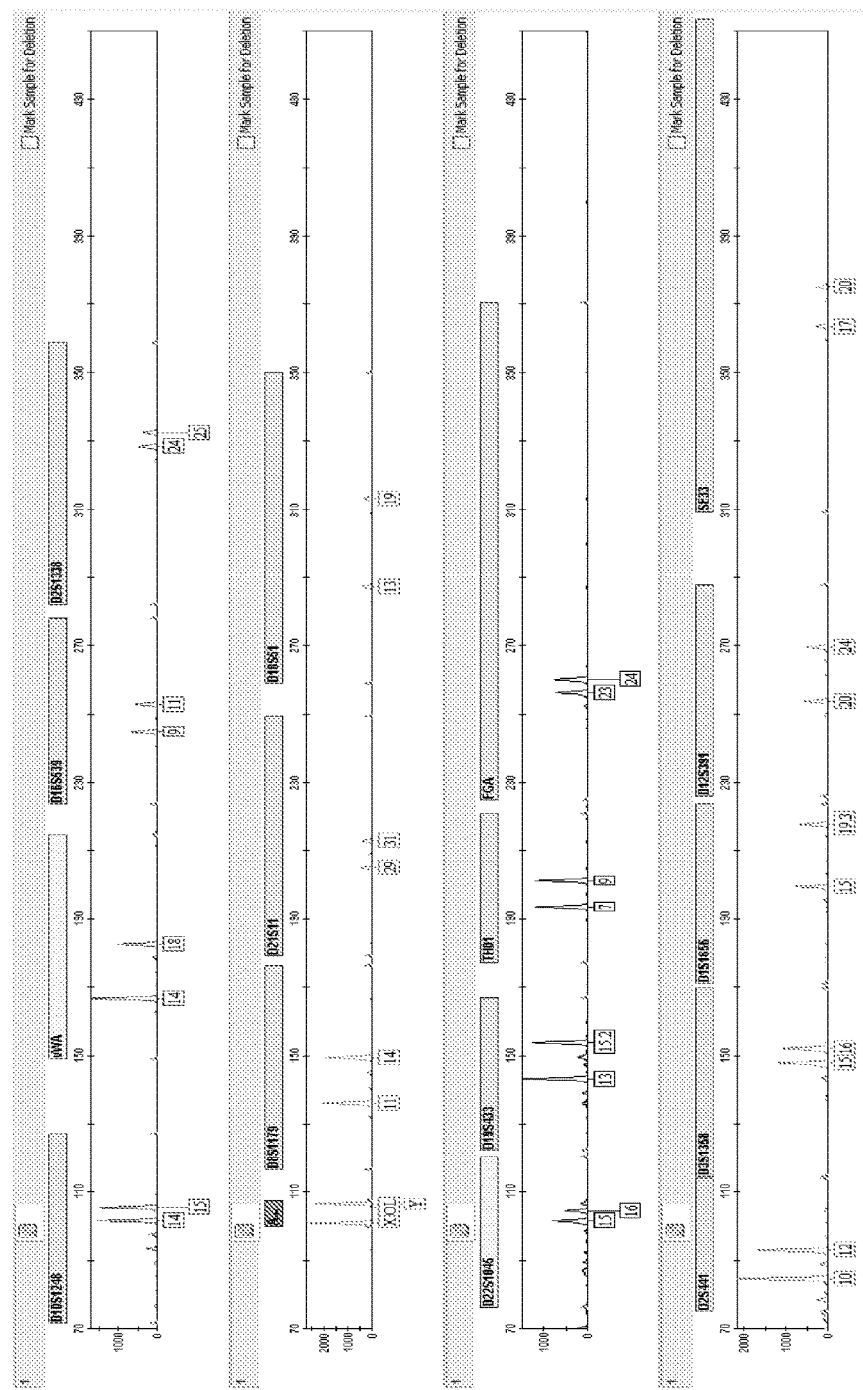
FIG. 15 is a graphical representation of a STR analysis of nucleic acid collected from an individual using one variation of the device of FIGS. 14A and 14B.

Yet another embodiment of the device is shown in FIG. 14. The device 1401A is shown in the process of assembly, and has a base substrate component 1410A made from a thin film which is compatible with both fingerprint collection and PCR reaction conditions. The upper surface area, including regions 1410A-1 and 1410A-2 film may be coated with PCR compatible adhesive. Collection of a fingerprint image and the fingerprint nucleic acid 1402A to region 1410A-1 is performed when the device is positioned upon the scanning surface of the imaging component. The mask layer component 1403A, having a through hole 1407A is the other portion of the device. An open PCR device 1401B, in its completed form, is shown in FIG. 14B, is formed by bonding the mask component layer 1403B, which may be a thin plastic or glass slide (for example 1 mm) with a 10 mm diameter through hole 1407B with the base substrate layer component 1410B containing fingerprint nucleic acid 1402B still aligned with the opening of the through-hole 1407B. The open PCR may then be performed with the fingerprint nucleic acid in-situ, and sealed with a sealing solvent layer, including but not limited to an oil layer. Detection of an aliquot of the amplified nucleic acid can be performed by extracting the aliquot from under the sealing solvent layer.

In one variation of the device illustrated in FIGS. 14A-B, the base substrate component 1410A is a piece of MICRO-AMP® clear adhesive film (Life Tech, 4306311). The open PCR device is 1401B formed by bonding a glass mask component layer 1403B with a 10 mm diameter through hole with the base substrate component layer 1410A adhesive film which contains the fingerprint nucleic acid deposited at region 1410A-1. In another variation, the upper surface of the glass mask component layer 1403B is hydrophobic to help retain the sealing solution during the open PCR reaction. In another variation, the base substrate component 1410A may be made of glass, and may be hydrophilic or hydrophobic. When the base component 1410A is glass or is a polymeric film with no adhesive, the lower surface of the mask component layer 1403B has PCR compatible adhesive on it, in order to bond the base substrate layer component to the mask component layer after deposition of the fingerprint nucleic acid, in order to form the reaction well for the in-situ nucleic acid amplification reaction.

Figure 17:
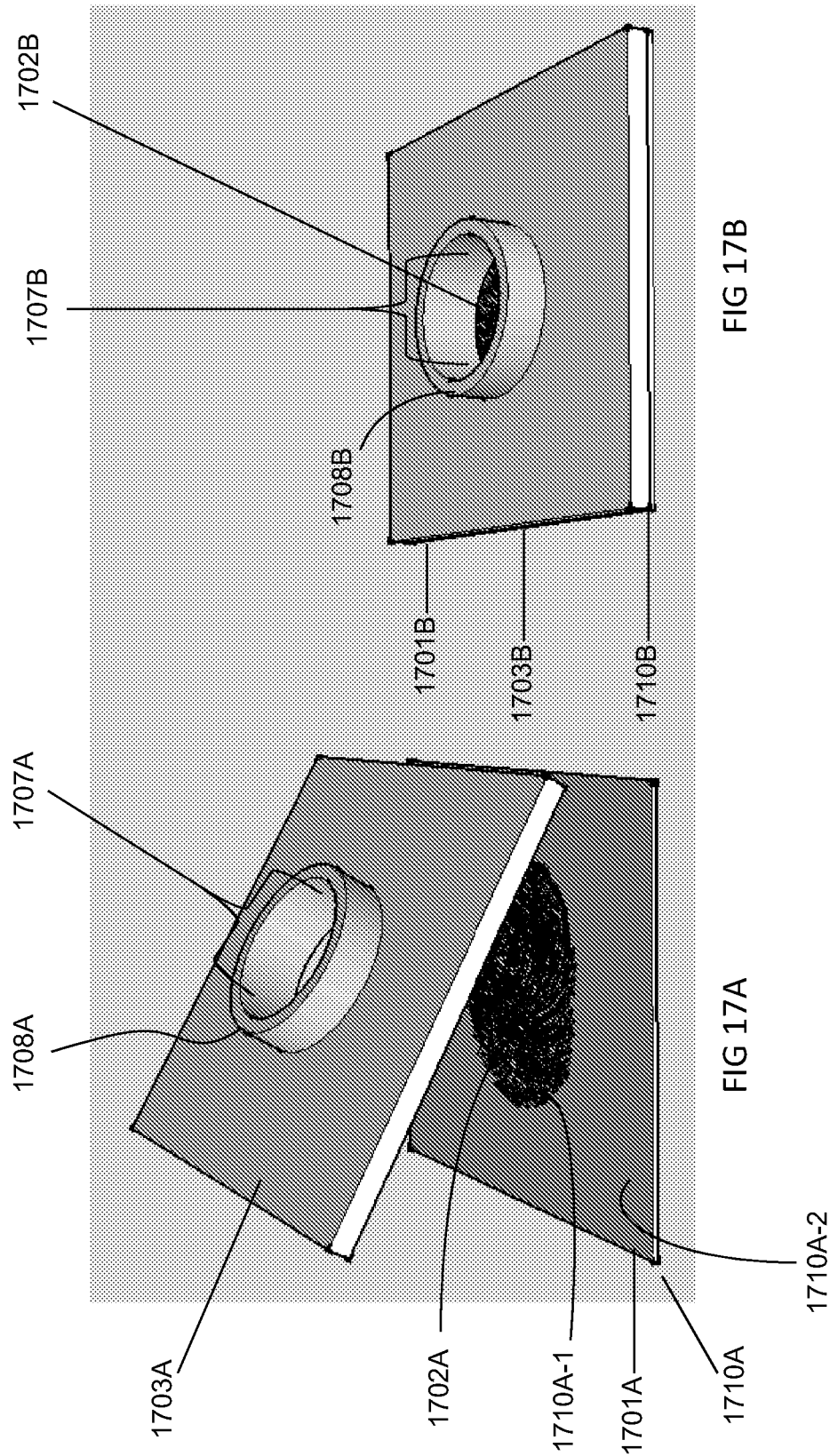
FIGS. 17A and 17B illustrates another embodiment of a device for collection of a ridge and valley signature and biological sample of an individual that is compatible with nucleic acid amplification, showing assembly of the device after collection of the ridge and valley signature and biological sample.

A further embodiment of the device is shown in FIGS. 17A and 17B. The device 1701A is shown in the process of assembly, and has a base substrate component 1710A made from a thin film which is compatible with both fingerprint collection and PCR reaction conditions. The upper surface area, including regions 1710A-1 and 1710A-2 film may be coated with PCR compatible adhesive. Collection of a fingerprint image and the fingerprint nucleic acid 1702A to region 1710A-1 is performed when the device is positioned upon the scanning surface of the imaging component. The mask layer component 1703A, having a through hole 1707A is the other portion of the device. In this embodiment, ring component 1708A is bonded to the mask component layer 1703A, surrounding the edge of the through hole 1707A. An open PCR device 1701B, in its completed form, is shown in FIG. 17B, is formed by bonding the mask component layer 1703B, which may be a thin plastic or glass slide (for example 1 mm) with a 10 mm diameter through hole 1707B with the base substrate layer component 1710B containing fingerprint nucleic acid 1702B still aligned with the opening of the through-hole 1707B. The ring 1708B assists in retaining the nucleic acid amplification reagents within the reaction well formed by the base substrate layer 1710B in combination with the mask component layer 1703B. The open PCR may then be performed with the fingerprint nucleic acid in-situ, and sealed with a sealing solvent layer, including but not limited to an oil layer. Detection of an aliquot of the amplified nucleic acid can be performed by extracting the aliquot from under the sealing solvent layer.

In one variation of the device illustrated in FIGS. 17A-B, the base substrate component 1710A is a piece of MICRO-AMP® clear adhesive film (Life Tech, 4306311). The open PCR device is 1701B formed by bonding a glass mask component layer 1703B with a 10 mm diameter through hole with the base substrate component layer 1710A adhesive film which contains the fingerprint nucleic acid deposited at region 1710A-1. In another variation, the upper surface of the glass mask component layer 1703B is hydrophobic to help retain the sealing solution during the open PCR reaction. In another variation, the base substrate component 1710A may be made of glass, and may be hydrophilic or hydrophobic. When the base component 1710A is glass or is a polymeric film with no adhesive, the lower surface of the mask component layer 1703B has PCR compatible adhesive on it, in order to bond the base substrate layer component to the mask component layer after deposition of the fingerprint nucleic acid, in order to form the reaction well for the in-situ nucleic acid amplification reaction.

Collection Assistance Liquid.

In aspects of the invention, a collection assistance liquid may be present when the biological sample is collected to the base substrate component of the device. A collection assistance liquid may be a solvent, a detergent, or a lysis solution.

Solvent.

Some suitable solvents that may assist with collection of nucleic acids from the substrate may include water, ethanol or acetonitrile. In some embodiments, the presence of one of these solvents may help to collect more of the nucleic acids present within a fingerprint on a base substrate component.

As used here, the term "detergent" is any substance that reduces the surface tension of water, and is used synonymously with the term "surfactant". In certain embodiments, the detergent can be a cationic detergent, anionic detergent, nonionic detergent, or a zwitterionic detergent. Examples of nonionic detergents include triton, such as the Triton™ X series (Triton™ X-100 t-Oct-$C_6H_4$—(OCH$_2$—CH$_2$)$_x$OH, x=9-10, TRITON™ X-100R, TRITON™ X-114 x=7-8), octyl glucoside, polyoxyethylene(9)dodecyl ether, digitonin, IGEPAL™ CA630 octylphenyl polyethylene glycol, n-octyl-beta-D-glucopyranoside (betaOG), n-dodecyl-beta, Tween™ 20 polyethylene glycol sorbitan monolaurate, Tween™ 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulf-onate. It is contemplated also that urea may be added with or without another detergent or surfactant.

In some embodiments, a surfactant that substantially lacks fluorescence between 300 nm and 750 nm is used in the methods of the invention. In some embodiments provided herein, the lysis solution includes a surfactant at a concentration that has low or no emission at the emission wavelengths of dyes or labels commonly used for detecting RNA, DNA, or proteins when in use for in-situ analysis of DNA, RNA, proteins or a surrogate thereof.

In some embodiments, an effective concentration of surfactant in a lysis mixture is a concentration of surfactant at which a sample is considered fully lysed as determined by propidium iodide staining using 1% TRITON X-100™ surfactant as a control. Lysis-effective concentrations of exemplary surfactants range from 0.02% or 0.05%, to 3% or more for TRITON X114™ surfactant, from 0.1% to 5% or more for NP40™ surfactant, and from 0.05% to 1% or to 3% for TRITON X100™ surfactant. When a combination of surfactants is used, the concentration of each surfactant may be lowered from the cited amounts.

The lysis solution may contain an enzyme to facilitate collection of nucleic acids onto the base substrate component. In certain embodiments, the lysis solution contains proteinase K. In various embodiments, proteinase K may be present in the lysis solution at about 0.8 mg/ml to about 1.5 mg/ml. In certain other embodiments the lysis solution can contain a protease enzyme. The enzyme may degrade structural proteins in order to permit extraction of biomolecules from biological cells on the substrate. The enzyme may be applied to the substrate while collection of the sample is performed, or the enzyme may be incorporated into the base substrate component, such as incorporation into a polymer film or coating on a glass. In certain embodiments herein, the lysis solution includes a polypeptide having protease activity such as for example, proteinase K.

In lieu of, or in addition to, proteinase K, the lysis solution can include a serine protease such as trypsin, chymotrypsin, elastase, subtilisin, streptogrisin, thermitase, aqualysin, plasmin, cucumisin, or carboxypeptidase A, D, C, or Y; a cysteine protease such as papain, calpain, or clostripain; an acid protease such as pepsin, chymosin, or cathepsin; or a metalloprotease such as pronase, thermolysin, collagenase, dispase, an aminopeptidase or carboxypeptidase A, B, E/H, M, T, or U. Qiagen Protease (p/n 19155, Qiagen, Valencia, Calif.) is an alternative to proteinase K and can be inactivated by EDTA.

In other embodiments, the enzyme contained in the lysis solution is a pancreatic proteolytic enzyme, such as porcine pancreatic enzyme. Keratinases, that may have utility in collection of nucleic acids, include but are not limited to keratinases isolated from bacteria or fungi. Some keratinases have enhanced stabilities in the presence of detergents, surfactant, metal ions and solvents, which is useful for the methods of the present teachings. Some non-limiting examples of a keratinase useful in the methods of the present teachings include the keratinases from *P. pastoris, B. megaterium*, and *B. licheniformis*.

Automatic Operation.

In some embodiments, the system provides that at least one of the components of the device may be supported operably within a housing of an apparatus which is configured to automatically subject the nucleic acid deposited upon the base substrate component to a nucleic acid amplification reaction, which may further include a nucleic acid sequencing reaction. The housing may have a platform to secure at least the base substrate component containing the collected biological sample. Once the substrate is secured, the apparatus may initiate nucleic acid amplification and/or sequencing reactions. The apparatus may further add an identifier to the at least one component of the device. The identifier may be the identifier issued to the substrate when the ridge and valley signature and the biological sample was collected or it may contain additional information about the shipping, archiving or processing of the substrate after collection. The apparatus may include a processor which is configured to control the apparatus to perform the reaction and/or detection of the nucleic acid sequence identity. The processor may be configured to add the identifier issued to the at least base substrate component and it may further be configured to add any additional information about the shipping, archiving or processing of the base substrate component after the reaction or detection process. The apparatus may also be provided with computer readable media to instruct the apparatus to perform the operations of concentration and identification. The computer readable medium may be non-transitory.

Integrated System for Amplification and Identification.

While microfluidic technology is commercially available for integrated nucleic acid amplification and identification, the relatively high cost (approximately $350/sample) may disfavor this approach in the light of emerging improvements in direct amplification workflows for processing buccal swab samples. Microfluidic instrumentation for "rapid DNA" systems which integrate the functions of cell lysis, DNA purification, PCR and capillary electrophoresis identification, relies upon on-chip microvalves and micropumps. The resultant complexity of design of such microfluidic or mesofluidic cartridges increases the cost per sample.

Using newly commercially available STR analysis kits such as IDENTIFILER DIRECT or NGM SELECT (Life Technologies, Inc.), it has been discovered that no extensive cell lysis nor nucleic acid purification is necessary in order to generate high quality STR profiles directly from buccal swab samples. Buccal swab samples only need to be placed into about 300 ul PREP-N-GO® Buffer (Life Technologies, Inc.) for about 10 min, and about 3 ul of the lysate can be directly transferred to a reaction site. Paper punches from a paper substrate may also be lysed in small volumes of lysis buffers and amplified directly as well. The reaction site may be a hydrophilic location on a plate (See FIG. 18) or a reaction well on a simple reaction cartridge (See FIG. 21). A small quantity (about 25 ul of a STR PCR master mix) is added to the sample for nucleic acid amplification. Instead of a closed chamber or tube, the PCR may be performed as an open PCR, where a sealing solution such as mineral oil is used to prevent evaporation. Using open PCR, simple liquid dispensing technology, including but not limited to AUTOMATE Express instrumentation, is capable of fully automating STR analysis workflow at a lower cost, simplified handling and workflow requirements.

Figure 18:
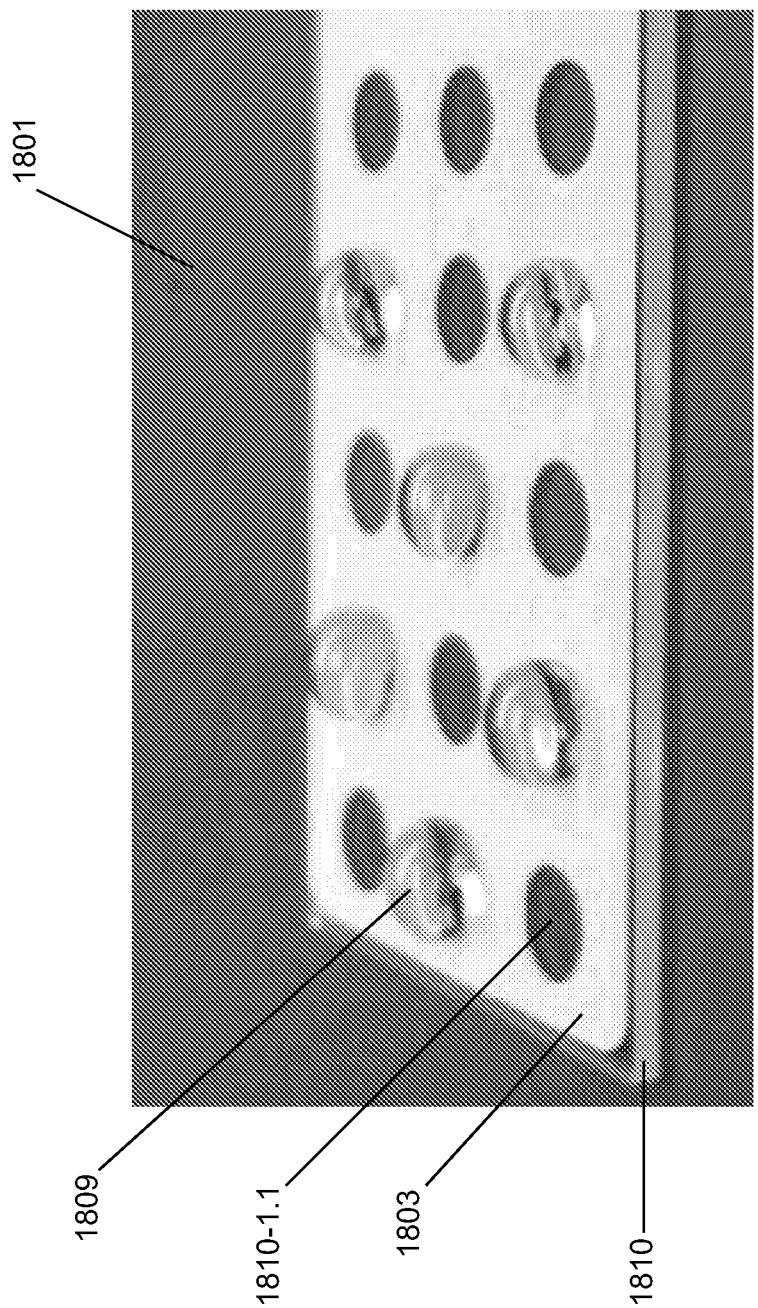
FIG. 18 illustrates a base substrate component of the integrated amplification and detection system, having selected hydrophilic reaction sites populated with open PCR samples.

Using reaction plates such as that illustrated in FIG. 18, for collection of fingerprint nucleic acid and subsequent analysis is amenable to automation. The open PCR slide contains hydrophilic wells defined by hydrophobic modification of the slide surface, for example, TEFLON® printing. The open PCR format allows facile recovery of the PCR product through the sealing solution by a simple pipetting operation. The small thermal cycler footprint and weight make it an ideal PCR module in a fully integrated STR typing system. The AMPLISPEED slide thermal cycler used in Example 6 weighs only 2.9 kg with dimension of only about 126 mm by about 295 mm by about 112 mm.

Rinsing a fingerprint nucleic acid deposit before transferring the rinse to the open PCR slide allows the option of using a rinse solution that is capable of selectively dissolving nucleic acid and leaving PCR inhibitors from the fingerprint nucleic acid deposit behind on the substrate. The base substrate component surface, 1810-1.1 (or occupied 1809) of FIG. 18, can also be treated to have the same function of retaining inhibitor and release DNA into rinse solution.

A hybrid device containing both fingerprint DNA collection and open PCR functionality enhances the integrity of chain of custody, because the fingerprint DNA never leaves the device before the nucleic acid amplification reaction is finished.

Figure 21:
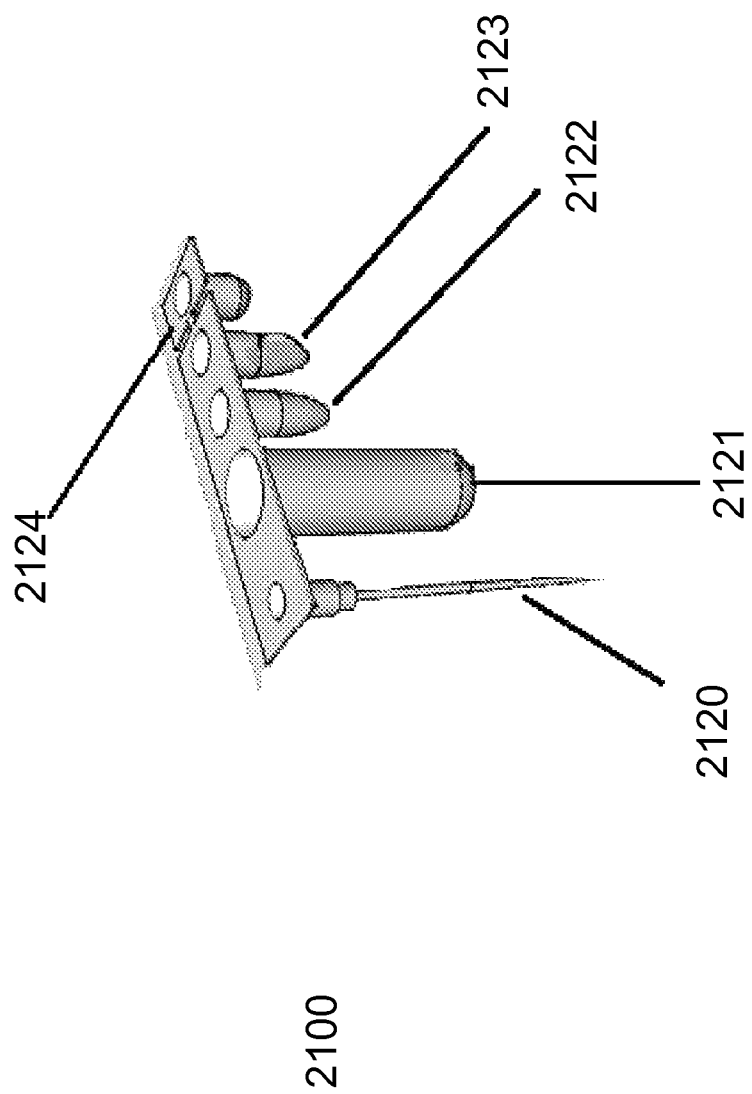
FIG. 21 is a graphical representation of a reaction component of the integrated amplification and identification system.

Because of the simplicity of the liquid transfer requirements (FIG. 21 shows an exemplary cartridge schematic; the workflow is described below), the liquid handling arm only needs to transfer up to 25 uL volume and only needs to travel 10 cm distance in XYZ directions. If this system is designed to process 8 samples simultaneously, the thermal cycler and CE modules will be much smaller than current stand-alone PCR and CE instruments. The fact that all three of the liquid hander, PCR and CE components may be controlled by a single computer will also help to reduce size and weight. The total run time could be shorter than commercially available microfluidic systems, such as RAPIDHIT™, (Integenex), which requires ninety minutes. Since a cartridge is very simple and can be designed for running single samples, the cost could be lower than that of RAPIDHIT™ as that cartridge is configured to run four samples, potentially causing wastage.

Exemplary Workflow.

- A cartridge is placed into the instrument. A reservoir well containing sealing solution resides within the PCR thermal cycler. A reservoir well containing HIDI® formamide and GS500 LIZ® size standard (Life Technologies) resides in a holder located on a translational stage, which allows the transfer of HIDI® formamide and LIZ® size standard (Life Technologies) for CE injection after amplification.
- A buccal swab containing nucleic acid is placed into a well containing about 300 ul PREP-N-GO® (Life Technologies) lysis buffer.
- The instrument is closed and the experiment run is started.
- The instrument activates the cutter to cut the connection between HIDI® well and the rest of the cartridge.
- After 10 min incubation, the liquid dispensing arm picks up a pipette tip and transfers 3 uL lysate to a PCR mixture well, containing a direct amplification STR master mix and agitates the mixture a few times.
- The instrument transfers and places PCR mix containing the nucleic acid into the bottom of the well containing a sealing solution such as mineral oil. The sealing solution will prevent PCR reaction evaporation.
- PCR thermocycling may be run as directed by manufacturer's suggestions or the cycles may be modified as needed. A typical run may be 95° C./11 m, then 30 cycles of 94° C./20 s, 59° C./2 m, 72° C./1 m followed by 60° C./25 min and 4° C.-hold.
- After PCR, 1 uL of PCR product is transferred into well containing HIDI® formamide and LIZ® size standard.
- The well containing HIDI® formamide, LIZ® size standard and amplified nucleic acid is transported by translational stage to CE module for CE analysis.

A system for identifying a target nucleic acid, is provided including: a base substrate component including one or more hydrophilic sites separated by hydrophobic zones where at least one hydrophilic site is configured to contain at least one target nucleic acid and further where the base substrate component is made of one or more materials compatible with reaction conditions of a nucleic acid amplification reaction; a reaction component configured to amplify the at least one target nucleic acid at the at least one hydrophilic site to form at least one nucleic acid amplification product; and a detection component configured to identify at least one nucleic acid sequence of the at least one nucleic acid amplification product. In some embodiments, the base substrate component may be polymeric film or glass. In various embodiments, the reaction component may not require a solid upper sealing component for the substrate. The reaction component may be configured to provide an oil sealing layer for the at least one hydrophilic site for performing the nucleic acid amplification reaction. The reaction component may be configured to provide an oil sealing layer for each of the one or more hydrophilic sites. The reaction component may be configured to provide nucleic acid amplification reagents to the at least one target nucleic acid contained on the at least one hydrophilic site on the base substrate component. The reaction component may be configured to provide suitable reaction conditions to perform a nucleic acid amplification of the at least one target nucleic acid contained on the at least one hydrophilic site on the base substrate component. The system may be further configured to withdraw a volume of the at least one nucleic acid amplification reaction product from under the oil seal for identification of the at least one nucleic acid sequence by the detection component.

The detection component of the system may be selected from a fluorescent dye sequencing component, a semiconductor sequencing component, or a pyrophosphate sequencing component. In some embodiments, the detection component may be a fluorescent dye sequencing component. In some embodiments, the fluorescent dye sequencing component may be a mobility dependent fluorescent dye sequencing component. In some embodiments, the mobility dependent fluorescent dye sequencing component may be capillary electrophoresis.

The invention may provide a base substrate component for nucleic acid amplification and identification, including: one or more hydrophilic sites separated by hydrophobic zones wherein at least one hydrophilic site is configured to contain at least one target nucleic acid; where the base substrate component is made of one or more materials compatible with reaction conditions of a nucleic acid amplification reaction; and further where the base substrate component is configured to permit extraction of an aliquot of an amplified target nucleic acid for detection of the nucleic acid sequence identity. The base substrate component may be polymer or glass.

A kit is provided, including a base substrate component as described above, and optionally, instructions for its use. The kit may further include reagents for a nucleic acid amplification reaction. The kit may further include reagents for a nucleic acid sequencing reaction.

A method is provided for identifying at least one target nucleic acid, encompassing the steps of: providing a base substrate component having one or more hydrophilic sites separated by hydrophobic zones wherein at least one hydrophilic site includes at least one target nucleic acid and further wherein the base substrate component is made of one or more materials compatible with reaction conditions of a nucleic acid amplification reaction; providing reagents suitable for amplification of the at least one target nucleic acid at the at least one hydrophilic site; performing a nucleic acid amplification reaction upon the at least one target nucleic acid to form at least one nucleic acid amplification product; and detecting the nucleic acid sequence of the at least one nucleic acid amplification product, thereby identifying the at least one target nucleic acid.

In some embodiments, no solid upper sealing component for the substrate may be provided. In various embodiments, the method further includes the step of providing a sealing solution layer for the at least one hydrophilic site containing the at least one nucleic acid for the nucleic acid amplification reaction. In some embodiments, the sealing solution layer may be provided for each of the one or more hydrophilic sites. In some embodiments, the method further includes the step of providing nucleic acid amplification reagents to the at least one target nucleic acid contained on the at least one hydrophilic site on the substrate. The method may further include providing suitable reaction conditions to perform a nucleic acid amplification of the at least one target nucleic acid contained on the at least one hydrophilic site on the base substrate component. In some embodiments, a volume of the at least one nucleic acid amplification reaction product is withdrawn from under the oil seal to identify the at least one nucleic acid sequence by the detection component.

In some embodiments of the method, the detection component may be selected from a fluorescent detection component, a semiconductor detection component, or a pyrophosphate detection component. In other embodiments, the detection may be a fluorescent dye sequencing component. In yet other embodiments, the fluorescent dye sequencing component may be a mobility dependent fluorescent dye sequencing component. In other embodiments, the mobility dependent fluorescent dye sequencing component may be capillary electrophoresis.

The invention also provides a system for identifying a target nucleic acid, including (a) a reaction cartridge including: a lysis well configured to hold a sample substrate having a biological sample which includes the target nucleic acid and an aliquot of a lysis buffer, where the biological sample is lysed to release target nucleic acid; a PCR well configured to hold an aliquot of PCR reagents, where the released target nucleic acid is amplified to form an amplified target nucleic acid sample; a sealing solution well configured to hold an aliquot of sealing solution, where the sealing solution is transferred to the PCR well to seal the open PCR; and optionally, a transfer tip configured to transfer any of the aliquots of released target nucleic acid, sealing solution and amplified target nucleic acid sample; and optionally, a detection sample preparation well operably connected to the reaction cartridge, wherein the detection sample preparation well is configured to hold an aliquot of reagents configured to prepare the sample for identification of a nucleic acid sequence of the amplified target nucleic acid sample; and where the reaction cartridge comprises one or more materials compatible with reaction conditions of a nucleic acid amplification reaction; (b) a reaction component configured to amplify the released target nucleic acid to form the amplified target nucleic acid sample; and (c) a detection component configured to identify a nucleic acid sequence of the amplified target nucleic acid sample. In some embodiments, the reaction cartridge may be made of polymer or glass. In some embodiments, the sample substrate may be a section of a paper substrate, including but not limited to a paper punch from a paper substrate to which a biological sample has been collected, or a buccal swab. In various embodiments, the reaction cartridge may not require a solid upper closure component for the reaction cartridge. In some embodiments, the system may be configured to transfer an aliquot of the released target nucleic acid from the lysis well to the PCR well. In some embodiments, the reaction component may be configured to provide suitable reaction conditions to perform a nucleic acid amplification of the released target nucleic acid contained in the PCR well of the reaction cartridge. In various embodiments, the system may be configured to withdraw a volume of the amplified target nucleic acid sample from under the oil seal and transfer it to the detection sample preparation well to prepare the amplified target nucleic acid sample for identification of the nucleic acid sequence by the detection component. In yet other embodiments, the detection component may be selected from a fluorescent dye sequencing component, a semiconductor sequencing component, or a pyrophosphate sequencing component. In some embodiments, the detection component may be a fluorescent dye sequencing component. In some embodiments, the fluorescent dye sequencing component may be a mobility dependent fluorescent dye sequencing component. In some embodiments, the mobility dependent fluorescent dye sequencing component may be a capillary electrophoresis component. The system may further include a plurality of reaction cartridges.

The invention also provides a reaction cartridge for nucleic acid amplification and identification, including (a) a lysis well configured to hold a sample substrate having a biological sample including the target nucleic acid and an aliquot of a lysis buffer, where the biological sample is lysed to release target nucleic acid; (b) a PCR well configured to hold an aliquot of PCR reagents, where the released target nucleic acid is amplified to form an amplified target nucleic acid sample; (c) a sealing solution well configured to hold an aliquot of sealing solution, where the sealing solution is transferred to the PCR well to seal the open PCR; and optionally, (d) a transfer tip configured to transfer any of the aliquots of released target nucleic acid, sealing solution and amplified target nucleic acid sample; and optionally, (e) a detection sample preparation well operably connected to the reaction cartridge, where the detection sample preparation well is configured to hold an aliquot of reagents configured to prepare the sample for identification of a nucleic acid sequence of the amplified target nucleic acid sample; and further where the reaction cartridge is made of one or more materials compatible with reaction conditions of a nucleic acid amplification reaction. In some embodiments, the reaction cartridge is made of one or more polymers, glass or a combination thereof.

The invention also provides a kit including a reaction cartridge a reaction cartridge for nucleic acid amplification and identification, including (a) a lysis well configured to hold a sample substrate having a biological sample including the target nucleic acid and an aliquot of a lysis buffer, where the biological sample is lysed to release target nucleic acid; (b) a PCR well configured to hold an aliquot of PCR reagents, where the released target nucleic acid is amplified to form an amplified target nucleic acid sample; (c) a sealing solution well configured to hold an aliquot of sealing solution, where the sealing solution is transferred to the PCR well to seal the open PCR; and optionally, (d) a transfer tip configured to transfer any of the aliquots of released target nucleic acid, sealing solution and amplified target nucleic acid sample; and optionally, (e) a detection sample preparation well operably connected to the reaction cartridge, where the detection sample preparation well is configured to hold an aliquot of reagents configured to prepare the sample for identification of a nucleic acid sequence of the amplified target nucleic acid sample; and further where the reaction cartridge is made of one or more materials compatible with reaction conditions of a nucleic acid amplification reaction, and optionally, instructions for its use. In some embodiments, the reaction cartridge of the lot is made of one or more polymers, glass or a combination thereof. In various embodiments, the kit may further include reagents for a nucleic acid amplification reaction. In various embodiments the kit may further include a sealing solution. In some other embodiments, the kit may further include reagents for a nucleic acid sequencing reaction.

The invention also provides a method of identifying a target nucleic acid, including the steps of: (a) providing a reaction cartridge including: a lysis well configured to hold a sample substrate comprising a biological sample comprising the target nucleic acid and an aliquot of a lysis buffer, where the biological sample is lysed to release target nucleic acid; a PCR well configured to hold an aliquot of PCR reagents, where the released target nucleic acid is amplified to form an amplified target nucleic acid sample; a sealing solution well configured to hold an aliquot of sealing solution, where the sealing solution is transferred to the PCR well to seal the open PCR; and optionally, a transfer tip configured to transfer any of the aliquots of released target nucleic acid, sealing solution and amplified target nucleic acid sample; and optionally, a detection sample preparation well operably connected to the reaction cartridge, where the detection sample preparation well is configured to hold an aliquot of reagents configured to prepare the sample for identification of a nucleic acid sequence of the amplified target nucleic acid sample; and where the reaction cartridge includes one or more materials compatible with reaction conditions of a nucleic acid amplification reaction; (b) providing reagents suitable for amplification of the released target nucleic acid in the PCR well of the reaction cartridge; (c) sealing the PCR well with an aliquot of the sealing solution; (d) performing a nucleic acid amplification reaction upon the released target nucleic acid to form the amplified target nucleic acid sample; and (e) detecting the nucleic acid sequence of the amplified target nucleic acid sample, thereby identifying the at least one target nucleic acid. In some embodiments, the reaction cartridge may be polymeric film or glass. In some embodiments the sample substrate may be a section of a paper substrate or a buccal swab. In various embodiments, the method may further include the step of adding the sample substrate including the biological sample containing the target nucleic acid to the lysis well, and lysing the biological sample to release the target nucleic acid. In other embodiments, the method may further include the step of transferring an aliquot of the released target nucleic acid from the lysis well to the PCR well with the transfer tip after the biological sample has been lysed to release target nucleic acid. In various embodiments, no solid upper sealing component for the substrate may be provided. In some embodiments, the method may further include the step of transferring the sealing solution with the transfer tip to the PCR well of the reaction cartridge containing the released nucleic acid and the aliquot of PCR reagents. In some embodiments, the method may further include the step of providing suitable reaction conditions to amplify the released target nucleic acid contained in the PCR well of the reaction cartridge to form the amplified target nucleic acid sample. In some embodiments, a volume of the amplified target nucleic acid sample may be withdrawn from under the oil seal with the transfer tip and transferred to the detection sample preparation well. In other embodiments, the detection component may be selected from a fluorescent dye sequencing component, a semiconductor sequencing component, or a pyrophosphate sequencing component. In yet other embodiments, the detection component may be a fluorescent dye sequencing component. In some embodiments, the fluorescent dye sequencing component may be a mobility dependent fluorescent dye sequencing component. In some embodiments, the mobility dependent fluorescent dye sequencing component may be a capillary electrophoresis component. In some embodiments, the aliquot of reagents configured to prepare the sample for identification of a nucleic acid sequence of the amplified target nucleic acid sample may include a denaturant. The denaturant may be formamide. In some embodiments, the aliquot of reagents further include a size standard.

Additional Imaging Components.

In another embodiment of the present teachings, the system can further include at least a second imaging component for collecting a second image of the individual. The second image of the individual can be either the face of the individual or a component of the individual amenable to biometric identification. Suitable biometric images that may be collected as the second image include a retinal scan, or iris scan, the contours of the ear, facial recognition, hand geometry, foot geometry, voice, odor and scent.

Processor.

After collection of the at least one ridge and valley signature, the signature, in analog or digital format, can be transmitted to a database having a plurality of ridge and valley signatures, as well as any other physical biometric data collected and deemed suitable to transmission. In some embodiments, the system includes a processor configured to transmit the ridge and valley signature obtained from the individual to at least one database which retains ridge and valley signatures of individuals. In some embodiments the database is selected from the group consisting of a forensic, criminal, identity, child identity, missing persons, immigration, department of motor vehicles, terrorist, paternity, arrestee, convict database, access control or any combination thereof.

After amplification of the nucleic acid collected from the individual, and detection of the nucleic acid sequence identity of the amplicons resulting from the amplification, one or more processors of the system may be configured to transmit the nucleic acid sequence identity of the individual to at least one database containing nucleic acid sequence identities selected from the group consisting of a forensic, criminal, identity, child identity, missing persons, immigration, department of motor vehicles, terrorist, paternity, arrestee, convict database, access control and any combination thereof.

Identifier.

In still other embodiments of the present teachings, the system can further include an identifier for associating identifying information with the ridge and valley signature, biological sample containing nucleic acid, and, optionally a physical image, including any of a facial image, an iris image, a retinal image or an ear image of the individual. In some embodiments, the name of the individual is included in the identifier. The identifier may aid in correlating various collected samples and may preclude sample mix-up and human error as may occur with nonsystematic sample labeling for identifying collected data and samples. In various embodiments, the identifier is alphanumeric, graphical, magnetic, or electromagnetic. In some embodiments, the identifier is a barcode. In various embodiments, the base substrate component includes an identifier. In other embodiments, a frame entails an identifier. In some embodiments, an enclosure for the device includes an identifier. In yet other embodiments, both the substrate component and an enclosure include the identifier to aid in correlating the collected sample and images. If more than one imaging component is included in the system, the same identifier may be used on all the collected data and samples of one individual.

Reaction Components.

In yet other embodiments, the system additionally includes amplification components which may be used to optionally release the at least one nucleic acid from the biological sample; amplify the at least one nucleic acid;

and/or separate the amplified at least one nucleic acid. The reaction component is configured to subject the device containing the biological sample on the substrate to a nucleic acid amplification reaction, which may include thermocycling conditions. These include any appropriate thermal cycling instrument that may be used or adapted to contain the devices described here. The reaction component may be configured to subject a single biological sample containing nucleic acid, i.e. a device having only single region for a single fingerprint nucleic acid deposit. Alternatively, the reaction component may be configured to subject a plurality of biological samples containing nucleic acid, either a single sample from a plurality of individuals as in FIG. 2, or a plurality of devices having a single fingerprint nucleic acid deposition site, to nucleic acid amplification reactions. When the reaction component is configured to subject a plurality of devices configured to contain a single fingerprint nucleic acid deposition site, then the reaction component may include a framework to secure the plurality of devices within the reaction component instrument for safe handling. The nucleic acid amplification reaction may be a polymerase chain reaction, and may be performed as an open PCR. The reaction component may be further configured to perform a DNA sequencing reaction while the nucleic acid and/or the nucleic acid amplification products are still present on the substrate component of the device. The nucleic acid sequencing reaction may be a fluorescent dye sequencing reaction, a semiconductor sequencing reaction, or a pyrophosphate sequencing reaction. When the reaction is a fluorescent sequencing reaction, the fluorescent sequencing reaction may be sequencing by synthesis or Sanger sequencing. The biological sample containing at least one nucleic acid may be subjected to analysis for nucleic acid markers such as DNA markers for STRs, Indels, SNPs and combinations thereof as well as DNA sequencing methods. Reagents for analyzing nucleic acids are commercially available such as the AMPF/STR® Identifiler® Direct PCR Amplification Kit or NGM® SELECT EXPRESS (Applied Biosystems, Foster City, Calif.) and the POWERPLEX® 18D System (Promega Corp. Madison, Wis.) following the manufacturer's instructions.

The reaction component may be configured to perform the nucleic acid amplification reaction and/or sequencing reactions in an open PCR format, i.e. where the reaction well formed in the device is sealed with a sealing solution layer to prevent evaporation during the reactions. In some other embodiments, the reaction component is configured to perform the nucleic acid amplification reaction and/or sequencing reactions when the device is closed with a cover component.

Sealing Solutions.

In embodiments employing open PCR, the nucleic acid amplification and/or sequencing reaction mixture in the reaction well of the device is protected from evaporation or contamination by a layer of a sealing solution over the reaction mixture. The sealing solution may be any suitable fluid or semifluid that is immiscible or forms an immiscible layer over the reaction mixture. The sealing solution may be a synthetic material or a natural product. In some embodiments, the density of the sealing solution may be less than that of the reaction mixture sealed by the sealing solution. In some embodiments, the sealing solution may not inhibit the nucleic acid amplification reaction and/or sequencing reaction. The sealing solution may be stable at both high temperature and low temperature. The sealing solution may not mix into the nucleic acid amplification mixture and/or the sequencing reaction mixture. In some embodiments, the sealing solution is an oil. In some embodiments, the sealing solution may be a mineral oil.

Detection Components.

The system may include a detection component, where the detection component is configured to detect at least one product of the nucleic acid amplification. This detection may identify the corresponding nucleic acid sequence of the nucleic acid amplification product, which may provide a nucleic acid sequence identification of the individual. The detection component may be a fluorescent dye detection component, a semiconductor detection component, or a pyrophosphate detection component. In some embodiments, detection component is a fluorescent dye detection component, which may optionally be a mobility dependent fluorescent dye detection component. In some embodiments, the mobility dependent fluorescent dye detection component is capillary electrophoresis instrumentation with fluorescence detection.

Any or all of these additional components may be used to identify the individual.

Kits.

The invention also provides for kits. A kit may contain one or more devices of any of the various embodiments of the devices described herein, where the device may have any combination of features as described here, and may optionally contain instructions for using the device. The kit may further include a collection assistance liquid, including but not limited to a solvent, a detergent or a lysis solution. The kit may further include reagents for stabilizing the biological sample on the base substrate component of the device for archiving or shipping. The kit may further include reagents for analysis of the sample, including but not limited to antibodies, stains, indicators, agar plates, or nucleic acid amplification reagents. The kit may contain other reagents for reactions such as PCR amplification reactions, nucleic acid sequencing reactions, or analyses such as STR, SNP or Indel analyses. The kit may contain a sealing solution for sealing the reaction mixtures on the base substrate component during reactions. The kit may contain one or more proteases for extraction of the nucleic acid from the biological sample collected to the base substrate component of the device.

The kit may include storage enclosures for the device containing the biological sample and/or the nucleic acid, and may also contain directions for archiving. The kit may further include mailing enclosures for the device containing the biological sample or nucleic acid.

The enclosure included in a kit may include a frame to prevent contamination of any portion of the device. Any portion of the at least one enclosure may include an identifier to associate any of the portions of the device with the ridge and valley signature obtained at the time that the biological sample was collected. The identifier may further associate the device, the base substrate component of the device, the ridge and valley signature, in any combination with the individual providing the sample. In various embodiments, the identifier is alphanumeric, graphical, magnetic, or electromagnetic. In some embodiments, the identifier is a barcode.

In some embodiments, the kit may include instructions for use of the device, storage of the substrate or device after collection of the sample; amplification and/or nucleic acid sequencing reactions of the nucleic acid performed on the substrate of the device, and for relaying the image of the at least one ridge and valley signature to a database. The kit may include instructions for mailing the device after collection of the sample to another facility for analysis or archiving.

Methods.

Figure 5:
FIG. 5 is a graphical representation of a fingerprint image obtained using the device of FIG. 4.
Figure 6:
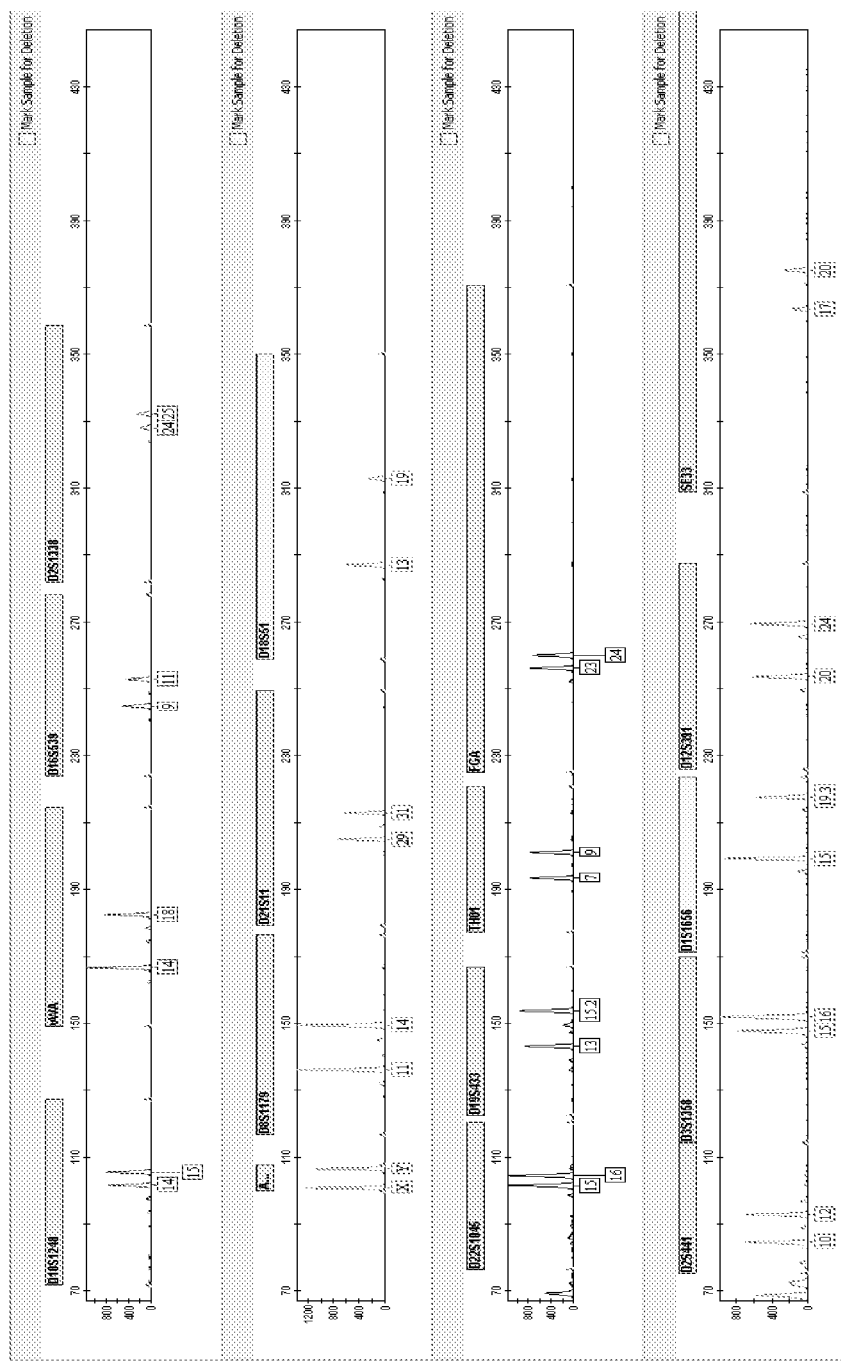
FIG. 6 is a graphical representation of a STR analysis of nucleic acid collected from an individual using the device of FIG. 4.

Both the fingerprint and the biological sample may be provided to be of sufficient quality/quantity to identify the individual. The image of the fingerprint obtained by scanning through the base substrate component, and, optionally, the mask component may be provided in high quality. When the image of the fingerprint is processed according to the requirements of any organization holding a database for reference, the digitized fingerprint may meet the threshold requirement. As may be seen in Examples 2 and 4, and particularly in FIGS. 5 and 11, acquiring a fingerprint according to the methods described here, fingerprints scored at the highest level, NIST quality score I, may be obtained. Therefore, a fingerprint image of high quality is provided which may be processed electronically in any suitable fashion, to assign minutiae or other categorizing characteristics, and be suitable for transmission to any agency for database comparison or for storage in a database. One non-limiting example is the Integrated Automated Fingerprint Identification System (IAFIS) which is maintained by the Federal Bureau of Investigation, a United States government agency.

In some embodiments, the at least first imaging component is an optical scanner, where the optical scanner includes a LED, laser diode, incandescent light source, or a multispectral imager. The at least first imaging component may alternatively be a camera, an active pixel imager, a CMOS imager, an imager that images in multiple wavelengths, a CCD camera, a photo detector array, and a TFT imager. The at least one ridge and valley signature may be collected electronically. The scanning surface of the at least first imaging component may be formed from a material selected from a plastic, a polyolefin, a polystyrene, a metal, a metal alloy, a glass, a silicon or combinations thereof. In some embodiments, the material of the scanning surface is transparent or translucent.

For the acquisition of nucleic acids of sufficient quantity and quality from a fingerprint, several factors may need to be addressed. To ensure sufficient quantity, an individual may be instructed to touch a portion of his face one or several times with the finger to be imaged prior to firmly pressing that finger on a base substrate component placed over the scanning portion of fingerprint imaging system. This may not be necessary in some embodiments of the method. The base substrate component useful in the method may be polymeric film or glass. In some embodiments, the polymeric film base substrate component may be a synthetic polymeric film. In other embodiments, the polymeric film base substrate component may be a natural polymer, including but not limited to starch, an agarose, an alginate, a carrageenan, and the like. In some embodiments, the base substrate component may be non-adhesive. In various embodiments, the base substrate component may be transparent or translucent.

Another aspect is obtaining high quality STR profiles from the nucleic acids deposited at the same time as a fingerprint. In some scenarios, a complicating effect is seen with other substances present in the deposited biological sample. While commercially available direct amplification STR chemistries are optimized to handle biological samples that may contain indigo, hematin and humic acid, all of which are inhibitors of the PCR amplification process, no system is optimized for the types of inhibitors possibly present in the biological samples acquired from a fingerprint deposition. Depending on the specific donor and the physiological condition of the skin of the individual at the time of fingerprinting, different amounts of sebum and sweat may be present. Sebum is produced by sebaceous glands and contain wax monoesters (approx. 25%), triglycerides (approx, 40%), free fatty acids (approx. 15%) and squalene (approx 10-15%). Sweat includes salts, urea, sugar and ammonia. Further, materials such as cosmetics, hair products, and sunscreens may be present when an individual deposits a fingerprint image containing a biological sample. Some or all of these chemicals may contribute to PCR inhibition. The normal skin pH of about 5.4 may also impact PCR efficiency under direct amplification workflows. Adjustment of the PCR master mixture composition may reduce the inhibiting effects of any of these materials. Evaluating a number of master mix/buffers, both commercially available buffers as well as other combinations, it has been discovered that the GLOBAL FILER ® master mix provides the most robust results. This particular master mix provides a higher concentration of one or more polymerases as well as an increased percentage of bovine serum albumin (BSA). Both of these master mix components assist in overcoming inhibitors found in DNA samples acquired from fingerprints. It has been surprisingly found that use of the sample concentration swab to concentrate the sample and direct amplification as described here can combine to provide high quality STR analyses from the highly limited amount of nucleic acids deposited within a fingerprint, even with interference from other substances also present. As can be seen in Examples 1-5 and the accompanying FIGS. 3, 6, 9, 12, 15, and 16, the electropherogram analysis can definitively identify the individual supplying the nucleic acids.

Methods for collection of a biological sample containing at least one nucleic acid and collection of at least one ridge and valley signature of an appendage of an individual, are provided, including the steps of providing at least a first imaging component. The at least first imaging component is configured to provide an energy wave capable of imaging the at least one ridge and valley signature; and have a scanning surface configured to permit the energy wave to penetrate the scanning surface. The method also includes the step of providing a device having a base substrate component having at least a first surface area, where the base substrate component is configured to permit the energy wave to penetrate the substrate; collect the biological sample from the appendage of the individual; and be made of one or more materials configured to be compatible with reaction conditions of a nucleic acid amplification reaction. The device may be any of the embodiments of the devices described here, with any combination of components. The method also includes the step of positioning an appendage of the individual on the scanning surface and in contact with the base substrate component, thereby collecting the biological sample; and collecting the at least one ridge and valley signature from the appendage imaged by the energy wave. The appendage image may be a finger, toe, palm of a hand or sole of a foot. The steps of collecting the biological sample and collecting the at least one ridge and valley signature may be performed simultaneously.

In some embodiments, the at least first imaging component may be an optical scanner or a capacitance scanner, and the at least one ridge and valley signature may be collected electronically.

The method may further include the step of transmitting the at least one ridge and valley signature of the individual to at least one database comprising ridge and valley signatures selected from the group consisting of a forensic, criminal, identity, child identity, missing persons, immigration, department of motor vehicles, terrorist, paternity, arrestee, convict database, access control or any combination thereof.

The method may further include the step of providing an identifier on at least one component of the device to associate the biological sample of the individual with the at least one ridge and valley signature of the individual, wherein the identifier is alphanumeric, graphical, magnetic, or electromagnetic. In some embodiments, the identifier is a barcode.

The method may also include the step of archiving at least the base substrate component of the device after performing the step of collecting the biological sample.

The method may further include the step of mailing the device to another location for archiving or testing, after performing the step of collecting the biological sample.

The method may further entail the step of subjecting the biological sample collected to the base substrate component to a nucleic acid amplification reaction. In some embodiments, the nucleic acid amplification reaction is a polymerase chain reaction. The method may further entail the step of performing a nucleic acid sequencing reaction while still present on the base substrate component. In some embodiments, the nucleic acid amplification reaction and the nucleic acid sequencing reaction may be performed in the same reaction well, without transfer or stoppage between processes. In some embodiments, the amplification reaction may be one component of a STR analysis, a SNP analysis, or an Indel analysis.

The method may further entail the step of placing a mask component of the device upon the base substrate component, thereby surrounding the at least first surface area of the base substrate component. The mask component may be made of one or more materials compatible with reaction conditions of a nucleic acid amplification reaction. In some embodiments, the step of placing the mask component upon the base substrate component is performed before the step of collecting the biological sample. In other embodiments, the step of placing the mask component upon the base substrate component is performed after the step of collecting the biological sample and before the step of subjecting the biological sample on the base substrate component to a nucleic acid amplification reaction. The method may further include the step of sealing the nucleic acid amplification reaction with a sealing solution. The reaction well may have no other upper closure besides the sealing solution. Alternatively, the method may include the step of placing a cover component of the device over the biological sample collected to the base substrate component during the nucleic acid amplification reaction. In some embodiments, the step of placing the cover component over the biological sample on the base substrate component is performed after reagents for the nucleic acid amplification reaction have been added to the biological sample on the base substrate component, and before the reaction commences. The method may also include the step of placing a cover component over the biological sample collected to the base substrate component for shipping or archiving prior to a nucleic acid amplification. The method may further include the step of detecting a sequence of the nucleic acid, thereby identifying the individual. The method may further include the step of transmitting the nucleic acid sequence identity of the individual to at least one database comprising nucleic acid sequence identities selected from the group consisting of a forensic, criminal, identity, child identity, missing persons, immigration, department of motor vehicles, terrorist, paternity, arrestee, convict database, access control and any combination thereof.

Methods of identifying an individual are provided, including the step of providing at least a first imaging component configured to provide an energy wave capable of imaging at least one ridge and valley signature of an appendage of an individual; and comprise a scanning surface configured to permit the energy wave to penetrate the scanning surface. The method also includes the step of providing a device comprising a base substrate component having at least a first surface area, where the substrate component is configured to permit the energy wave to penetrate the substrate; collect a biological sample comprising nucleic acid from the appendage of the individual; and be made of one or more materials configured to be compatible with reaction conditions of a nucleic acid amplification reaction. The device may be any of the embodiments of the devices described here, with any combination of components. The method also includes the step of positioning the appendage of the individual on the scanning surface and in contact with the at least first surface area of the base substrate component, thereby collecting the biological sample; collecting the at least one ridge and valley signature from the appendage imaged by the energy wave, thereby providing a ridge and valley signature identification of the individual; subjecting the nucleic acid of the biological sample collected to the base substrate component to a nucleic acid amplification reaction; and detecting a sequence of the nucleic acid, thereby identifying the individual. The steps of collecting the biological sample and collecting the at least one ridge and valley signature may be performed simultaneously.

In some of the embodiments, the at least first imaging component may be an optical scanner or a capacitance scanner. In various embodiments, the at least one ridge and valley signature may be collected electronically. In some embodiments, the appendage may be a finger, toe, palm of a hand or sole of a foot. In other embodiments, the nucleic acid amplification reaction may be a polymerase chain reaction. In various embodiments, the method may include the step of performing a DNA sequencing reaction while still present on the base substrate component. In some embodiments, the amplification reaction may be one component of a STR analysis, a SNP analysis, or an Indel analysis.

The method may further include the step of placing a mask component of the device upon the base substrate component, thereby surrounding the at least first surface area of the substrate, where the mask component is made of one or more materials compatible with reaction conditions of a nucleic acid amplification reaction. In some embodiments, the step of placing the mask component upon the base substrate component may be performed before the step of collecting the biological sample. In other embodiments, the step of placing the mask component upon the base substrate component may be performed after the step of collecting the biological sample and before the step of subjecting the biological sample on the substrate component to a nucleic acid amplification reaction.

The method may further include the step of sealing the nucleic acid amplification reaction with a sealing solution. The nucleic acid amplification reaction mixture may have no other upper enclosure.

The method may further include the step of placing a cover component of the device over the biological sample collected to the base substrate component. The cover may be placed over the at least first surface of the base substrate component containing the nucleic acid for shipping and archiving the device after collection of the biological sample. In some embodiments, the cover component may be placed over the biological sample on the substrate component after reagents for the nucleic acid amplification reaction have been added to the biological sample on the base substrate component, and before the reaction commences.

The method may further include the step of transmitting the at least one ridge and valley signature of the individual to at least one database comprising ridge and valley signatures selected from the group consisting of a forensic, criminal, identity, child identity, missing persons, immigration, department of motor vehicles, terrorist, paternity, arrestee, convict database, access control or any combination thereof.

The method may further include the step of providing an identifier on at least one component of the device to associate the biological sample of the individual with the at least one ridge and valley signature of the individual, where the identifier is alphanumeric, graphical, magnetic, or electromagnetic. In some embodiments, the identifier is a barcode.

The method may further include the step of archiving at least the base substrate component of the device after performing the step of collecting the biological sample.

The method may further include the step of mailing the device to another location for archiving or testing, after performing the step of collecting the biological sample.

The method may also include the step of transmitting the nucleic acid sequence identity of the individual to at least one database comprising nucleic acid sequence identities selected from the group consisting of a forensic, criminal, identity, child identity, missing persons, immigration, department of motor vehicles, terrorist, paternity, arrestee, convict database, access control and any combination thereof.

Those having ordinary skill in the art will understand that many modifications, alternatives, and equivalents are possible. All such modifications, alternatives, and equivalents are intended to be encompassed herein.

EXAMPLES

The following procedures are representative of procedures that can be employed for the collection, analysis and archiving/cataloging biological samples and biometric data from an individual.

Example 1

A device as shown in FIG. 2 is used. Fingerprints are imaged by contacting one or more fingers of at least one individual on base substrate component made from a piece of MICROAMP® clear adhesive film about 2.5 cm×about 5 cm, placed on the scanning surface of a LUMIDIGN™ optical scanner. The open PCR reaction chamber (8 mm in diameter) over each fingerprint is formed by placing a SECURESEAL 8-well gasket (Grace Bio-labs, AB8R-0.5) on top of the adhesive film containing the fingerprint nucleic acid deposit (FIG. 2). In this example, the two chambers on top left (210-1.3 and 210-1.4) contain 007 control DNA, the two chambers at lower left (210-1.1 and 210-1.2) are formed over fingerprints from donor 1 and the four chambers on the right (210-1.5, 210-1.6, 210-1.7 and 210-1.8) are over fingerprints from donor 2. Each chamber over a fingerprint is filled with 50 ul NGM® SELECT EXPRESS PCR reaction mix, which includes primers, polymerases, dNTPs, dye labeled ddNTPs, and other reagents and buffers for amplification of nucleic acid. The two chambers for positive controls are filled with 50 ul NGM® SELECT EXPRESS PCR reaction mix containing 5 ng of 007 control DNA. The top of the chambers is sealed with another piece of MICROAMP® clear adhesive film. The assembled fingerprint PCR device is placed on the AB 9700 flat thermal cycler block and secured on the thermal block with tape.

The novel nature of the device of FIG. 2 requires modification of typical thermocycling conditions to achieve optimal results. The resulting modified PCR thermal cycling conditions are: 96.5° C./1:30 m, (98° C./15 s, 56° C./46 sec, 66° C./49 sec) 29×, 60° C./7 min, 4° C.-hold.

Figure 3:
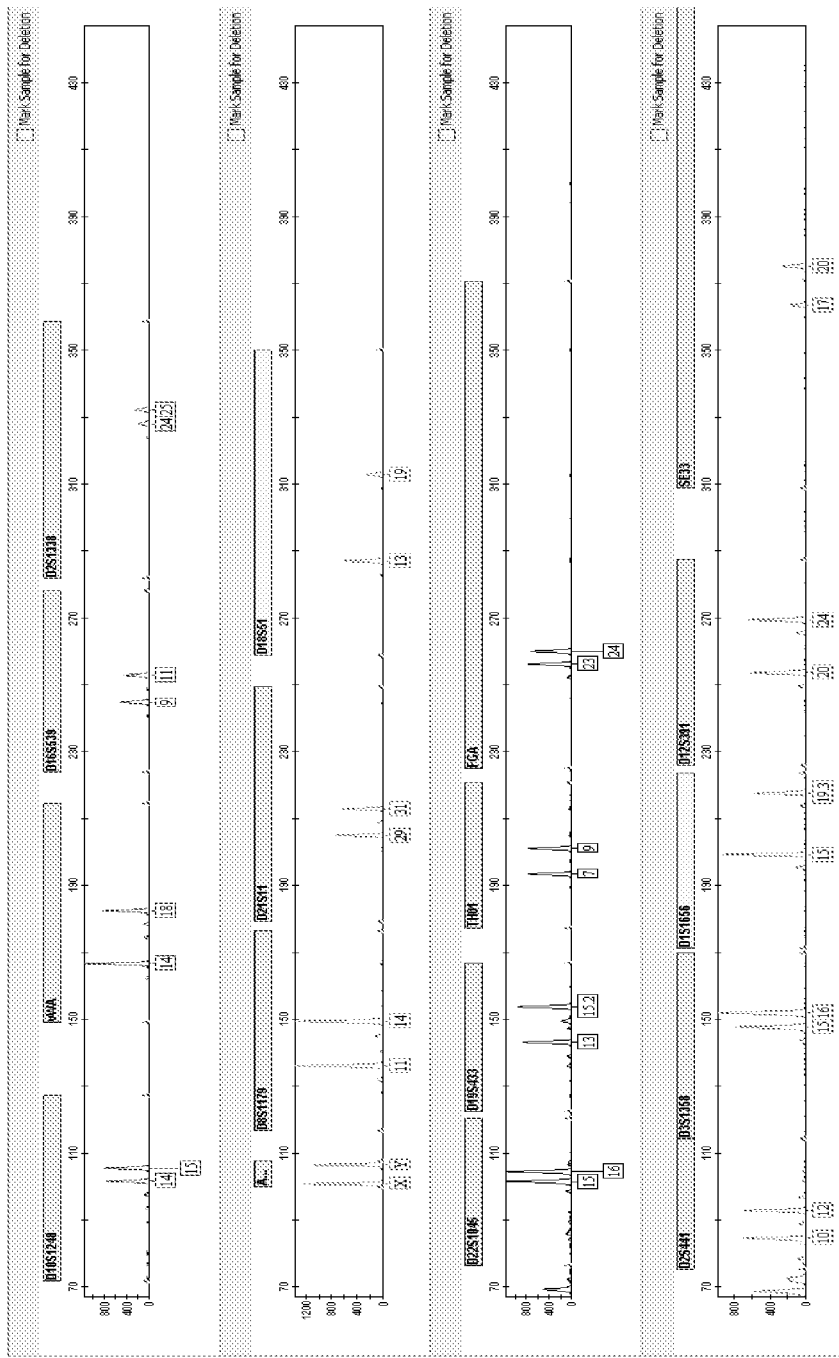
FIG. 3 is a graphical representation of a STR analysis of nucleic acid collected from an individual using the device of FIG. 2.

After thermal cycling, and a 1 ul aliquot of each of the PCR reactions is mixed with GS500 size standard and deionized formamide and analyzed using an ABI 3130xl capillary electrophoresis instrument using the default conditions for NGM® SELECT EXPRESS PCR samples: Oven: 60° C., Prerun: 15 kV, 180 s, Injection: 3 kV, 10 s, Run: 15 kV, 1500 s, Capillary length: 36 cm, Separation polymer: POP4™ polymer and Dye set: G5. The resulting STR electropherogram is analyzed using GENEMAPPER® ID-X software (Applied Biosystems). Full STR profiles for all 16 STR markers and the sex determination marker Amelogenin are obtained for a sample from one of reaction wells 210-1.5, 210-1.6, 210-1.7 or 210-1.8 (FIG. 3). From left to right in the uppermost lane, the alleles for D1051248, vWA, D165539, and D2S1338 are shown; the second lane from the top of the page shows the alleles for Amelogenin, D8S1179, D21S11, and D18551; the third lane from the top shows the alleles for D22S1045, D195433, TH01, and FGA; and the bottom panel shows the alleles for D2S441, D3S1358, D1S1656, D125391, and SE33.

Example 2

A device as shown in FIG. 4 is used and placed on the scanning surface of a LUMIDIGN™ optical scanner. The cover component 404 is flipped open. A fingerprint is imaged by contacting a finger of an individual to and covering the entire region 410-1. The fingerprint image (FIG. 5) obtained is of NIST quality score 1. The cover component can be flipped closed for mailing to a central laboratory or it may be processed after removal from the fingerprint scanning component. The cover component layer and the mask component layer may be removed prior to amplification of the nucleic acid deposited within region 410-1. The base substrate component layer is transferred to a thermal cycler including but not limited to an AB 9700 flat thermal cycler block and secured on the thermal block.

The assembled fingerprint PCR device is placed on the AB 9700 flat thermal cycler block and secured on the thermal block with tape. NGM® SELECT EXPRESS PCR reaction mix (50 ul) is added to the region 410-1 containing the nucleic acid collected from the contact of the finger with the base substrate component. The PCR reaction mix may contain PCR compatible color dye to aid the PCR product recovery later.

The PCR reaction mix is sealed by adding a sealing solution such as mineral oil over the PCR reaction mix. The novel nature of the open PCR device of FIG. 4 requires modification of typical thermocycling conditions to achieve optimal results. The resulting modified PCR thermal cycling conditions are: 96.5° C./1:30 m, (98° C./15 s, 56° C./46 sec, 66° C./49 sec) 29×, 60° C./7 min, 4° C.-hold.

After thermal cycling, and a 1 ul aliquot of each of the PCR reactions is mixed with GS500 size standard and deionized formamide and analyzed using an ABI 3130xl capillary electrophoresis instrument using the default conditions for NGM® SELECT EXPRESS PCR samples: Oven: 60° C., Prerun: 15 kV, 180 s, Injection: 3 kV, 10 s, Run: 15 kV, 1500 s, Capillary length: 36 cm, Separation polymer: POP4™ polymer and Dye set: G5. The resulting STR electropherogram is analyzed using GENEMAPPER® ID-X software (Applied Biosystems). Full STR profiles for all 16 STR markers and the sex determination marker Amelogenin are obtained (FIG. 6) From left to right in the uppermost lane, the alleles for D10S1248, vWA, D16S539, and D2S1338 are shown; the second lane from the top of the page shows the alleles for Amelogenin, D8S1179, D21S11, and D18S51; the third lane from the top shows the alleles for D22S1045, D19S433, TH01, and FGA; and the bottom panel shows the alleles for D2S441, D3S1358, D1S1656, D12S391, and SE33.

The addition of PCR reagents and addition of the sealing solution does not have to occur in the order described above. Equally, sealing solution of mineral oil can be added to the region 410-1 containing fingerprint nucleic acid deposit on the base substrate component and then 50 ul may be pipette through the sealing solution layer to contact the fingerprint nucleic acid deposit in region 410-1.

Example 3

Figure 9:
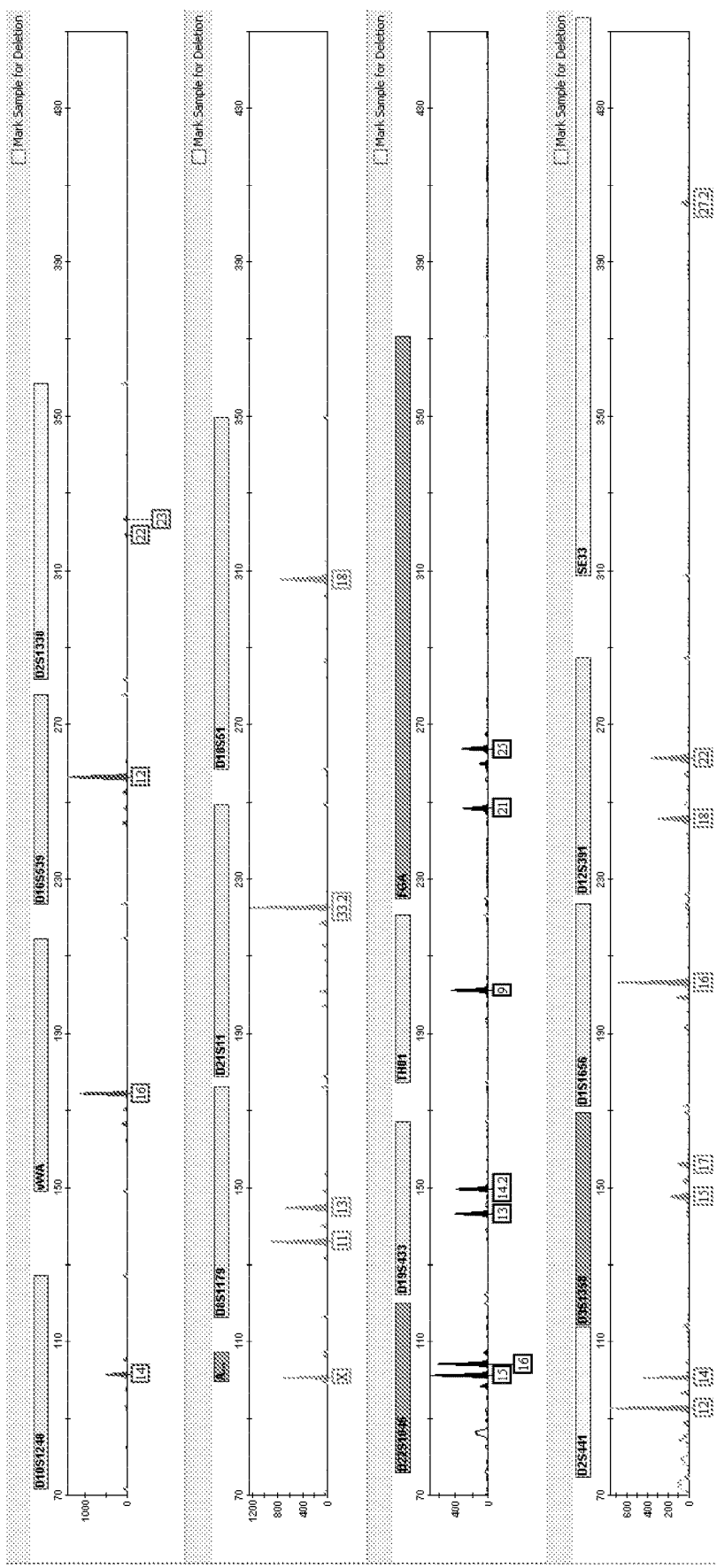
FIG. 9 is a graphical representation of a STR analysis of nucleic acid collected from an individual using the device of FIG. 8A.

A device 810A (FIG. 8) further demonstrates the feasibility of capturing DNA from a fingertip on a PCR compatible substrate with the subsequent formation of a PCR reaction chamber directly over the fingerprint on the substrate for direct STR analysis in-situ. The device is placed on the scanning surface of a LUMIDIGN™ optical scanner for collection of a fingerprint image and nucleic acid deposit from the contact of the finger upon the base substrate component 810A. In one version of this device, the fingerprint nucleic acid is collected on a base component substrate 810A made from MICROAMP® clear adhesive film (Life Tech, 4306311). A reaction chamber (about 8 mm in diameter and about 1 mm diameter deep) over the region 810A-1, where the biological sample containing fingerprint nucleic acid 802A is deposited, is formed by placing a SECURE-SEAL well (Grace Bio-labs, AB8R-0.5) upon the base component layer adhesive film 810A surrounding the region 810A-1 containing the fingerprint nucleic acid deposit 802A. Once the two layers are bonded, the resulting chamber is filled with 50 ul NGM® SELECT EXPRESS PCR reaction mix. The top of the chamber is sealed with another piece of blank MICROAMP® clear adhesive film. The assembled fingerprint PCR device is placed on the AB 9700 flat thermal cycler block and secured. The thermal cycling conditions are: 96.5° C./1:30 m, 29 cycles of (98° C./15 s, 56° C./46 sec, 66° C./49 sec), 60° C./7 min and 4° C.-hold. After thermal cycling, the top cover of the PCR chamber is cut open with a knife. The PCR reaction is recovered using a pipette and was mixed with GS500 size standard and deionized formamide and is analyzed using an AB 3130xl capillary electrophoresis instrument using the following conditions: Oven: 60° C., Prerun: 15 kV, 180 s, Injection: 3 kV, 10 s, Run: 15 kV, 1500 s, Capillary length: 36 cm, Separation polymer: POP4™ polymer and Dye set: G5. The resulting STR electropherograms is analyzed using GENEMAPPER® ID-X software (Applied Biosystems). Full STR profiles for all 16 STR markers and the sex determination marker Amelogenin are obtained (FIG. 9). STR profile quality could be further improved by further optimizing PCR thermal cycling conditions. From left to right in the uppermost lane, the alleles for D10S1248, vWA, D16S539, and D2S1338 are shown; the second lane from the top of the page shows the alleles for Amelogenin, D8S1179, D21S11, and D18S51; the third lane from the top shows the alleles for D22S1045, D19S433, TH01, and FGA; and the bottom panel shows the alleles for D2S441, D3S1358, D1S1656, D12S391, and SE33.

Example 4

In one embodiment, a device 1001 (FIG. 10) may be fabricated using the following procedure:
1. Put a piece of 11 mm diameter sticky tape at the bottom of a concave depression on a glass base substrate component 1010.
2. Apply a few drops of commerically available silanizing reagent (for example, RAIN-X®) to the glass base substrate component 1010. Use a cotton swab to wipe the remaining exposed glass surface to remove the availability of hydroxyl groups on the swabbed portion of the glass base substrate component 1010.
3. Repeat step 2 once.
4. Clean the slide surface with a paper tissue.
5. Remove the sticky tape.
6. Put a transparent mask component 1003, made from a polymeric film, with about a 10 mm dia. hole over the slide, aligning the hole in the mask component with the untreated hydrophilic region on slide.

Figure 11:
FIG. 11 is a graphical representation of a fingerprint image obtained using the device of FIG. 10.
Figure 12:
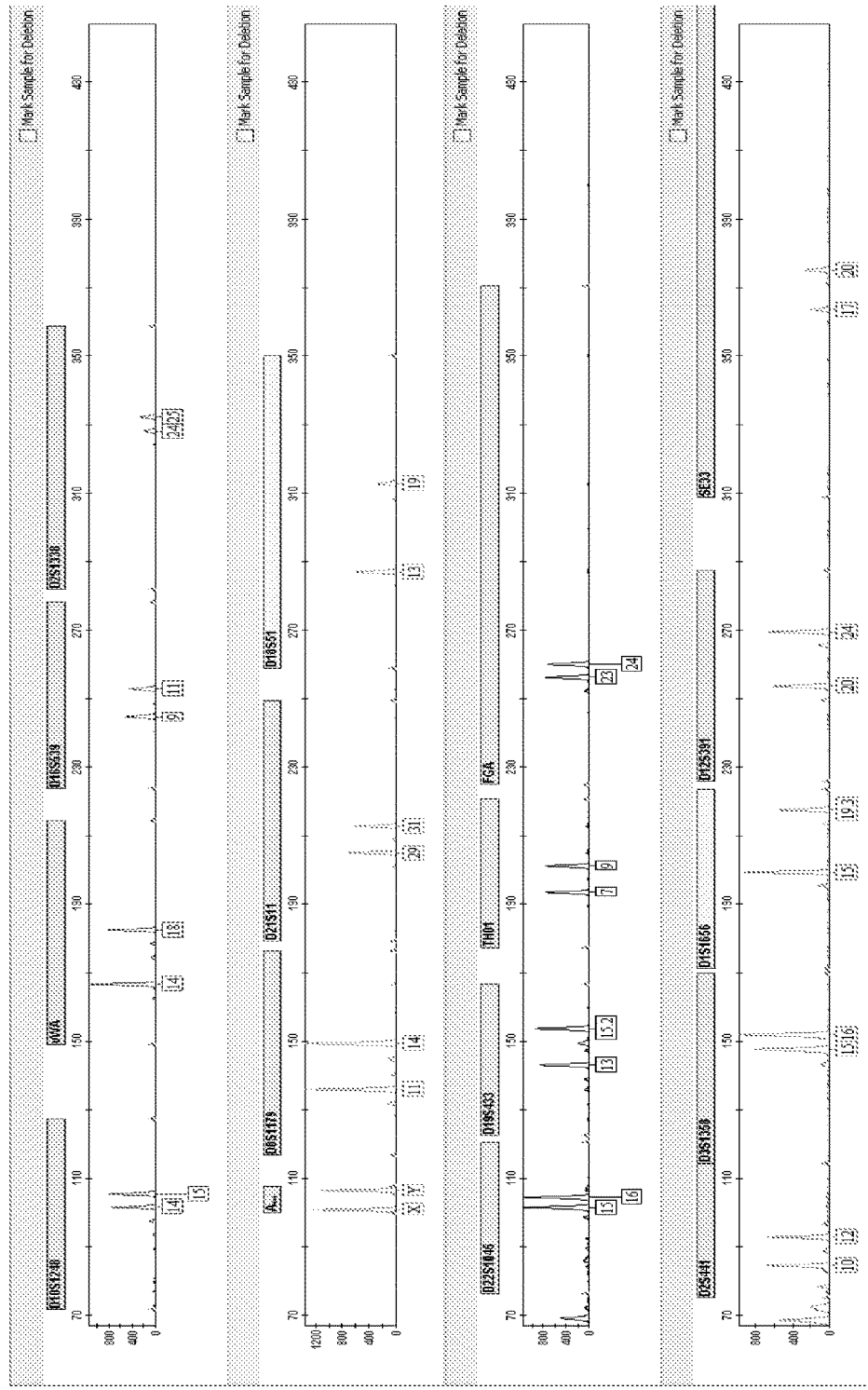
FIG. 12 is a graphical representation of a STR analysis of nucleic acid collected from an individual using the device of FIG. 10.

During fingerprint collection, device 1001 is placed over Lumidigm fingerprint scanner to take a fingerprint image of the index finger in contact with the hydrophilic region 1010-1. A high quality fingerprint image is obtained with NIST quality score of 1 (FIG. 11). During STR PCR analysis, the transparent mask component 1003 is removed from device 1001. The device 1001 containing fingerprint nucleic acid deposit within region 1010-1, is placed on an AB 9700 thermal cycler. 10 ul NGM® SELECT EXPRESS PCR mix is added to the fingerprint nucleic acid deposited within the hydrophilic region 1010-1. The reaction mixture is sealed with a layer of mineral oil (approximately 200 ul). The thermal cycling conditions are: 96.5° C./1:30 m, 29 cycles of (98° C./15 s, 56° C./46 sec, 66° C./49 sec), 60° C./7 min and 4° C.-hold. After thermal cycling, The PCR reaction is recovered using a pipette and is mixed with GS500 size standard and deionized formamide. An aliquot of this mixture is analyzed using a AB 3130xl capillary electrophoresis instrument using the following conditions: Oven: 60° C., Prerun: 15 kV, 180 s, Injection: 3 kV, 10 s, Run: 15 kV, 1500 s, Capillary length: 36 cm, Separation polymer: POP4™ polymer and Dye set: G5. The resulting STR electropherogram is analyzed using GENEMAPPER® ID-X software (Applied Biosystems). Full STR profiles for all 16 STR markers and the sex determination marker Amelogenin are obtained (FIG. 12). From left to right in the uppermost lane, the alleles for D10S1248, vWA, D16S539, and D2S1338 are shown; the second lane from the top of the page shows the alleles for Amelogenin, D8S1179, D21S11, and D18S51; the third lane from the top shows the alleles for D22S1045, D19S433, TH01, and FGA; and the bottom panel shows the alleles for D2S441, D3S1358, D1S1656, D12S391, and SE33.

Example 5

A first instance of the device 1401A (FIG. 14A) has a base substrate component 1410A made of a thin film which is compatible with both fingerprint collection and PCR reaction conditions. The base substrate component 1410A is coated with PCR compatible adhesive. A fingerprint image is collected and fingerprint nucleic acid 1402A is deposited within region 1410A-1. The open PCR reaction well is formed when mask component 1403A, which is made from a thin (for example, 1 mm thick) glass slide having a through hole 1407A, having a diameter of about 10 mm, is bonded with the base substrate 1410A containing the fingerprint nucleic acid in region 1410A-1. The though hole is aligned to preserve access to region 1410A-1. When the bond is accomplished the open PCR device (1401B) is ready to amplify the fingerprint nucleic acid deposit 1402B in-situ, not requiring any handling or transfer.

A second instance of the device 1403B is formed in the same manner as described in the previous paragraph, differing only in that the upper surface of the mask component 1403B is treated to create a hydrophobic surface, for instance, by treating with a silanizing reagent, in order to retain the reagents used in the nucleic acid amplification reaction.

Both the first instance and the second instance of device 1403B on an AB 9700 thermal cycler. PCR master mix (20 ul NGM® SELECT EXPRESS PCR mix) is added to the exposed base substrate component region containing fingerprint nucleic acid, and the mixture is covered with about 200 ul mineral oil to seal the reaction for open PCR.

The thermal cycling conditions are: 96.5° C./1:30 m, 29 cycles of (98° C./15 s, 56° C./46 sec, 66° C./49 sec), 60° C./7 min and 4° C.-hold. After thermal cycling, an aliquot of each PCR reaction is recovered using a pipette and is each mixed with GS500 size standard and deionized formamide. Each individual sample is analyzed using an AB 3130xl capillary electrophoresis instrument using the following conditions: Oven: 60° C., Prerun: 15 kV, 180 s, Injection: 3 kV, 10 s, Run: 15 kV, 1500 s, Capillary length: 36 cm, Separation polymer: POP4™ polymer and Dye set: G5. The resulting STR electropherograms are analyzed using GENEMAPPER® ID-X software (Applied Biosystems). Full STR profiles for all 16 STR markers and the sex determination marker Amelogenin were obtained for both open PCR devices. (See FIG. 15 (first instance of the device having a hydrophilic upper surface of the mask component) and FIG. 16 (second instance of the device having a hydrophobic surface of the mask component). From left to right in the uppermost lane, the alleles for D10S1248, vWA, D16S539, and D2S1338 are shown; the second lane from the top of the page shows the alleles for Amelogenin, D8S1179, D21S11, and D18S51; the third lane from the top shows the alleles for D22S1045, D19S433, TH01, and FGA; and the bottom panel shows the alleles for D2S441, D3S1358, D1S1656, D12S391, and SE33.

Example 6

A biological sample containing nucleic acid is deposited by contacting a finger to and is collected on a 3M PP2200 film, performed in triplicate. The deposit was then rinsed with 25 ul NGM® SELECT EXPRESS PCR reaction mix. Each of the three 5 ul rinses is transferred to a separate well of a TEFLON printed slide with 4 mm well diameter. Rinses are then covered with a drop of mineral oil. Three wells each containing 5 uL of NGM® SELECT EXPRESS PCR reaction mix plus 1 ng of 007 control DNA are also loaded on the same slide. The slide is then placed on an AMPLISPEED® thermal cycler and PCR reaction is performed using the following thermal cycling conditions: 95° C./1 m, (94° C./3 s, 59° C./16 sec, 65° C./29 sec) 29×, 60° C./5 min, 4° C.-hold.

After thermal cycling the PCR reactions are individually recovered and mixed with GS500 LIZ® size standard and deionized formamide. Each individual sample is analyzed using an AB 3130xl capillary electrophoresis instrument using the following conditions: Oven: 60° C., Prerun: 15 kV, 180 s, Injection: 3 kV, 10 s, Run: 15 kV, 1500 s, Capillary length: 36 cm, Separation polymer: POP4™ polymer and Dye set: G5. The resulting STR electropherograms are analyzed using GENEMAPPER® ID-X software (Applied Biosystems).

Figure 19:
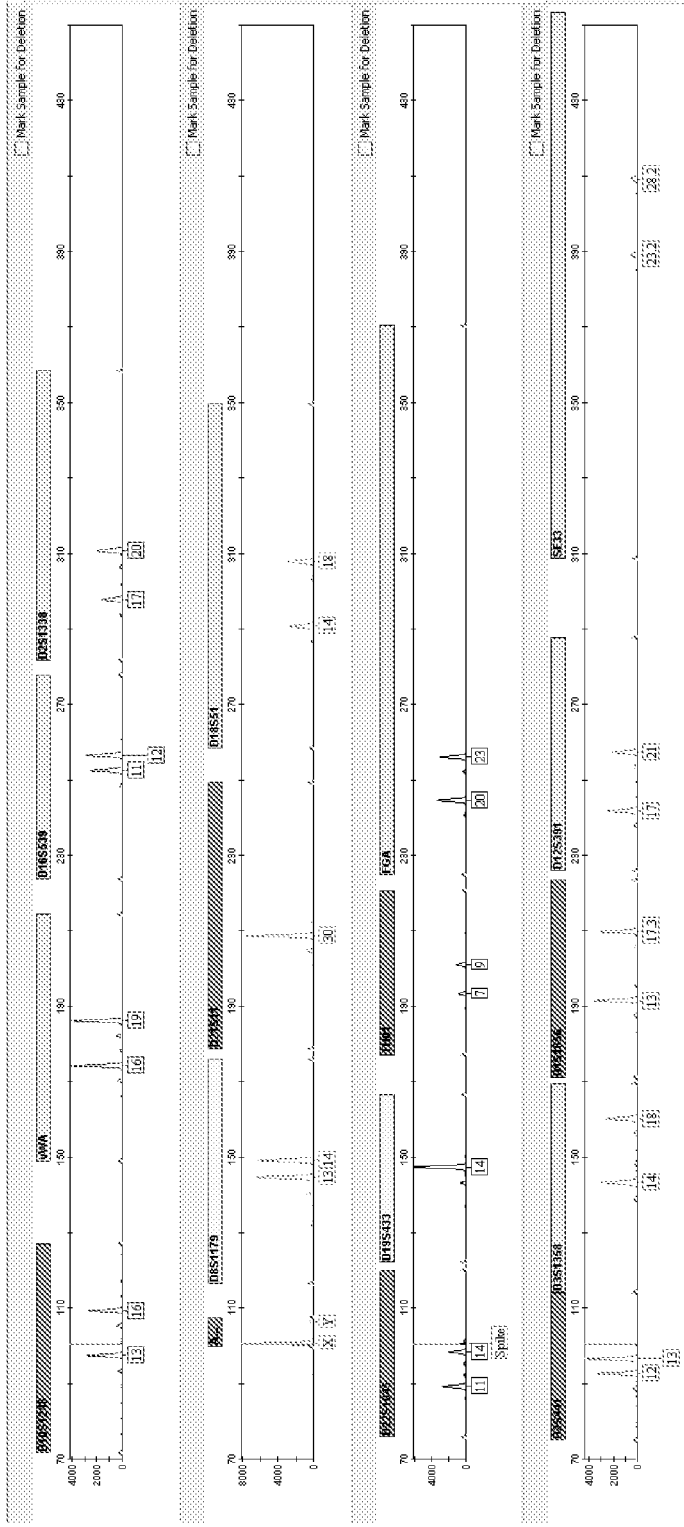
FIG. 19 is a graphical representation of a STR analysis of nucleic acid amplified using the base substrate component of FIG. 18.
Figure 20:
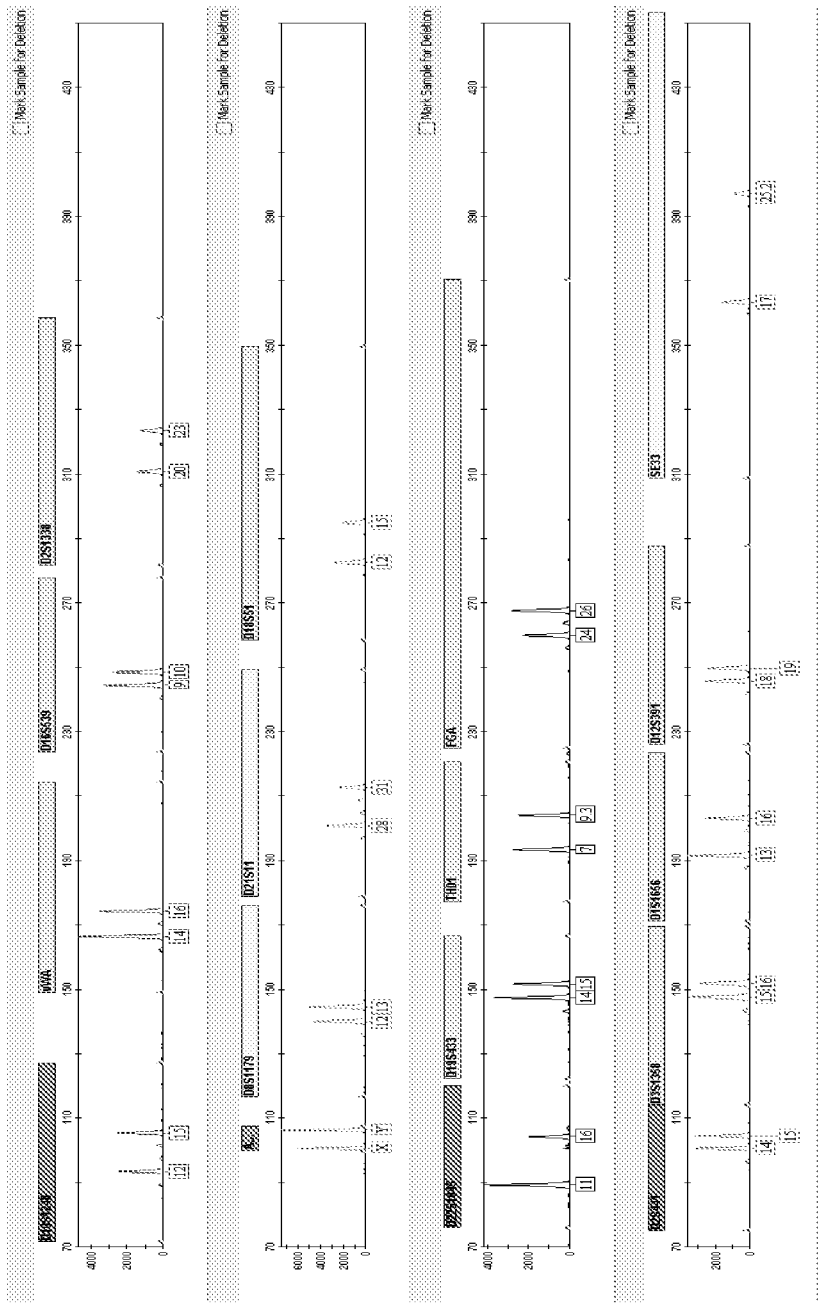
FIG. 20 is a graphical representation of a STR analysis of nucleic acid amplified using the base substrate component of FIG. 18.

Of the three fingerprint rinse samples, one gave full profile (See FIG. 19) and the other two gave partial profiles. Full profiles were obtained from all three control samples (See FIG. 20).

While the foregoing specification teaches the principles of the present invention, with examples provided for the purpose of illustration, it will be appreciated by one skilled in the art from reading this disclosure that various changes in form and detail can be made without departing from the spirit and scope of the invention.

What is claimed:

1. A method for collection of a biological sample comprising at least one nucleic acid and at least one ridge and valley signature of an appendage of an individual, comprising the steps of:
    a) providing at least a first imaging component configured to:
        i) provide an energy wave capable of imaging the at least one ridge and valley signature; and
        ii) comprise a scanning surface configured to permit the energy wave to penetrate the scanning surface;
    b) providing a device comprising a base substrate component having at least a first surface area, wherein the base substrate component is configured to:
        i) permit the energy wave to penetrate the substrate;
        ii) collect the biological sample from the appendage of the individual; and
        iii) comprise one or more materials configured to be compatible with reaction conditions of a nucleic acid amplification reaction;
    c) positioning an appendage of the individual on the scanning surface and in contact with the base substrate component, thereby collecting the biological sample;
    d) collecting the at least one ridge and valley signature from the appendage imaged by the energy wave;
    e) subjecting the biological sample collected on the base substrate component to a nucleic acid amplification reaction; and
    f) performing a DNA sequencing reaction while the biological sample is still present on the base substrate component.

2. The method of claim 1, wherein the at least first imaging component is an optical scanner or a capacitance scanner.

3. The method of claim 2, wherein the at least one ridge and valley signature is collected electronically.

4. The method of claim 2, further comprising the step of transmitting the at least one ridge and valley signature of the individual to at least one database comprising ridge and valley signatures selected from the database group consisting of a forensic, criminal, identity, child identity, missing persons, immigration, department of motor vehicles, terrorist, paternity, arrestee, convict database, access control and any combination thereof.

5. The method of claim 2, further comprising the step of providing an identifier on at least one component of the device to associate the biological sample of the individual with the at least one ridge and valley signature of the individual, wherein the identifier is alphanumeric, graphical, magnetic, or electromagnetic.

6. The method of claim 5, wherein the identifier is a barcode.

7. The method of claim 2, further comprising the step of archiving at least the base substrate component of the device after performing the step of collecting the biological sample.

8. The method of claim 2, further comprising the step of mailing the device to another location for archiving or testing, after performing the step of collecting the biological sample.

9. The method of claim 1, wherein the amplification reaction is one component of a STR analysis, a SNP analysis, or an Indel analysis.

* * * * *